US012624352B2

(12) United States Patent (10) Patent No.: US 12,624,352 B2
Collins et al. (45) Date of Patent: May 12, 2026

(54) DNA-RESPONSIVE HYDROGELS

(71) Applicants: Massachusetts Institute of Technology, Cambridge, MA (US); President and Fellows of Harvard College, Cambridge, MA (US)

(72) Inventors: James J. Collins, Newton, MA (US); Helena de Puig Guixe, Barcelona (ES); Luis Ruben Soenksen Martinez, Boston, MA (US); Max English, Cambridge, MA (US); Raphael Gayet, Cambridge, MA (US); Nicolaas Angenent-Mari, Somerville, MA (US); Angelo S. Mao, Somerville, MA (US); Peter Q. Nguyen, Malden, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 885 days.

(21) Appl. No.: 16/778,524

(22) Filed: Jan. 31, 2020

(65) Prior Publication Data

US 2020/0308577 A1 Oct. 1, 2020

Related U.S. Application Data

(60) Provisional application No. 62/889,234, filed on Aug. 20, 2019, provisional application No. 62/823,272, filed on Mar. 25, 2019.

(51) Int. Cl.
| | |
|---|---|
| *C12N 15/11* | (2006.01) |
| *C08J 3/075* | (2006.01) |
| *C12N 9/22* | (2006.01) |
| *C12N 11/10* | (2006.01) |
| *C12Q 1/70* | (2006.01) |
| *G01N 27/02* | (2006.01) |

(52) U.S. Cl.
CPC .............. *C12N 15/11* (2013.01); *C08J 3/075* (2013.01); *C12N 9/22* (2013.01); *C12N 11/10* (2013.01); *C12Q 1/70* (2013.01); *C08J 2371/02* (2013.01); *C08J 2405/00* (2013.01); *C08J 2433/26* (2013.01); *C12N 2310/20* (2017.05); *C12N 2800/80* (2013.01); *G01N 27/021* (2013.01)

(58) Field of Classification Search
None
See application file for complete search history.

(56) References Cited

U.S. PATENT DOCUMENTS

2020/0032325 A1* 1/2020 Baughman ............... C12N 9/22

FOREIGN PATENT DOCUMENTS

WO WO-2014078636 A1 * 5/2014 ......... A61K 47/6903
WO WO-2017172860 A1 * 10/2017 ......... C12N 15/1093

OTHER PUBLICATIONS

Deshpande et al Advanced Functional Material, 9075-9082 (Year: 2016).*
Li et al Cell Research, 28, 491-493 (Year: 2018).*
Wei et al An. Chem., 87, 4275-4282 (Year: 2015).*
Xu et al ACS Nano, 4, 7, 4324-4330 (Year: 2010).*
English et al Science, 365, 780-785 (Year: 2019).*
Sicilia et al Biomater. Sci., , 2, 203-211 (Year: 2014).*
Parant et al Carbon 119 , 10-20 (Year: 2017).*
Deshpande et al Adv. Funct. Mater. 26, 9075-9082 (Year: 2016).*
Deshpande et al Advanced Functional Materials, 9075-9082 (Year: 2016).*
Knott et al Science, 361, 866-869 (Year: 2018).*
Gootenberg et al. Science 360, 439-444, (Year: 2018).*
Previtera et al Journal of Visualized Experiments, 90, e51323, 1-11 (Year: 2014).*
Xu ACS Nano, 4, 12, 7358-7362 (Year: 2010).*
Gao et al Gels, 1, 219-234; (Year: 2015).*
Creutzburg et al Nucleic Acids Research, vol. 48, No. 6, 3228-3243 (Year: 2020).*
Chen et al Science 360, 436-439 (Year: 2018).*
Han et al Science, 754-755 (Year: 2019).*
Nalefski et al Nucleic Acids Research, 52 , 4502-4522 (Year: 2024).*
Chen et al., Targeted Delivery of CRISPR/Cas9-Mediated Cancer Gene Therapy via Liposome-Templated Hydrogel Nanoparticles. Advanced Functional Materials. Dec. 8, 2017;27(46):1703036(1-9). doi: 10.1002/adfm.201703036. Epub Oct. 16, 2017. PMID: 29755309; PMCID:PMC5939593. Supporting Information, 13 pages.
Deshpande et al., DNA-Responsive Polyisocyanopeptide Hydrogels with Stress-stiffening capacity. Advanced Functional Materials. Dec. 1, 2016:26(48):9075-9082.
English et al., Programmable CRISPR-responsive smart materials. Science. Aug. 23, 2019;365(6455):780-785. doi: 10.1126/science. aaw5122. PMID: 31439791.
Badu-Tawiah et al., Polymerization-based signal amplification for paper-based immunoassays. Lab Chip. Feb. 7, 2015;15(3):655-9.
Chen et al., CRISPR-Cas12a target binding unleashes indiscriminate single-stranded DNase activity. Science. Apr. 27, 2018;360(6387):436-439. doi: 10.1126/science.aar6245. Epub Feb. 15, 2018. Erratum in: Science. Feb. 19, 2021;371(6531).
He et al., Fabrication of paper-based microfluidic analysis devices: a review. RSC Advances. 2015; 5: 78109-27.

(Continued)

*Primary Examiner* — Anoop K Singh
(74) *Attorney, Agent, or Firm* — Wolf, Greenfield & Sacks, P.C.

(57) ABSTRACT

Disclosed herein are hydrogels comprising a polynucleotide-based structural component. Methods of altering a property of a hydrogel based on user-defined nucleic acid input sequences are also disclosed. In addition, various applications are described that utilize these hydrogels and methods.

5 Claims, 56 Drawing Sheets

Specification includes a Sequence Listing.

(56) References Cited

OTHER PUBLICATIONS

Heitzer et al., Circulating tumor DNA as a liquid biopsy for cancer. Clin Chem. Jan. 2015;61(1):112-23. doi: 10.1373/clinchem.2014. 222679. Epub Nov. 11, 2014.

Li et al., CRISPR-Cas12a has both cis- and trans-cleavage activities on single-stranded DNA. Cell Res. Apr. 2018;28(4):491-493. doi: 10.1038/s41422-018-0022-x. Epub Mar. 12, 2018.

Magro et al., Paper-based RNA detection and multiplexed analysis for Ebola virus diagnostics. Sci Rep. May 2, 2017;7(1):1347.

Na et al., Rapid molecular diagnosis of infectious viruses in microfluidics using DNA hydrogel formation. Biosens Bioelectron. Jun. 15, 2018;108:9-13. doi: 10.1016/j.bios.2018.02.040. Epub Feb. 19, 2018.

Pardee et al., Paper-based synthetic gene networks. Cell. Nov. 6, 2014;159(4):940-54. doi: 10.1016/j.cell.2014.10.004. Epub Oct. 23, 2014.

Pardee et al., Rapid, Low-Cost Detection of Zika Virus Using Programmable Biomolecular Components. Cell. May 19, 2016;165(5):1255-1266. doi: 10.1016/j.cell.2016.04.059. Epub May 6, 2016.

Previtera et al., Preparation of DNA-crosslinked polyacrylamide hydrogels. J Vis Exp. Aug. 27, 2014;(90):51323.

Sicilia et al., Programmable polymer-DNA hydrogels with dual input and multiscale responses. Biomater Sci. Feb. 23, 2014;2(2):203-211. doi: 10.1039/c3bm60126a. Epub Oct. 2013.

Barker et al., Biodegradable DNA-enabled poly(ethylene glycol) hydrogels prepared by copper-free click chemistry. J Biomater Sci Polym Ed. 2016;27(1):22-39. doi: 10.1080/09205063.2015. 1103590. Epub Nov. 6, 2015.

Cangialosi et al., DNA sequence-directed shape change of photopatterned hydrogels via high-degree swelling. Science 357 1126-9. 2017.

Chang et al., Homogeneous Entropy Catalytic-Driven DNA Hydrogel as Strong Signal Blocker for Highly Sensitive Electrochemical Detection of Platelet-Derived Growth Factor. Anal Chem. Jul. 3, 2018;90(13):8241-8247. doi: 10.1021/acs.analchem.8b01766. Epub Jun. 13, 2018.

Fu et al., Controlled reagent transport in disposable 2D paper networks. Lab Chip. Apr. 7, 2010;10(7):918-20. doi: 10.1039/b919614e. Epub Jan. 15, 2010.

Gao et al., Swelling Dynamics of a DNA-Polymer Hybrid Hydrogel Prepared Using Polyethylene Glycol as a Porogen. Gels. Nov. 18, 2015;1(2):219-234.

Gjorevski et al., Designer matrices for intestinal stem cell and organoid culture. Nature. Nov. 24, 2016;539(7630):560-564. doi: 10.1038/nature20168. Epub Nov. 16, 2016.

Gootenberg et al., Nucleic acid detection with CRISPR-Cas13a/C2c2. Science. Apr. 28, 2017;356(6336):438-442. doi: 10.1126/science.aam9321. Epub Apr. 13, 2017.

Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.

Hajian et al., Detection of unamplified target genes via CRISPR-Cas9 immobilized on a graphene field-effect transistor. Nat Biomed Eng. 2019; 3: 427-37.

Kahn et al., Integration of Switchable DNA-Based Hydrogels with Surfaces by the Hybridization Chain Reaction. Nano Lett. Nov. 11, 2015;15(11):7773-8. doi: 10.1021/acs.nanolett.5b04101. Epub Oct. 27, 2015.

Kleinstiver et al., Genome-wide specificities of CRISPR-Cas Cpf1 nucleases in human cells. Nat Biotechnol. Aug. 2016;34(8):869-74. doi: 10.1038/nbt.3620. Epub Jun. 27, 2016.

Knott et al., CRISPR-Cas guides the future of genetic engineering. Science. Aug. 31, 2018;361(6405):866-869.

Li et al., Endonuclease-responsive aptamer-functionalized hydrogel coating for sequential catch and release of cancer cells. Biomaterials. Jan. 2013;34(2):460-9. doi: 10.1016/j.biomaterials.2012.09. 040. Epub Oct. 17, 2012.

Lin et al., Mechanical properties of a reversible, DNA-crosslinked polyacrylamide hydrogel. J Biomech Eng. Feb. 2004;126(1):104-10.

Lu et al., A graphene platform for sensing biomolecules. Angew Chem Int Ed Engl. 2009;48(26):4785-7.

Ma et al., Remote controlling DNA hydrogel by magnetic field. Appl Mater Interfaces. 2017; 9: 1995-2000.

Manohar et al., Peeling single-stranded DNA from graphite surface to determine oligonucleotide binding energy by force spectroscopy. Nano Lett. Dec. 2008;8(12):4365-72.

Martino et al., Growth factors engineered for super-affinity to the extracellular matrix enhance tissue healing. Science. Feb. 21, 2014; 343: 885-888.

Okolie et al., Development of a heptaplex PCR assay for identification of Staphylococcus aureus and CONS with simultaneous detection of virulence and antibiotic resistance genes. BMC Microbiol. Aug. 5, 2015;15:157.

Pawlyta et al., Raman microspectroscopy characterization of carbon blacks: spectral analysis and structural information. Carbon. 2015; 84: 479-90.

Purcell et al., Injectable and bioresponsive hydrogels for on-demand matrix metalloproteinase inhibition. Nat Mater. Jun. 2014;13(6):653-61. doi: 10.1038/nmat3922. Epub Mar. 30, 2014.

Qureshi et al., The role of the Staphylococcal VraTSR regulatory system on vancomycin resistance and vanA operon expression in vancomycin-resistant Staphylococcus aureus. PLoS One. Jan. 15, 2014;9(1):e85873.

Rosales et al., The design of reversible hydrogels to capture extracellular matrix dynamics. Nat Rev Mater. 2016;1:15012. doi: 10.1038/natrevmats.2015.12. Epub Feb. 2, 2016.

Stephan et al., Biopolymer implants enhance the efficacy of adoptive T-cell therapy. Nat Biotechnol. Jan. 2015;33(1):97-101. doi: 10.1038/nbt.3104. Epub Dec. 15, 2014.

Venkatesh et al., Nucleic acid therapeutic carriers with on-demand triggered release. Bioconjug Chem. Sep. 2009;20(9):1773-82.

Wang et al., Computational study of DNA-cross-linked hydrogel formation for drug delivery applications. Macromolecules. 2018; 51: 9758-68.

Wei et al., Target-responsive DNA hydrogel mediated "stop-flow" microfluidic paper-based analytic device for rapid, portable and visual detection of multiple targets. Anal Chem. Apr. 21, 2015;87(8):4275-82. doi: 10.1021/acs.analchem.5b00532. Epub Apr. 2, 2015.

Xing et al., Self-assembled DNA hydrogels with designable thermal and enzymatic responsiveness. Adv Mater. Mar. 4, 2011;23(9):1117-21. doi: 10.1002/adma.201003343. Epub Dec. 22, 2010.

Yang et al., Engineering target-responsive hydrogels based on aptamer-target interactions. J Am Chem Soc. May 21, 2008;130(20):6320-1. doi: 10.1021/ja801339w. Epub Apr. 29, 2008.

Cai et al., An electrochemical impedance biosensor for Hg2+ detection based on DNA hydrogel by coupling with DNAzyme-assisted target recycling and hybridization chain reaction. Biosens Bioelectron. Dec. 15, 2017;98:466-472. doi: 10.1016/j.bios.2017. 07.025. Epub Jul. 11, 2017.

Gao et al., Toehold of dsDNA exchange affects the hydrogel swelling kinetics of a polymer-dsDNA hybrid hydrogel. Soft Matter. 7:1741-6.

Li et al., Designing hydrogels for controlled drug delivery. Nat Rev Mater. Dec. 2016;1(12):16071. doi: 10.1038/natrevmats.2016.71. Epub Oct. 18, 2016.

Liu et al., DNA adsorbed on graphene and graphene oxide: fundamental interactions, desorption and applications. CurrO pin Coll Inter Science. 2016; 26:41-9.

Mao et al., Deterministic encapsulation of single cells in thin tunable microgels for niche modelling and therapeutic delivery. Nat Mater. Feb. 2017;16(2):236-243. doi: 10.1038/nmat4781. Epub Oct. 31, 2016.

Qin et al., Bioinspired Hydrogel Interferometer for Adaptive Coloration and Chemical Sensing. Adv Mater. May 2018;30(21):e1800468. doi: 10.1002/adma.201800468. Epub Apr. 11, 2018.

Wei et al., Capture and release of protein by a reversible DNA-induced sol-gel transition system. Angew Chem Int Ed Engl. 2008;47(2):331-3.

(56) References Cited

OTHER PUBLICATIONS

Zhu et al., An aptamer cross-linked hydrogel as a colorimetric platform for visual detection. Angew Chem Int Ed Engl. Feb. 1, 2010;49(6):1052-6.

* cited by examiner

MRSA1 crRNA Sequence:
GGGTAATTTCTACTAAGTGTAGATTTAAAGAAGATGGTATGTGG

MRSA2 crRNA Sequence:
GGGTAATTTCTACTAAGTGTAGATATTTTGTTAAAGAAGATGGT

MRSA3 crRNA Sequence:
GGGTAATTTCTACTAAGTGTAGATACAAAATTAAATTGAACGTT

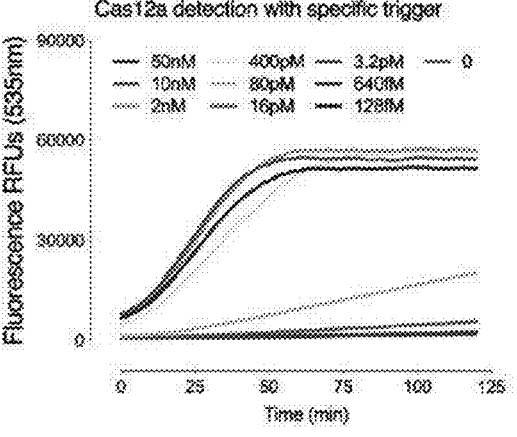
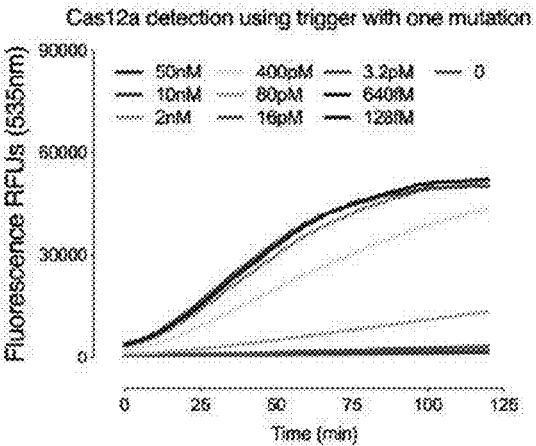
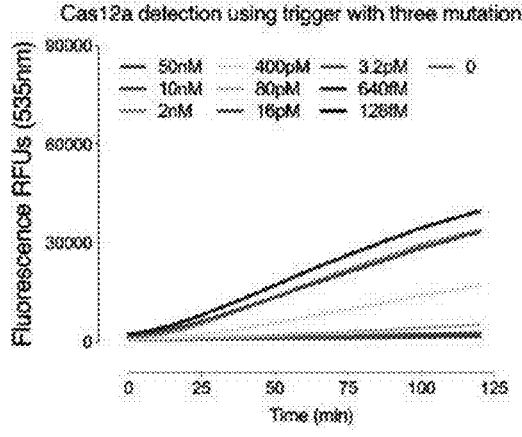
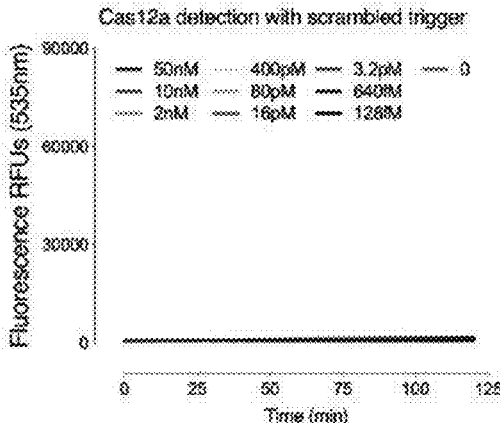
FIG. 6

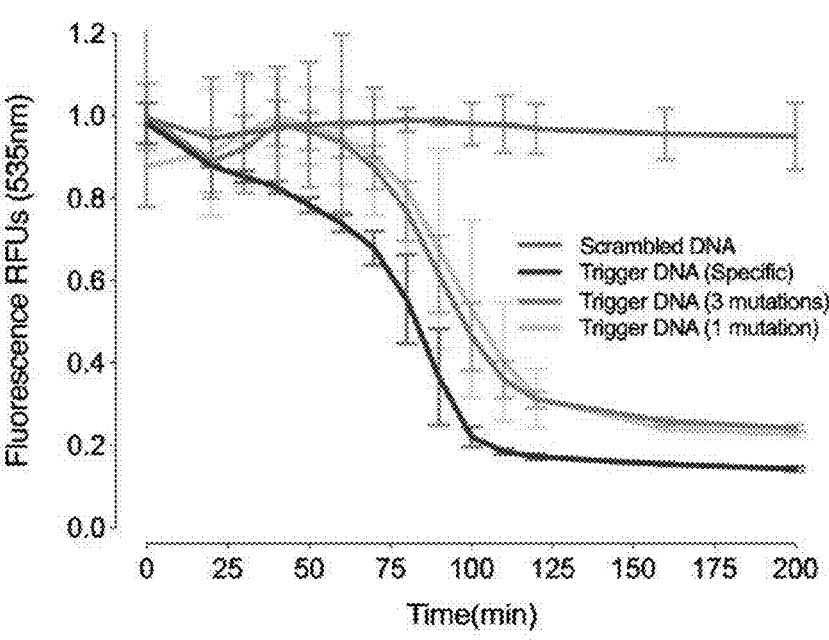
FIG. 9
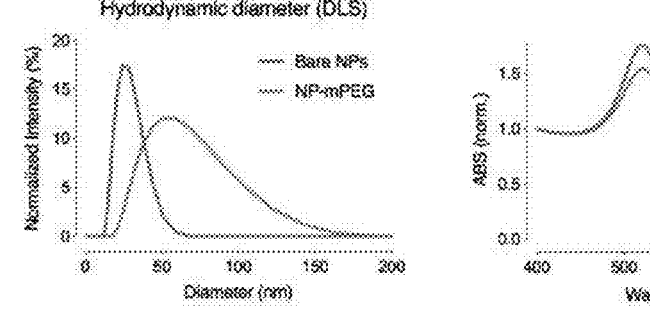 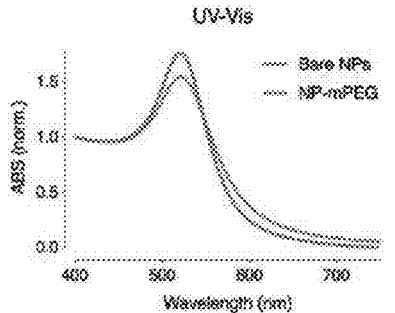 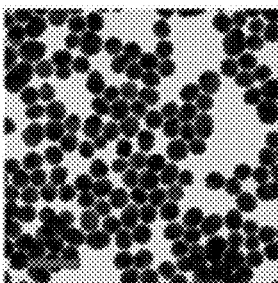
FIG. 10

Representative µPAD Flow for the detection of
MRSA1 dsDNA Trigger (nM)

Modulation of Cas12a activity
through gel properties

Kendall τ > 0.99
2-sided p = 0.005

Protection of anchors from Cas12a
by oligo hybridization

Bulk Cas12a-mediated gel degradation

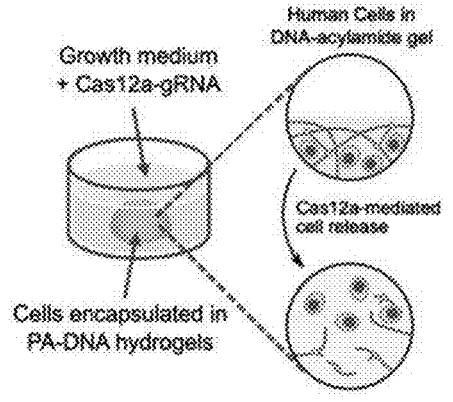
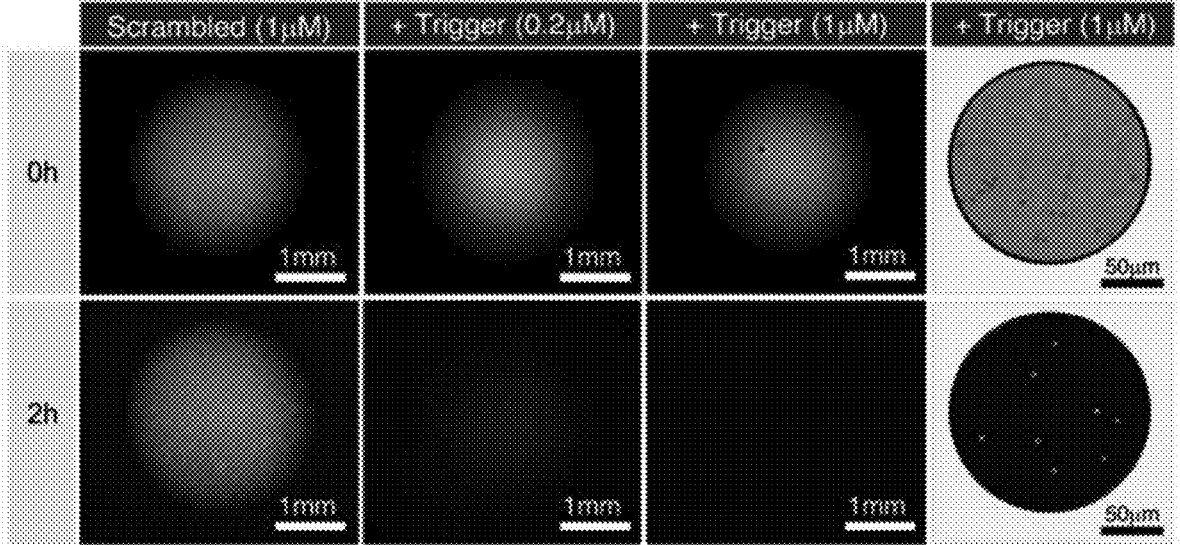
FIG. 18E
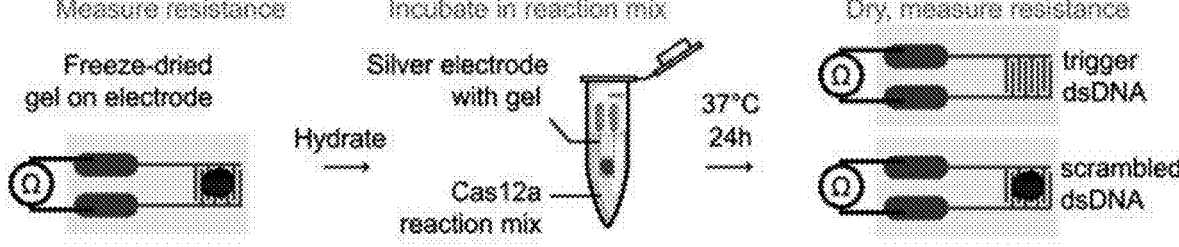
FIG. 19A

Replicates 1-5

Images of electrodes
after reaction 2.5mm

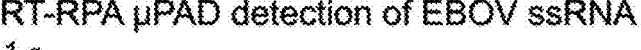
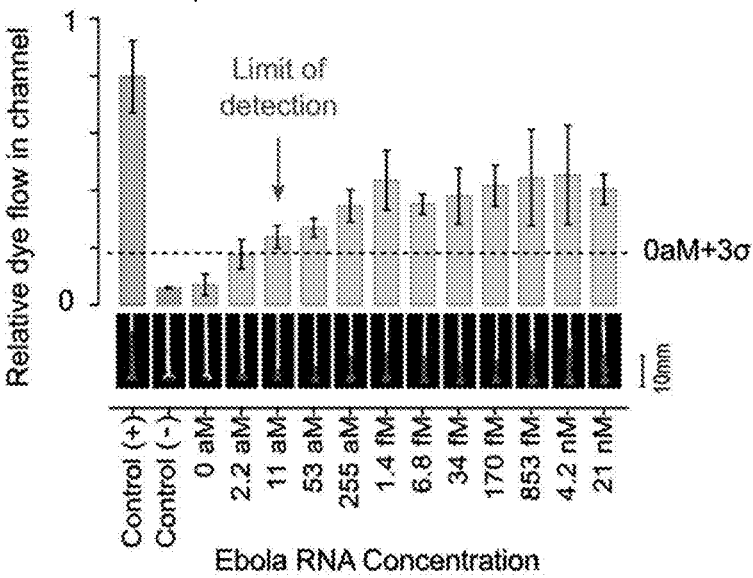
FIG. 20B
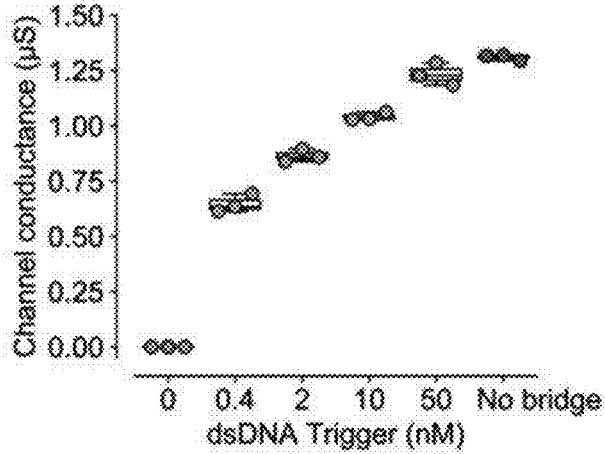
FIG. 20C

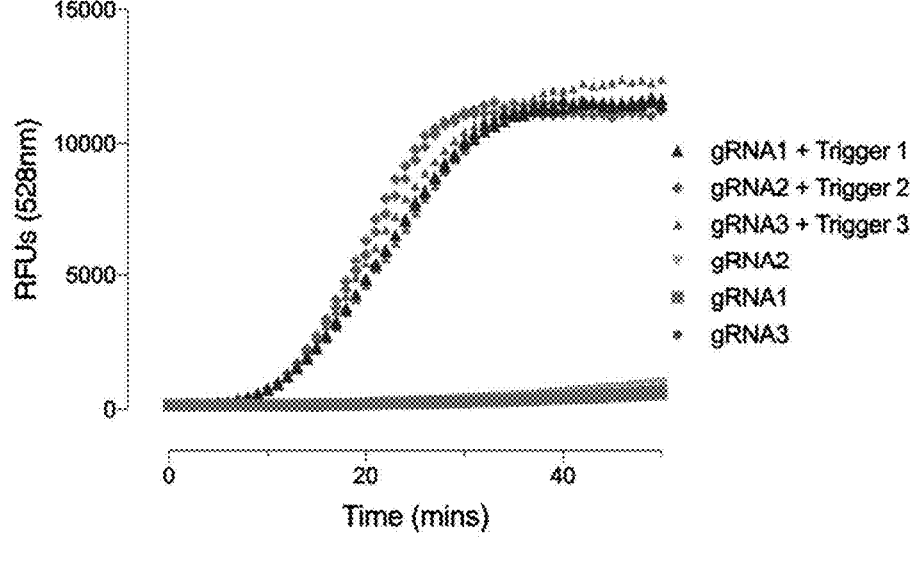
FIG. 22
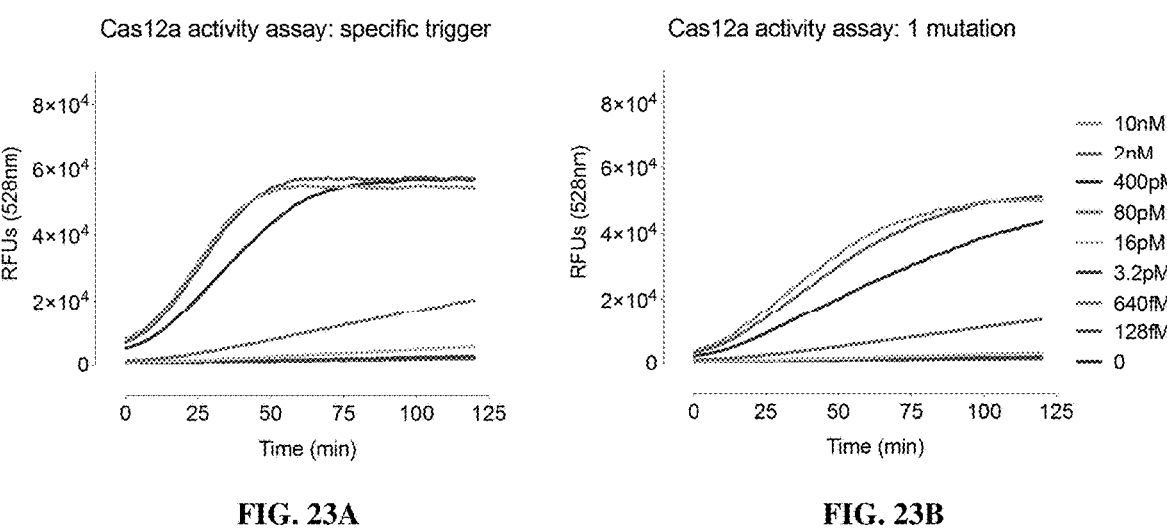
FIG. 23A                    FIG. 23B

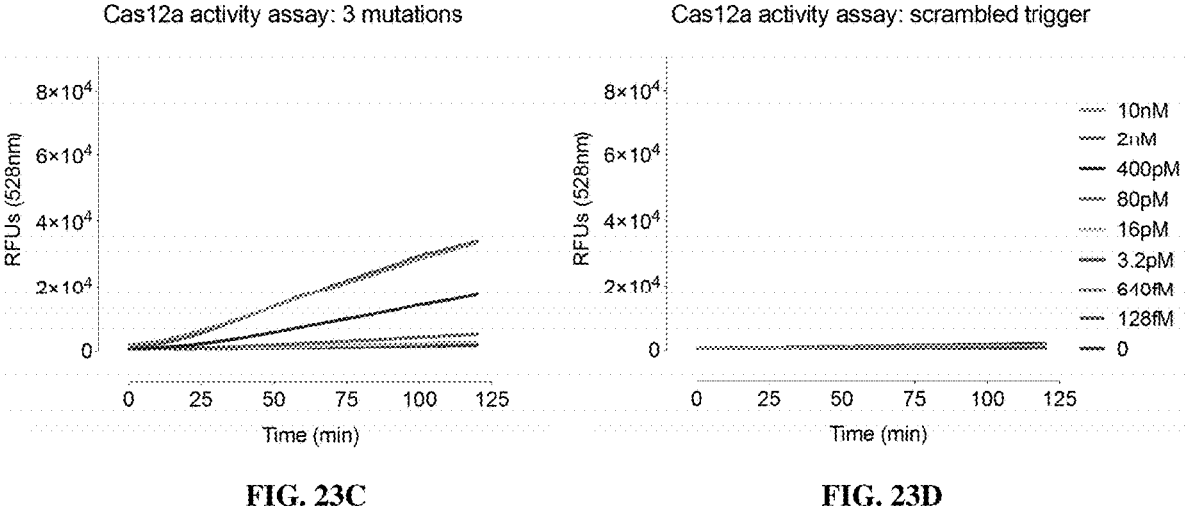
FIG. 23C
FIG. 23D
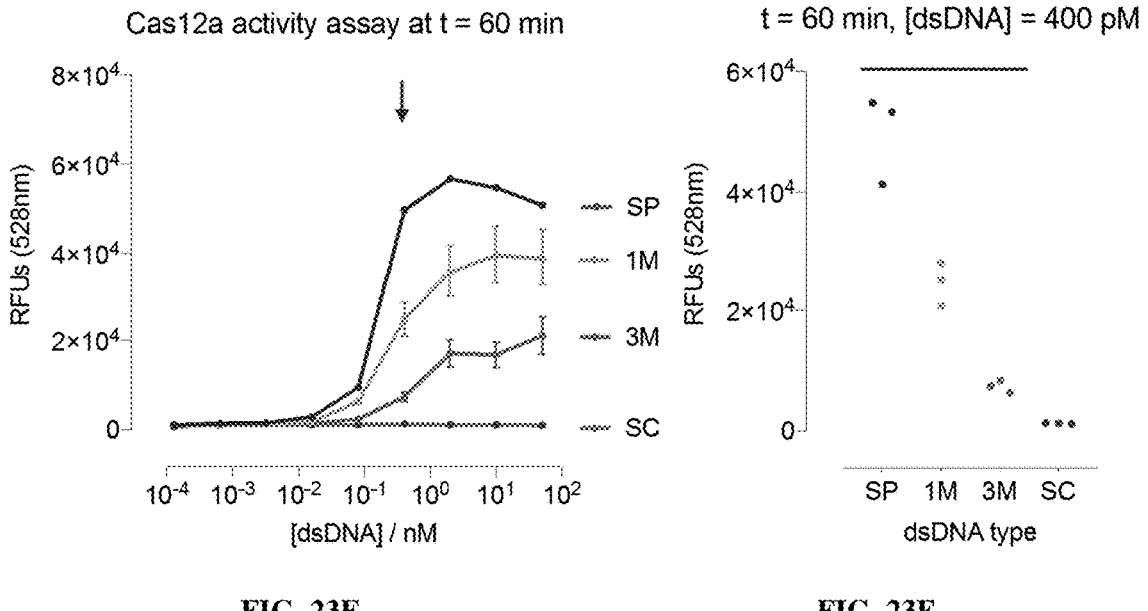
FIG. 23E
FIG. 23F

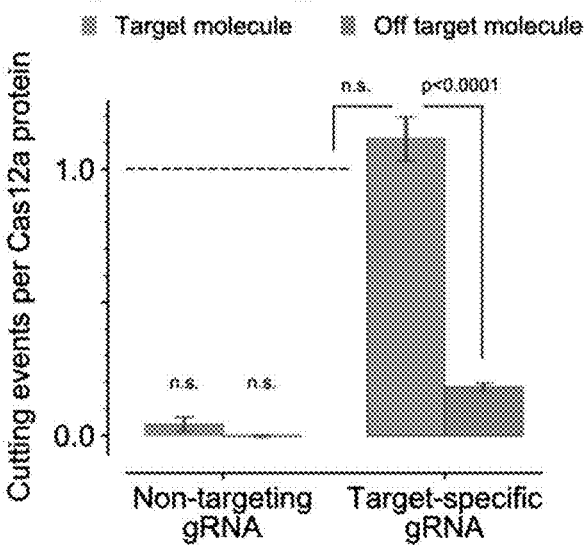
FIG. 24
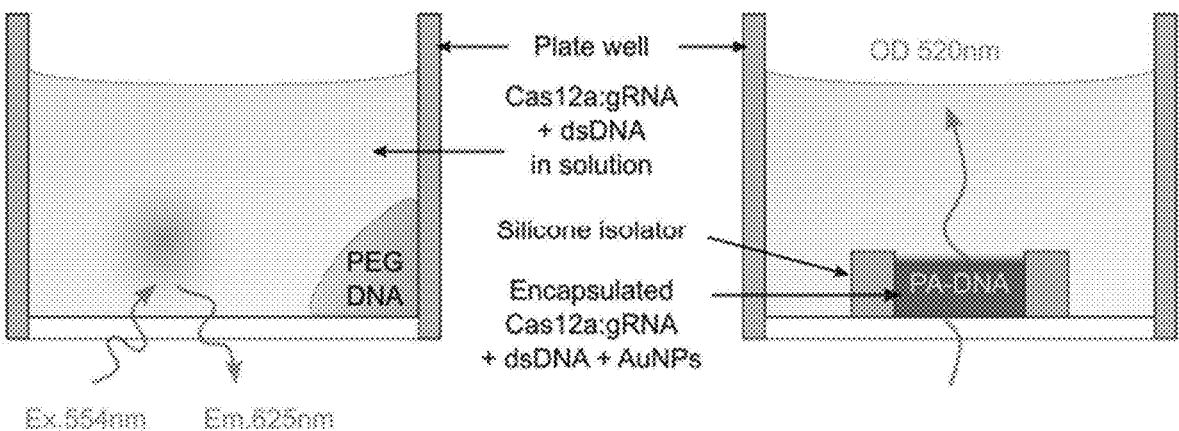
FIG. 25A                    FIG. 25B

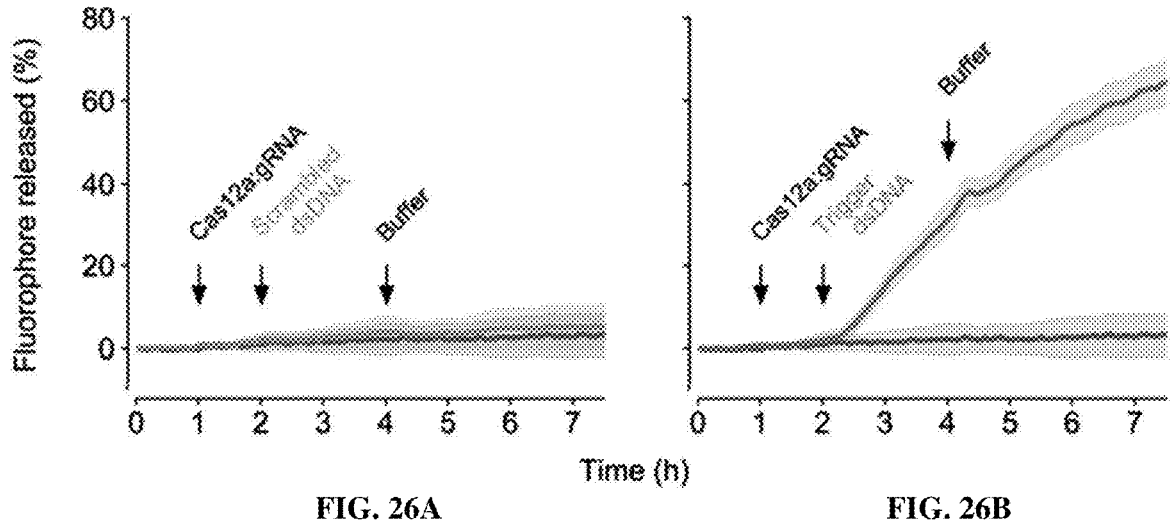
FIG. 26A
FIG. 26B
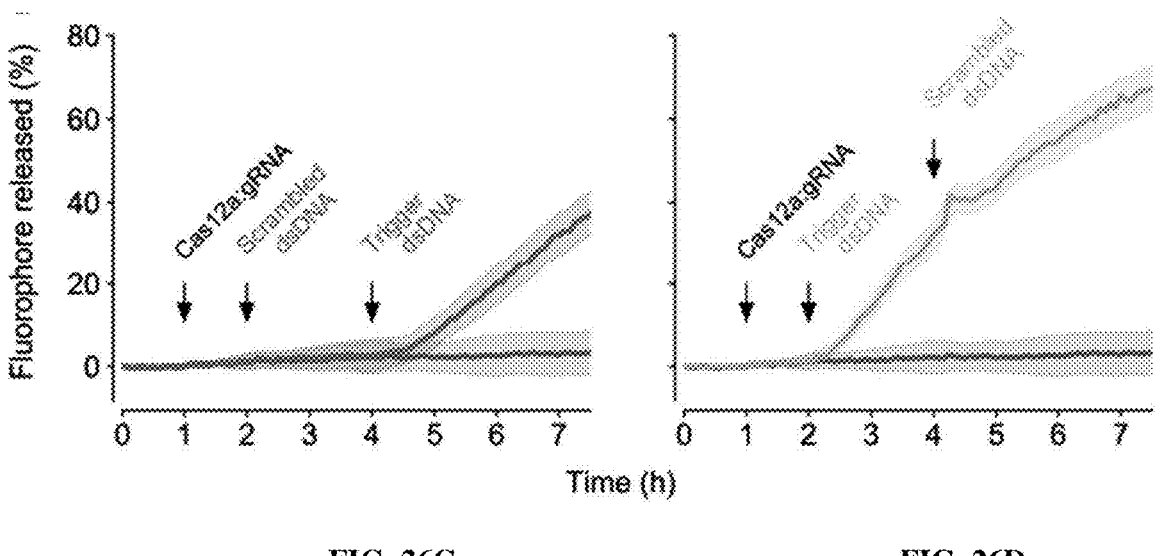
FIG. 26C
FIG. 26D

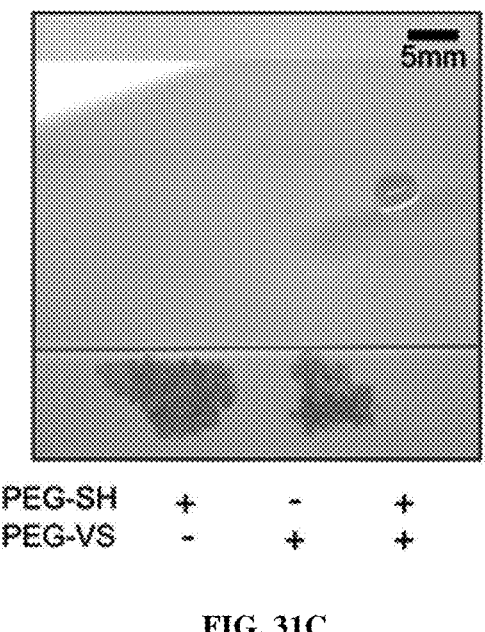
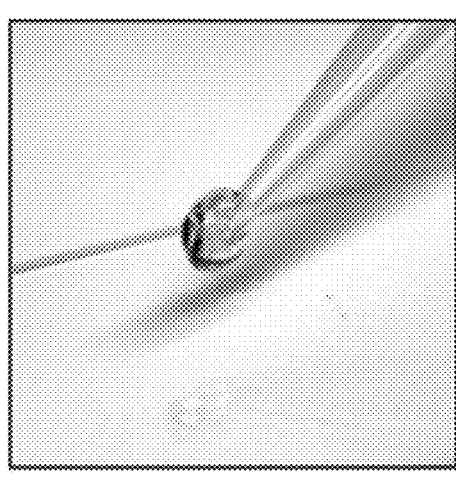
PEG-SH    +    -    +
PEG-VS    -    +    +
FIG. 31C                    FIG. 31D
Modulation of Cas12a activity by gel properties
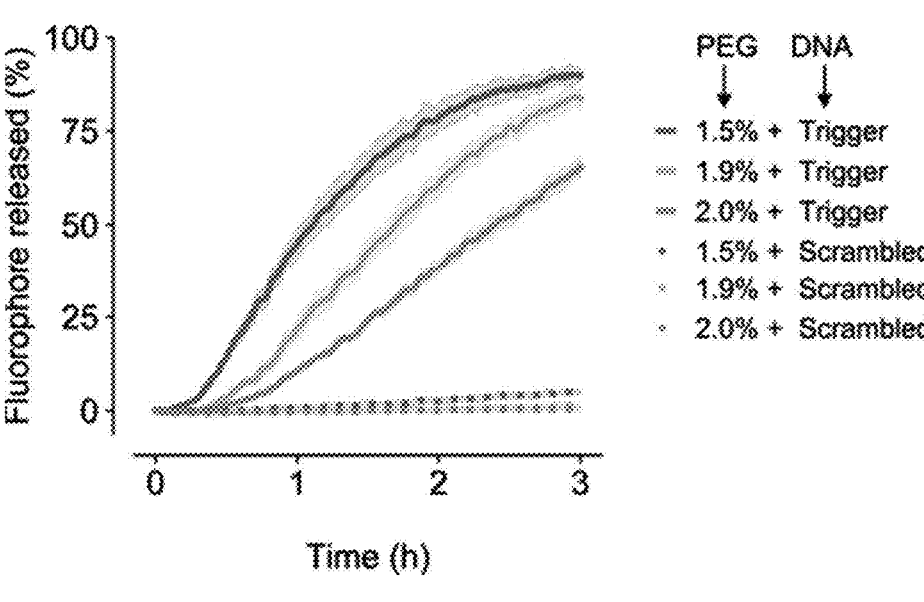
FIG. 32

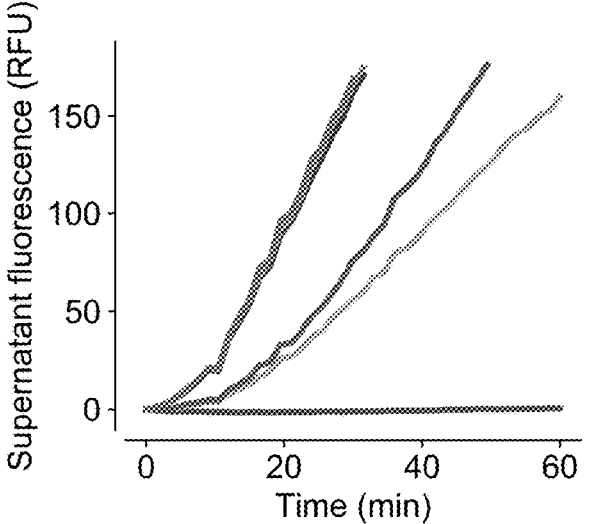
FIG. 33
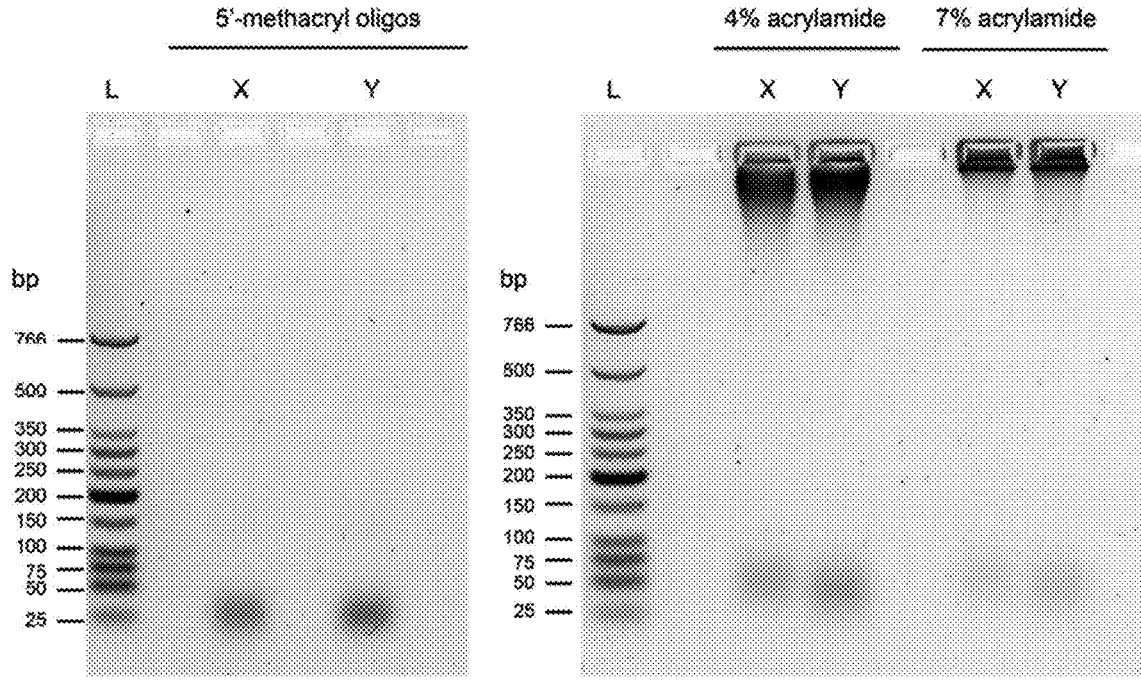
FIG. 34A                         FIG. 34B

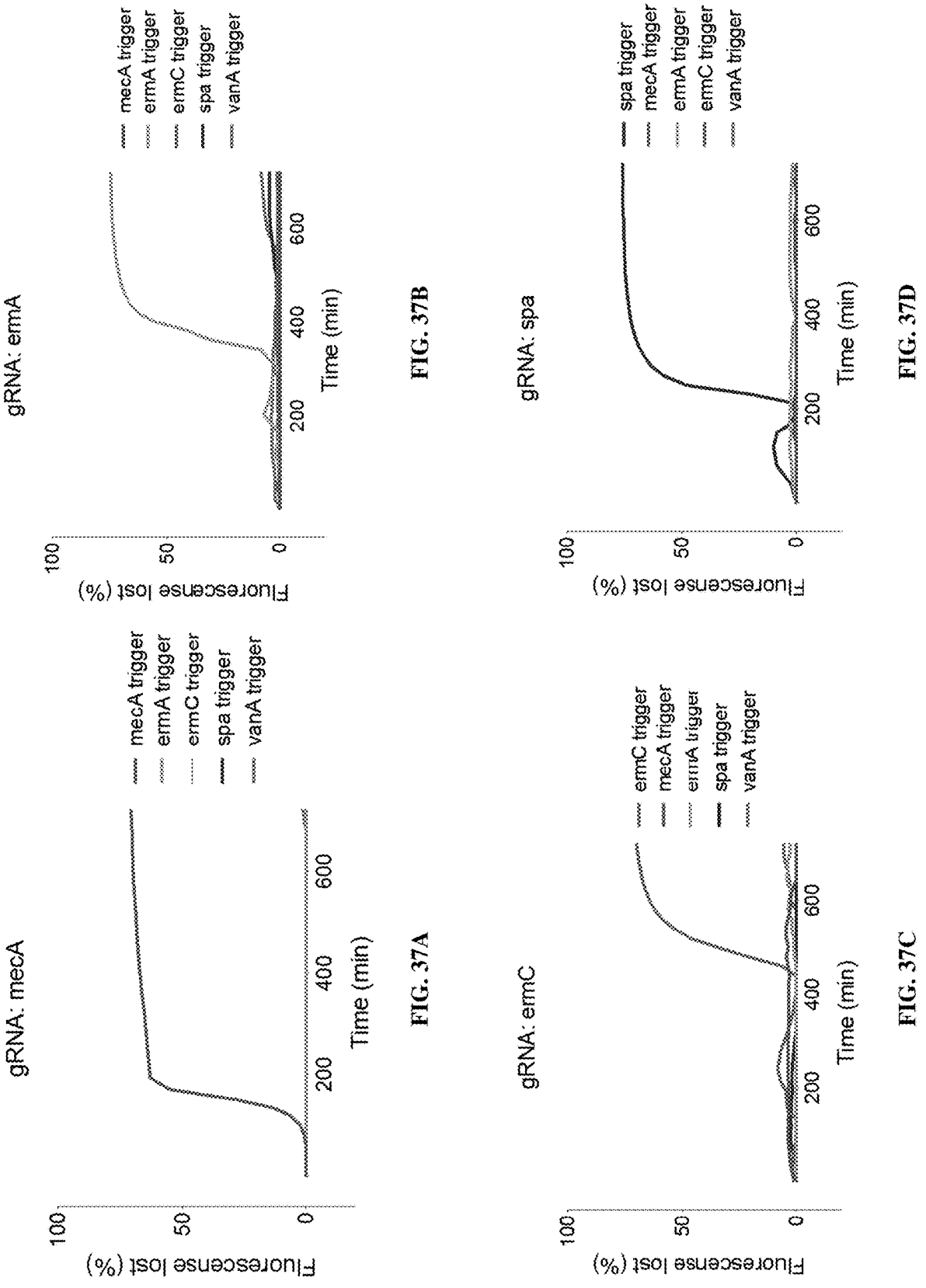

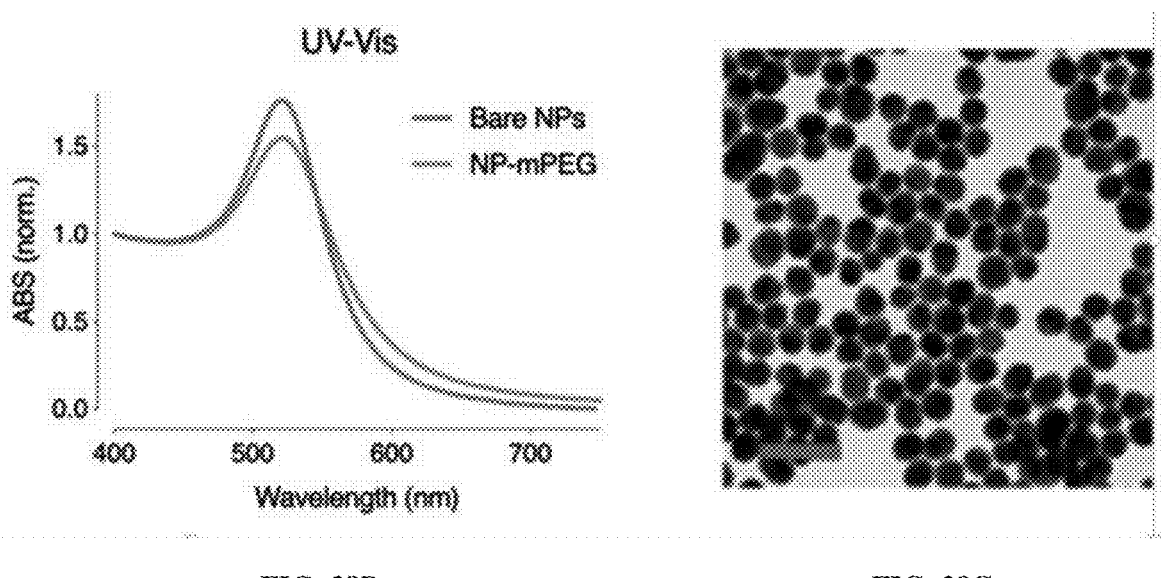
FIG. 38B                                                      FIG. 38C
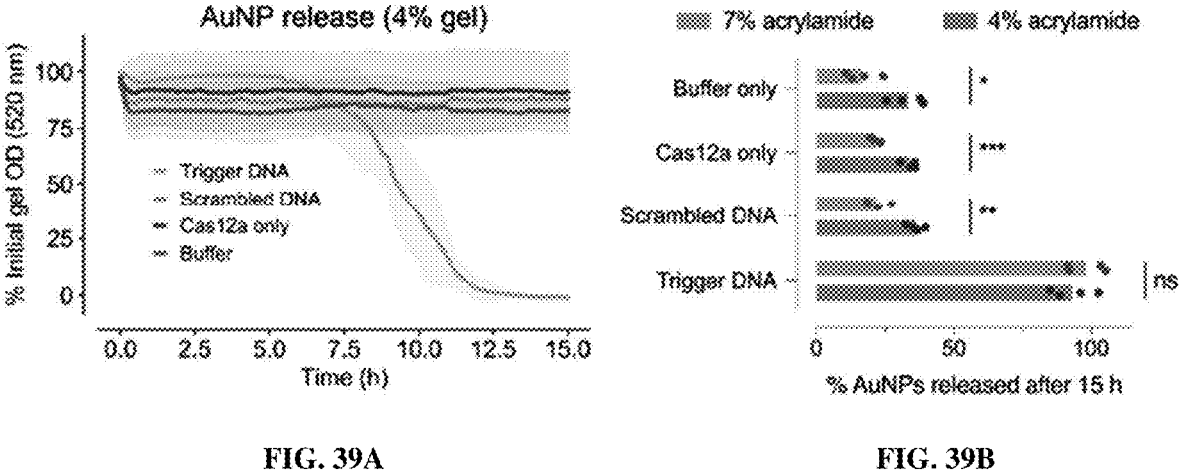
FIG. 39A                                                      FIG. 39B C    4% Acrylamide D    7% Acrylamide

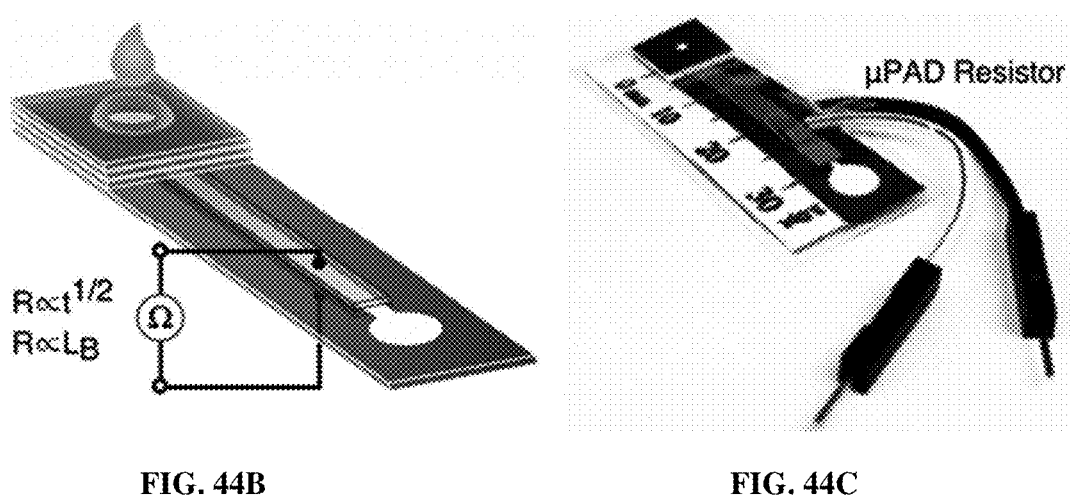
FIG. 44B                    FIG. 44C
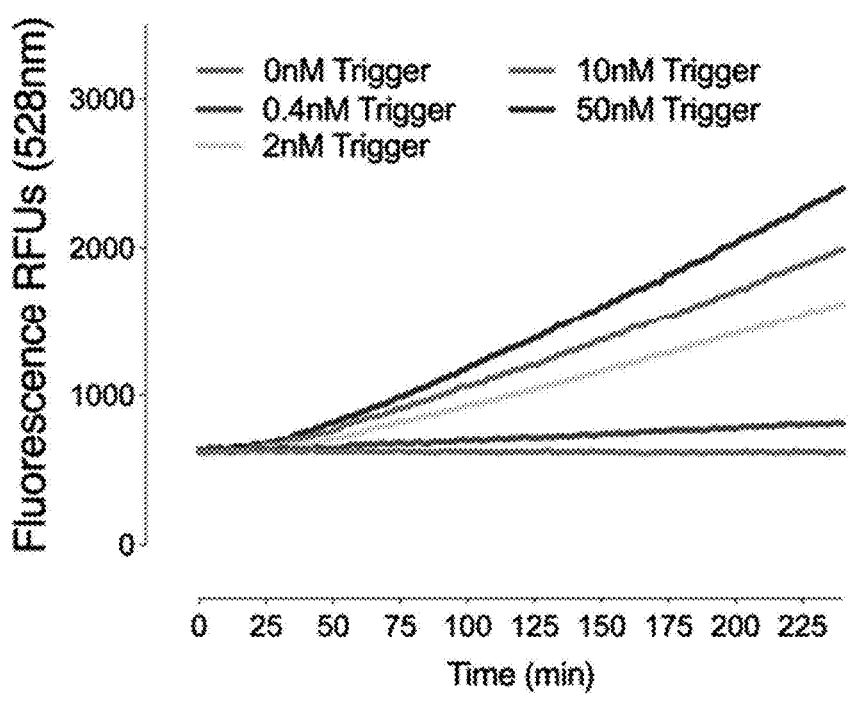
FIG. 45

Representative µPAD Flow for the detection of MRSA1 dsDNA Trigger (nM)

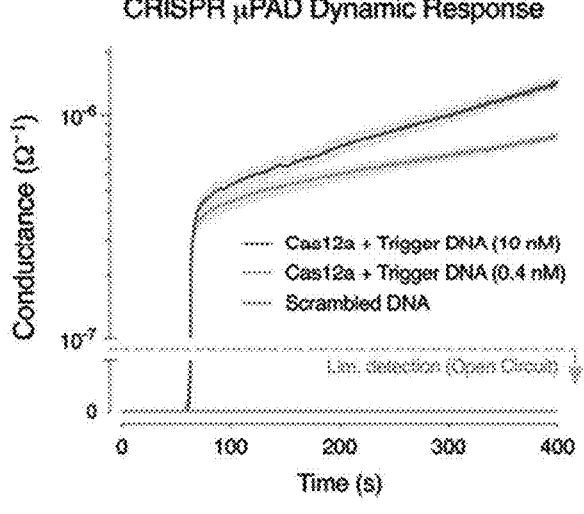
FIG. 48A
FIG. 48B
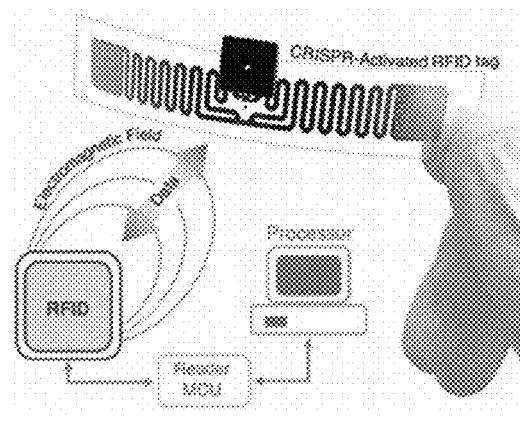
FIG. 48C
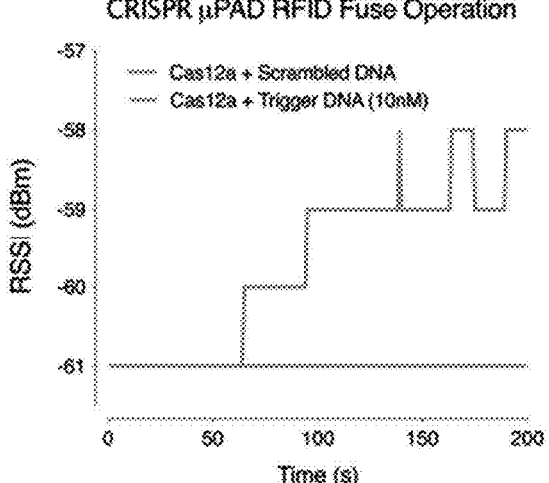
FIG. 48D

DNA-RESPONSIVE HYDROGELS

RELATED APPLICATIONS

This application claims the benefit under 35 U.S.C. § 119(e) of U.S. provisional application No. 62/823,272, filed Mar. 25, 2019, and U.S. provisional application No. 62/889,234, filed Aug. 20, 2019, the entirety of each of which is incorporated herein by reference.

GOVERNMENT SUPPORT

This invention was made with Government support under Grant Nos. HDTRA1-15-1-0040 and HDTRA1-15-1-0051 awarded by the Defense Threat Reduction Agency (DTRA). The Government has certain rights in the invention.

FIELD

Disclosed herein are hydrogels comprising a polynucleotide-based structural component. Methods of altering a property of a hydrogel based on user-defined nucleic acid input sequences are also disclosed. In addition, various applications are described that utilize these hydrogels and methods.

INCORPORATION BY REFERENCE

The instant application contains a Sequence Listing which has been submitted in ASCII format via EFS-Web and is hereby incorporated by reference in its entirety. Said ASCII copy, created on Oct. 31, 2022, is named M065670465US02-SUBSEQ-CRP and is 9,874 bytes in size.

BACKGROUND

Smart materials, whose physicochemical properties can be modulated in response to external stimuli, are increasingly important for numerous biotechnology applications, including the fabrication of scaffolds for tissue engineering (6), the actuation of microfluidic valves (7), and the sensing of small molecule in diagnostic devices (8, 9). Recent advances in low-cost DNA synthesis have made DNA-based materials increasingly attractive. DNA-responsive hydrogels are well suited to interface with synthetic DNA constructs or naturally-occurring extracellular DNA (10). Current DNA-responsive hydrogels typically rely on toehold strand-displacement or hairpin formation (11, 12), which require high concentrations of DNA triggers for actuation. Adapting these DNA-hydrogels for activation with new trigger sequences usually involves extensive hydrogel redesign and optimization, limiting the programmability of these systems. Thus, the development of sensitive hydrogels capable of generating various types of outputs in response to specific, user-defined nucleic acid input sequences could significantly augment the applicability of these platforms.

SUMMARY

The use of CRISPR system components for effecting multiscale, programmable changes in the physical properties of macroscopic materials such as hydrogels remains unexplored. As disclosed herein, CRISPR system components were used to control the properties of DNA-based hydrogels. Different hydrogels were engineered to demonstrate a variety of responses for use in therapeutic, diagnostic and sensing applications, including the release of small molecules, nanoparticles (NPs), and live cells, as well as for the modulation of bulk electrical and permeability properties of DNA-hydrogels (FIG. 1).

Accordingly, in some aspects, the disclosure relates to methods of altering a property of a hydrogel. In some embodiments, the method comprises contacting the hydrogel with a CRISPR component, wherein: (i) the hydrogel comprises a plurality of structural components, wherein one or more structural component is a nucleic acid molecule component comprising a polynucleotide sequence of at least 5 nucleotides; (ii) the CRISPR component comprises at least one guide RNA; and (iii) the polynucleotide sequence of at least one nucleic acid molecule component in (i) is cleaved when contacted with the CRISPR component of (ii), thereby altering a property of the hydrogel.

In some embodiments, two or more structural components are nucleic acid molecule components comprising a polynucleotide sequence of at least 5 nucleotides. In some embodiments, at least two of the two or more nucleic acid molecule components comprise different polynucleotide sequences.

In some embodiments, at least one nucleic acid molecule component comprises a double-stranded polynucleotide sequence. In some embodiments, at least one nucleic acid molecule component comprises a single-stranded polynucleotide sequence.

In some embodiments, at least one nucleic acid molecule component comprises the polynucleotide sequence of a protospacer adjacent motif (PAM). In some embodiments, at least one nucleic acid molecule component lacks the polynucleotide sequence of a PAM.

In some embodiments, a nucleic acid molecule component of the hydrogel further comprises a monomer species selected from the group consisting of an ethylene glycol monomer and an acrylamide monomer. In some embodiments, a nucleic acid molecule component of the hydrogel further comprises polyethylene glycol, polyacrylamide, gelatin, a fibrillar protein, or a combination thereof.

In some embodiments, one or more structural component of the hydrogel is selected from the group consisting of a carbon black nanoparticle, a carbon nanocone, a carbon nanofiber, a carbon nanoscroll, a carbon nanothread, a diamondoid, a nanodiamond, a single-walled carbon nanohorn, a carbon nanotube, graphene, graphene oxide, and fullerene.

In some embodiments, at least one guide RNA of the CRISPR component comprises a spacer region that is at least 75% complementary to a polynucleotide sequence of one or more nucleic acid molecule component of the hydrogel. In some embodiments, at least one guide RNA of the CRISPR component comprises a spacer region that is at least 75% complementary to a polynucleotide sequence of a trigger molecule. In some embodiments, the method further comprises contacting the CRISPR component with the trigger molecule.

In some embodiments, one or more CRISPR protein of the CRISPR component comprises RNA-guided dsDNA endonuclease activity. In some embodiments, the CRISPR protein is Cas9, Cas12a, C2c1, C2c2, or C2c3. In some embodiments, the CRISPR protein also comprises ssDNA endonuclease activity. In some embodiments, the CRISPR protein is Cas12a.

In other aspects, the disclosure relates to methods of releasing a product of interest from a hydrogel. In some embodiments, the method comprises altering a property of the hydrogel according to a method described herein, thereby releasing the product of interest from the hydrogel.

In some embodiments, the product of interest is a molecule that is anchored to the hydrogel. In some embodiments, the product of interest is encapsulated by the hydrogel. In some embodiments, the product of interest is selected from the group consisting of a molecule, a nanoparticle, and a live cell.

In other aspects, the disclosure relates to methods of modulating the flow of a product of interest through a hydrogel. In some embodiments the method comprises, altering a property of the hydrogel according to a method described herein, thereby modulating the flow of the product of interest through the hydrogel.

In some embodiments, the product of interest is an electric signal. In some embodiments, the method further comprises detecting the electric signal.

In some embodiments, the product of interest is a solution. In some embodiments, the solution conducts an electric current. In some embodiments, the method further comprises detecting an electric signal of the electric current.

In other aspects, the disclosure relates to compositions. In some embodiments, a composition comprises: (i) a hydrogel comprising a plurality of structural components, wherein one or more structural component is a nucleic acid molecule component comprising a polynucleotide sequence of at least 5 nucleotides; and (ii) a CRISPR component comprising: (a) a guide RNA comprising a polynucleotide sequence that complements a polynucleotide sequence of one or more nucleic acid molecule component of the hydrogel, wherein the composition lacks a CRISPR protein corresponding to the guide RNA; (b) a CRISPR protein, wherein the composition lacks a guide RNA comprising a polynucleotide sequence that complements a polynucleotide sequence of one or more nucleic acid molecule component of the hydrogel; (c) a trigger molecule, wherein the composition lacks a guide RNA comprising a polynucleotide sequence that complements the polynucleotide sequence of the trigger molecule; or (d) a guide RNA comprising a polynucleotide sequence that complements a polynucleotide sequence of one or more nucleic acid molecule component of the hydrogel and a CRISPR protein, wherein the composition lacks a trigger molecule.

In some embodiments, two or more structural components of the hydrogel in (i) are nucleic acid molecule components. In some embodiments, at least two of the two or more nucleic acid molecule components comprise different polynucleotide sequences.

In some embodiments, at least one nucleic acid molecule component of the hydrogel in (i) comprises a double-stranded polynucleotide sequence. In some embodiments, at least one nucleic acid molecule component of the hydrogel in (i) comprises a single-stranded polynucleotide sequence.

In some embodiments, at least one nucleic acid molecule component of the hydrogel in (i) comprises the polynucleotide sequence of a protospacer adjacent motif (PAM). In some embodiments, at least one nucleic acid molecule component of the hydrogel in (i) lacks the polynucleotide sequence of a PAM.

In some embodiments, at least one nucleic acid molecule component of the hydrogel in (i) further comprises at least one monomer species selected from the group consisting of an ethylene glycol monomer and an acrylamide monomer. In some embodiments, at least one nucleic acid molecule component of the hydrogel in (i) further comprises polyethylene glycol, polyacrylamide, gelatin, a fibrillar protein, or a combination thereof.

In some embodiments, one or more structural component of the hydrogel in (i) is selected from the group consisting of a carbon black nanoparticle, a carbon nanocone, a carbon nanofiber, a carbon nanoscroll, a carbon nanothread, a diamondoid, a nanodiamond, a single-walled carbon nanohorn, a carbon nanotube, graphene, graphene oxide, and fullerene.

In some embodiments, the CRISPR component comprises a guide RNA. In some embodiments, the guide RNA comprises a spacer region that is at least 75% complementary to a polynucleotide sequence of one or more nucleic acid molecule component of the hydrogel.

In some embodiments, the CRISPR component comprises a trigger molecule and a guide RNA. In some embodiments, the guide RNA comprises a spacer region that is at least 75% complementary to the polynucleotide sequence of the trigger molecule.

In some embodiments, the CRISPR component comprises a CRISPR protein. In some embodiments, the CRISPR protein comprises a RNA-guided dsDNA endonuclease activity. In some embodiments, the CRISPR protein is Cas9, Cas12a, C2c1, C2c2, or C2c3. In some embodiments, the CRISPR protein also comprises ssDNA endonuclease activity. In some embodiments, the protein is Cas12a.

In some aspects, the disclosure relates to CRISPR-responsive switches. In some embodiments, a CRISPR-responsive switch comprises a composition as described herein.

In some embodiments a CRISPR-responsive switch comprises: (i) a first compartment, wherein the first compartment comprises a composition comprising: (a) a hydrogel comprising a plurality of structural components, wherein one or more structural component is a nucleic acid molecule component comprising a polynucleotide sequence of at least 5 nucleotides; and (b) a CRISPR component comprising a guide RNA comprising a polynucleotide sequence that complements a polynucleotide sequence of one or more nucleic acid molecule component of the hydrogel, wherein the composition lacks a CRISPR protein corresponding to the guide RNA; and (ii) a second compartment, wherein the second compartment comprises a CRISPR protein corresponding to the guide RNA of (i)(b).

In some embodiments a CRISPR-responsive switch comprises: (i) a first compartment, wherein the first compartment comprises a composition comprising: (a) a hydrogel comprising a plurality of structural components, wherein one or more structural component is a nucleic acid molecule component comprising a polynucleotide sequence of at least 5 nucleotides; and (b) a CRISPR component comprising a CRISPR protein, wherein the composition lacks a guide RNA comprising a polynucleotide sequence that complements a polynucleotide sequence of one or more nucleic acid molecule component of the hydrogel of (i)(a); and (ii) a second compartment, wherein the second compartment comprises a guide RNA comprising a polynucleotide sequence that complements a polynucleotide sequence of one or more nucleic acid molecule component of the hydrogel of (i)(a).

In some embodiments a CRISPR-responsive switch comprises: (i) a first compartment, wherein the first compartment comprises a composition comprising: (a) a hydrogel comprising a plurality of structural components, wherein one or more structural component is a nucleic acid molecule component comprising a polynucleotide sequence of at least 5 nucleotides; and (b) a CRISPR component comprising a trigger molecule, wherein the composition lacks a guide RNA comprising a polynucleotide sequence that complements the polynucleotide sequence of the trigger molecule;

(ii) a second compartment, wherein the second compartment comprises a guide RNA that comprises a polynucleotide sequence that complements the polynucleotide sequence of the trigger molecule of (i)(b).

In some embodiments a CRISPR-responsive switch comprises: (i) a first compartment, wherein the first compartment comprises a composition comprising: (a) a hydrogel comprising a plurality of structural components, wherein one or more structural component is a nucleic acid molecule component comprising a polynucleotide sequence of at least 5 nucleotides; and (b) a CRISPR component comprising a guide RNA comprising a polynucleotide sequence that complements a polynucleotide sequence of one or more nucleic acid molecule component of the hydrogel and a CRISPR protein, wherein the composition lacks a trigger molecule; (ii) a second compartment, wherein the second compartment comprises the trigger molecule of (i)(b).

In some embodiments, in the OFF state, the components of the first compartment are not in contact with the components of the second compartment; and wherein, in the ON state, the components of the first compartment are in contact with the components of the second compartment.

In some embodiments, turning the switch from OFF to ON releases a product of interest from the hydrogel. In some embodiments, the product of interest is selected from the group consisting of a molecule, a nanoparticle, and a live cell.

In some embodiments, turning the switch from OFF to ON alters the flow of a product of interest through the hydrogel. In some embodiments, the product of interest is selected from the group consisting of an electric signal and a solution.

In some aspects, the disclosure relates to devices comprising a CRISPR-responsive switch as described herein.

In other aspects the disclosure relates to a hydrogel comprising a plurality of structural components, wherein: (i) three or more structural components of the plurality of structural components of the hydrogel are nucleic acid molecule components comprising at least 5 nucleotides and one or more species of monomers, wherein at least one monomer species is selected from the group consisting of an ethylene glycol monomer and an acrylamide monomer; and (ii) the three or more nucleic acid molecule components in (i) differ in sequence.

In some embodiments, a nucleic acid molecule component of the hydrogel further comprises polyethylene glycol, polyacrylamide, gelatin, a fibrillar protein, or a combination thereof.

In some embodiments, at least one nucleic acid molecule component comprises a double-stranded polynucleotide sequence. In some embodiments, at least one nucleic acid molecule component comprises a single-stranded polynucleotide sequence.

These and other aspects of the invention are further described below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 2A. Specific release of pre-programmed fluorescent cargo molecules anchored to dsDNA linkers in branched PEG-gelatin hydrogels using Cas12a cis-cleavage activity without bulk gel degradation (t=24 h). FIG. 2B. Release of fluorescent cargo molecules anchored to ssDNA linkers in PEG-gelatin hydrogels using non-specific Cas12a trans-cleavage activity without bulk gel degradation. FIG. 2C. Bulk degradation of polyacrylamide (PA)-DNA gels via Cas12a trans-cleavage activity measured by tracking the release of intercalating EVAGREEN® DNA dye into solution. FIG. 2D. Release of PEG-decorated gold nanoparticles (18 nm) from PA-DNA gels using Cas12a trans-cleavage. FIG. 2E. Bulk degradation of PA-DNA gels leading to release of encapsulated K562 human cells with different dsDNA triggers and concentrations. DNA in gels was stained using EVAGREEN®, while cells are dyed using Calcein-AM. Representative images of initial states of PA-DNA hydrogels (t=0 h), as well as its degradation leading to cell release (t=1 h), are also shown.

FIG. 3A. Schematic of the experimental procedure. FIG. 3B. Degradation kinetics of carbon black-DNA gels with increasing concentrations of DNA trigger. Six replicates were visually inspected at 30-minute intervals to detect degradation or detachment of CB-DNA gels from inkjet-printed silver interdigitated electrodes (IDEs). Inset: Representative images of electrodes showing in-tact (top) and detached (bottom) gels after the reaction with Cas12a. FIG. 3C. Electrical resistance across IDEs bridged by CB-DNA hydrogel droplets, before and after digestion by activated Cas12a-crRNA at two different timepoints with different dsDNA triggers and concentrations.

FIG. 4A. Schematic of stackable μPAD design (29) modified for operation with CRISPR-gels and electrical readout. Layers 1 to 4 of the μPAD contain circular hydrophilic regions (d=1.5 mm), while layer 5 contains a 1.5×30 mm lateral flow channel. Layer 3 contains 0.5 μL of freeze-dried oligo-functionalized acrylamide polymer (Ps-X & Ps-Y). Layer 4 contains 0.5 μL of freeze-dried color dye in PBS buffer (1:5). The lateral flow channel in layer 5 was covered with conductive tape to measure channel electrical resistance as a function of buffer wicking distance. In the presence of target trigger, the pre-incubation reaction with Cas12a leads to cleavage of the DNA linker, preventing hydrogel crosslinking in the channel and enabling flow. SEM images of paper regions with (top) and without (bottom) crosslinked hydrogel. FIG. 4B. Real-time measurement of electrical resistance of μPAD lateral flow channel for three different concentrations of dsDNA MRSA triggers deposited after 4-hour pre-digestion. FIG. 4C. Endpoint measurements (t=5 minutes) of electrical conductance for different concentrations of dsDNA MRSA trigger deposited after 4-hour pre-digestion of 100 μM ssDNA linker in a PA-DNA μPAD system containing 4% polyacrylamide. FIG. 4D. Schematic of the paper-fluidic device with RFID tag integration to enable remote sensing of dsDNA trigger. FIG. 4E. Internal detail of μPAD section used as a fluidic fuse for the RFID tag. FIG. 4F. Representative signal of the CRISPR-μPAD RFID sensor in the presence and absence of dsDNA MRSA trigger.

```
                                        (SEQ ID NO: 17)
GGGTAATTTCTACTAAGTGTAGATTTAAAGAAGATGGTATGTGGG;

(SEQ ID NO: 18)
GGGTAATTTCTACTAAGTGTAGATATTTTGTTAAAGAAGATGGT;

(SEQ ID NO: 19)
GGGTAATTTCTACTAAGTGTAGATACAAAATTAAATTGAACGTT.
```

FIG. 6. In-solution validation of Cas12a-based detection system for MecA. (A) Fluorescence time-course results for MRSA1 crRNA Cas12a trans-cleavage assays with decreasing concentrations of a specific dsDNA trigger in solution. Similar assays were then performed using dsDNA trigger sequences with one (B) and three (C) nucleotide mismatches for the same range of trigger concentrations as in (A). As the number of nucleotide mismatches between the trigger and the crRNA increased, the rate of ssDNA trans-cleavage decreased. (D) No signal was observed when a completely scrambled trigger sequence was tested. The reactions in (A)-(D) contained 50 nM Cas12a, 62.5 nM MRSA1 crRNA, 750 nM quenched fluorescently labeled ssDNA reporter and the specified concentrations of dsDNA triggers.

Figure 7:
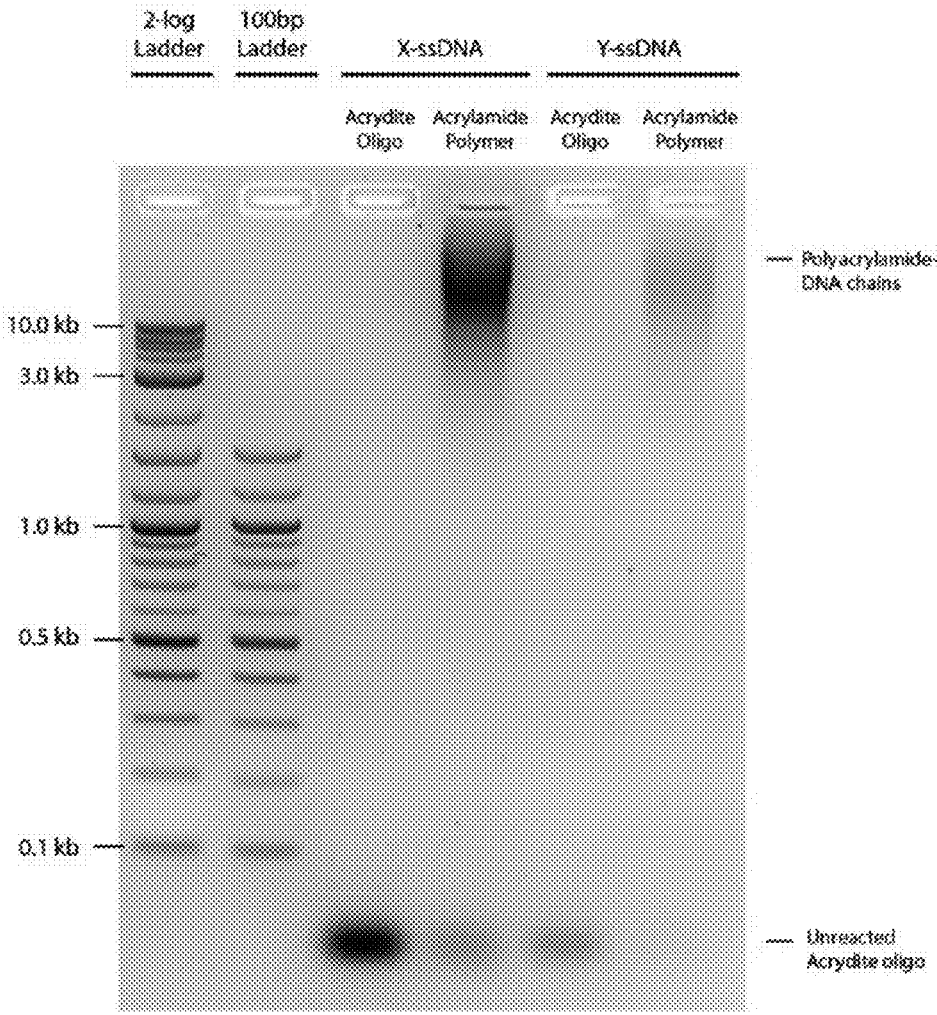

FIG. 7. Incorporation of Acrydite™ oligos into high molecular weight acrylamide polymers. An agarose gel was used to compare the size of ssDNA Acrydite™ oligos X and Y (Lanes 3 and 5) with the product of an APS-catalyzed polymerization reaction containing 4% acrylamide and ssDNA Acrydite™ oligos X and Y (Lanes 4 & 6). The significant increase in apparent size after polymerization with acrylamide indicates incorporation of Acrydite™ oligos into polyacrylamide chains of varying lengths (appearing as a wide band above the 10.0 kb marker). Variations in band intensity are likely due to the effects of ssDNA secondary structure on SYBR Safe fluorescence.

Figure 8:
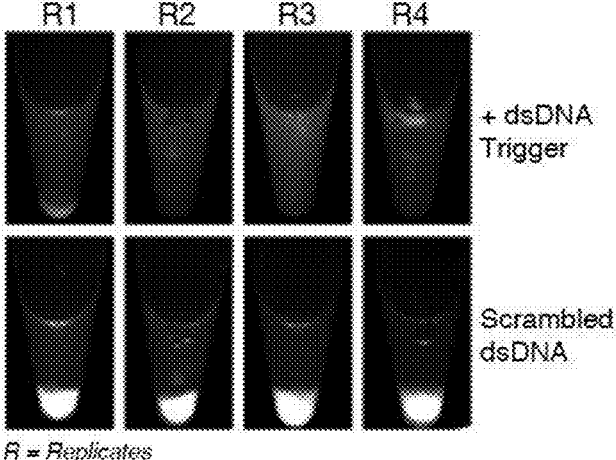

FIG. 8. Degradation of large-scale Acrylamide-DNA gels by embedded Cas12a-crRNA. Activation of Cas12a-crRNA with a dsDNA trigger embedded in acrylamide gels resulted in the degradation of the gel and the release of FITC-dextran into the supernatant (top row, n=4). In contrast, gels embedded with Cas12a-crRNA and a scrambled dsDNA sequence did not degrade, and FITC-dextran remained in the intact gels (bottom row, n=4). The gels were incubated for 18 h at 37° C., inverted once and imaged under UV light. The final concentrations of Cas12a and dsDNA trigger or control dsDNA in the reaction (including the supernatant) were 10 nM and 100 nM, respectively.

FIG. 9. PA-DNA Hydrogel degradation with mismatched sequences. Cas12a detection specificity was tested for whole-gel degradation reactions using EVAGREEN® (Biotium Inc., Fremont, CA) as an intercalating dye. Specific, perfectly matched dsDNA trigger degraded the gel more efficiently than dsDNA crRNA-Cas12a triggers that contained one or three mismatched bases. A nonspecific dsDNA trigger did not activate crRNA-Cas 12a, and the gel did not degrade.

FIG. 10. Characterization of nanoparticles encapsulated in PA-DNA hydrogels (A) Dynamic light scattering, (B) ultraviolet-visible spectroscopy and (C) transmission electronic microscopy (TEM) characterization of gold nanoparticles (NPs) before (blue) and after (orange) mPEG conjugation. Synthesized bare NPs were 18.4±2.2 nm in diameter, as measured by TEM (N=988). The position of the surface plasmon resonance peak of the NPs (521 nm) did not change after conjugation with mPEG, indicating that the NPs did not aggregate. Upon mPEG conjugation, the hydrodynamic diameter of NPs increased (as synthesized $D_H$=24 nm; after mPEG conjugation $D_H$=50 nm), confirming the attachment of high molecular weight mPEG (N=3). Scale bar is 50 nm.

Figure 11:
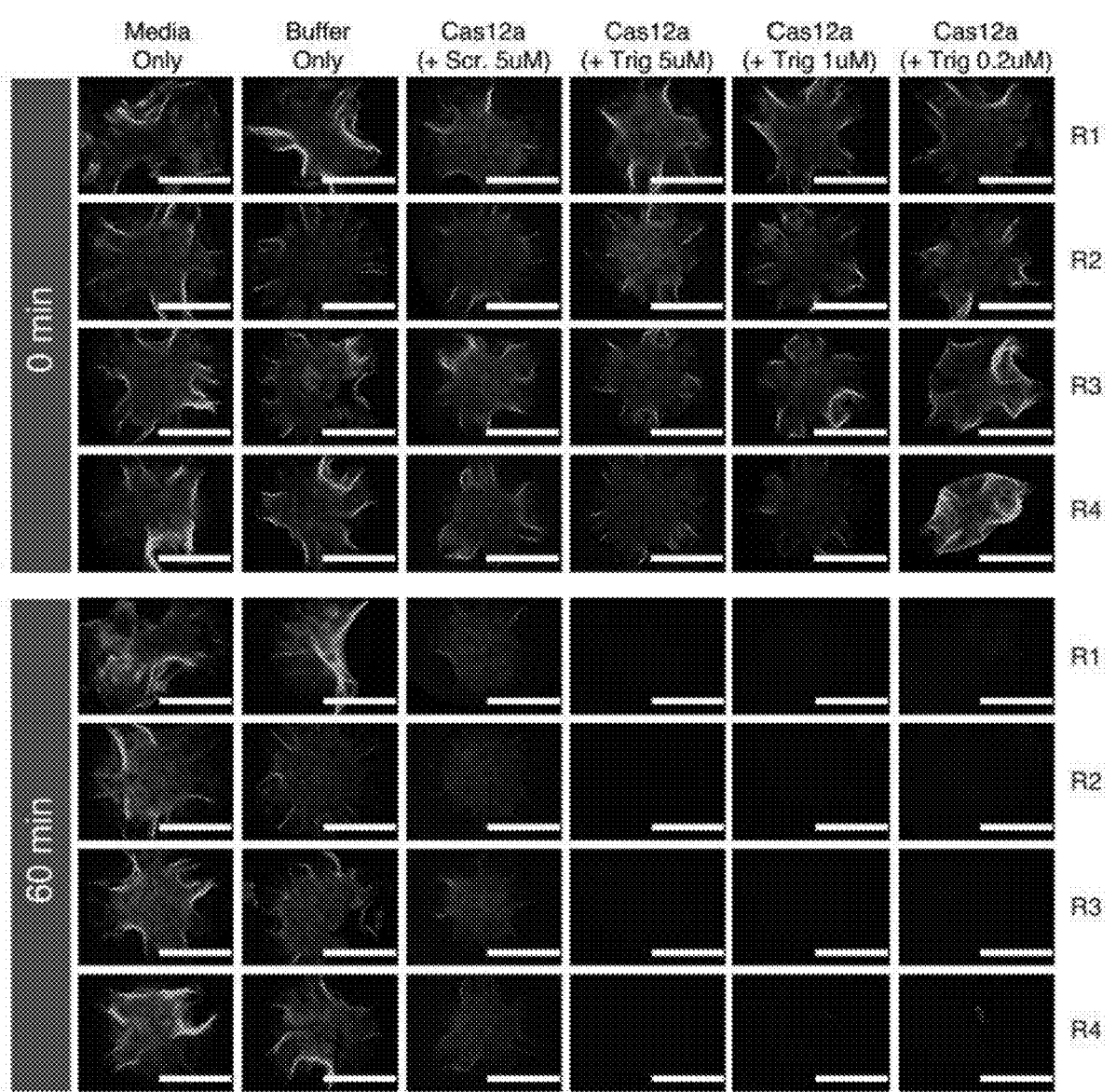

FIG. 11. Cell release from PA-DNA hydrogels. K562 cells were encapsulated into PA-DNA hydrogels for 15 min at 37° C. in R10 medium. Replicates (n=4) for six different solution conditions are shown before and after a 60 min incubation period. Gel disintegration is visible after 60 min in all the incubation conditions that include a specific dsDNA trigger. Little to no degradation was observed in OMEM medium, Cas12a buffer and scrambled dsDNA trigger controls (specific trigger), inactive Cas12a (crRNA-Cas12a with specific trigger) and media-only solutions. Released cells are visible in magnified versions of images from degraded gels similar to that shown in FIG. 2E. Scale bars are 2 mm.

Figure 12A:
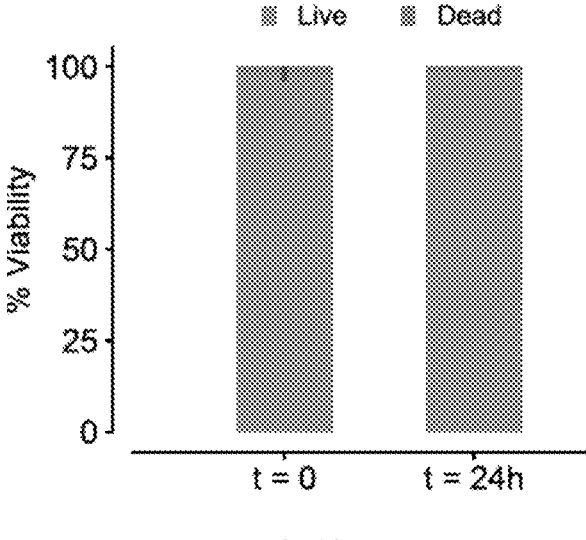
Figure 12B:
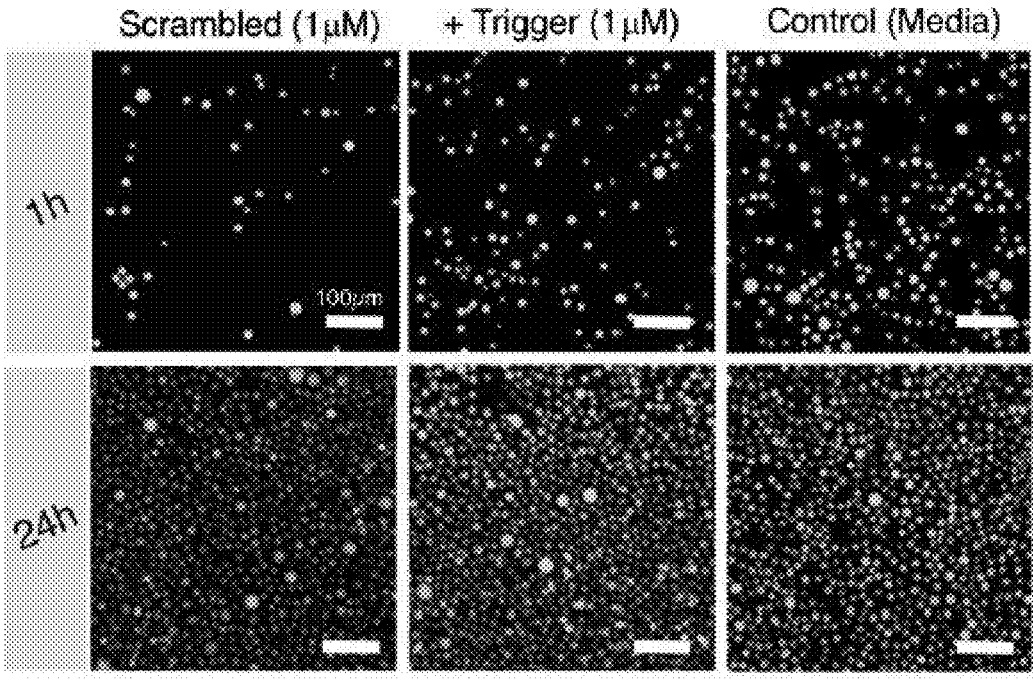

FIGS. 12A-12B. Cell viability in Cas12a solution. FIG. 12A A quantification of the viability of K562 cell colonies before and after 24 h incubation in Cas12a solution. Cell viability studies were conducted in triplicate. FIG. 12B. Representative imaging of K562 cells showing live (green) and dead (red) cells after 1 h and 24 h incubation in active Cas12a (crRNA-Cas12a with specific trigger), inactive Cas12a (crRNA-Cas12a with nonspecific trigger) and media-only solutions. Scale bar is 100 μm.

Figure 13A:
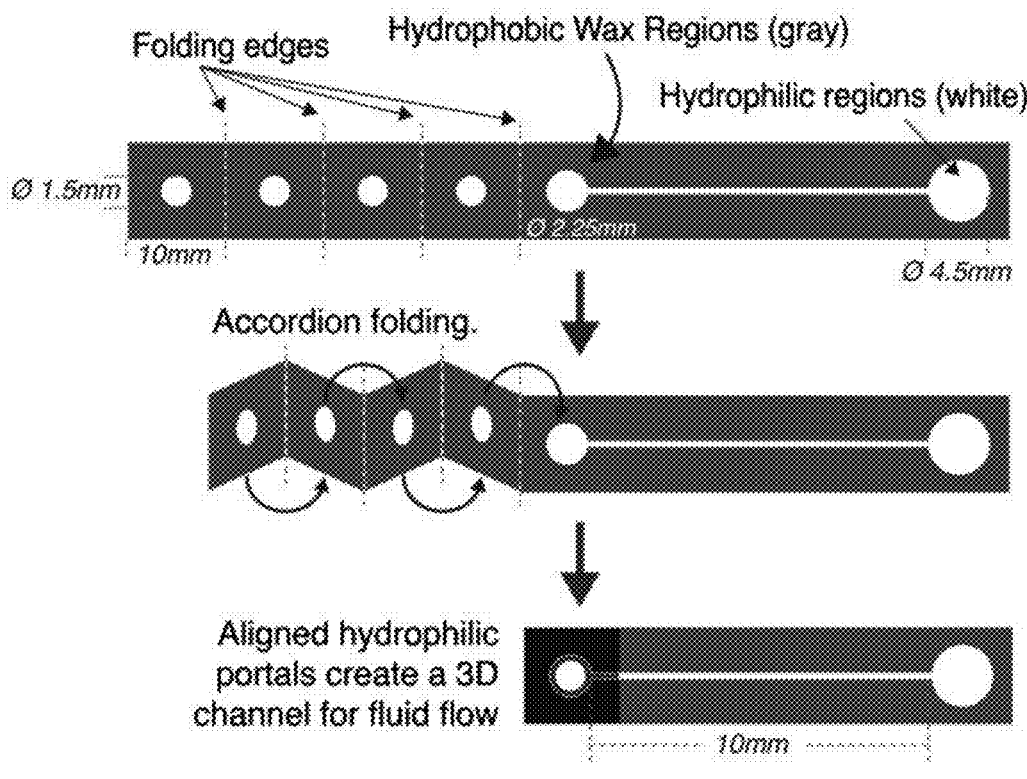
Figure 13B:
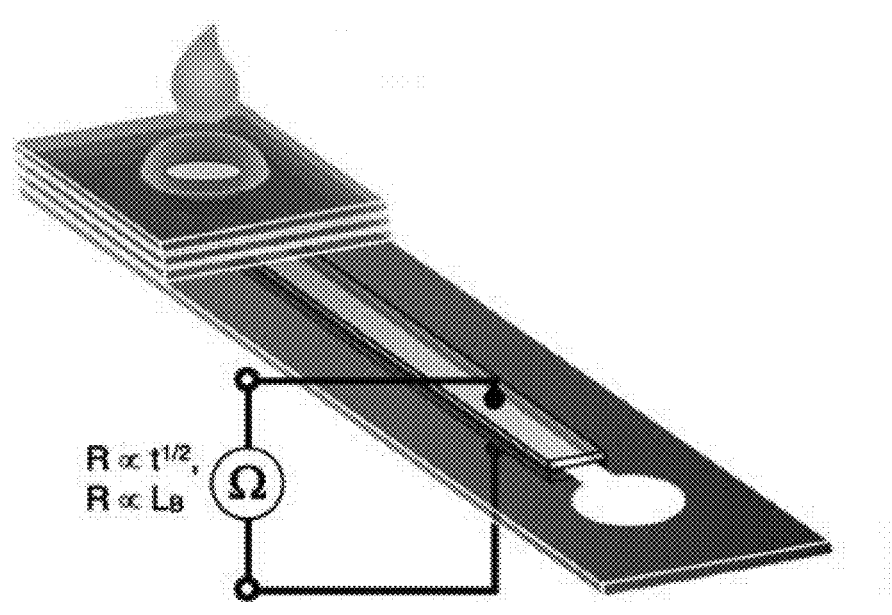
Figure 13C:
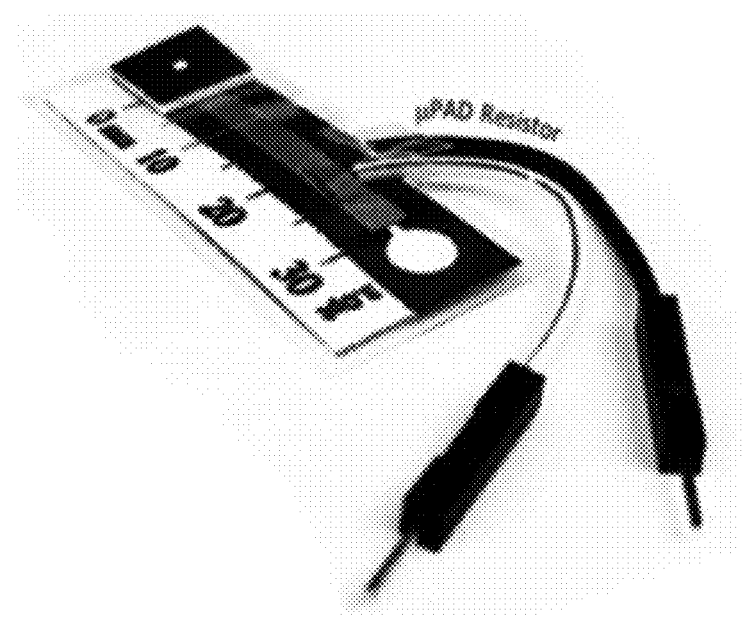

FIGS. 13A-13C. PA-DNA hydrogel resistor μPAD format and device. FIG. 13A. Dimensional details of a single μPAD wax inkjet printing pattern. The folding process outlined was performed once the different components had been added to their respective layers. FIG. 13B. An assembly and testing schematic for electrical resistance measurements of the Cas12a-mediated permeability assay in the μPAD. FIG. 13C. Photograph of assembled μPAD used for Cas12a-mediated permeability testing.

Figure 14:
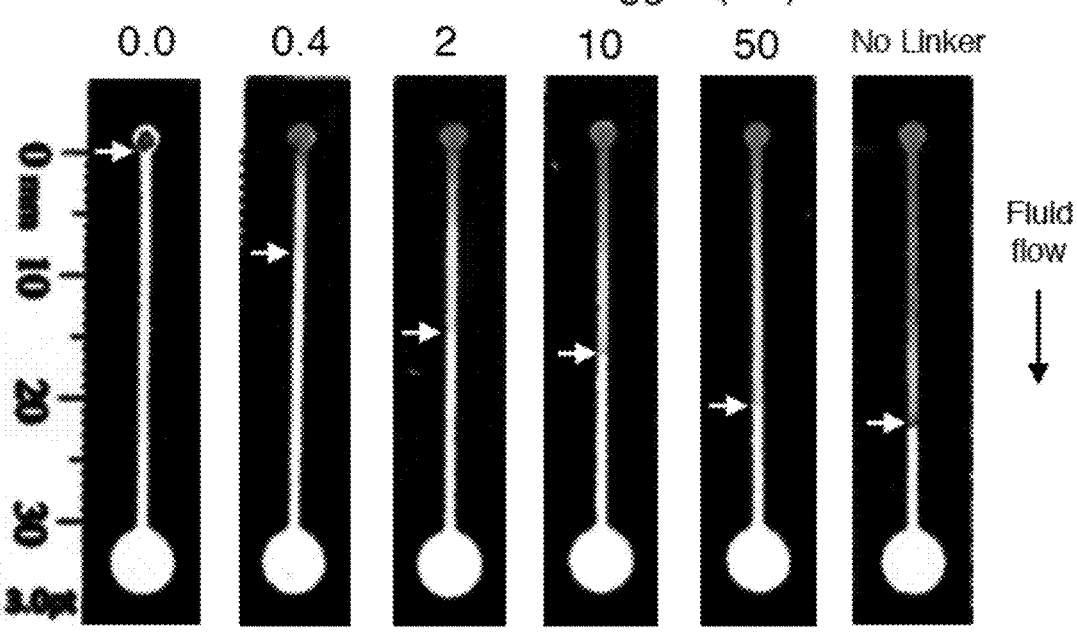

FIG. 14. PA-DNA hydrogel μPAD as a fluidic capillary resistor. Representative μPAD channel buffer wicking lengths at the 5 min endpoint. μPADs were filled with 0.3 μL of DNA linker (100 μM) pre-incubated for 4 h at 37° C. in a cutting solution containing Cas12a (300 nM), MRSA crRNA (1 μM), dsDNA MRSA Trigger (0 nM, 0.4 nM, 2 nM, 10 nM, 50 nM) and 1×NEB Buffer 2.1.

Figure 15:
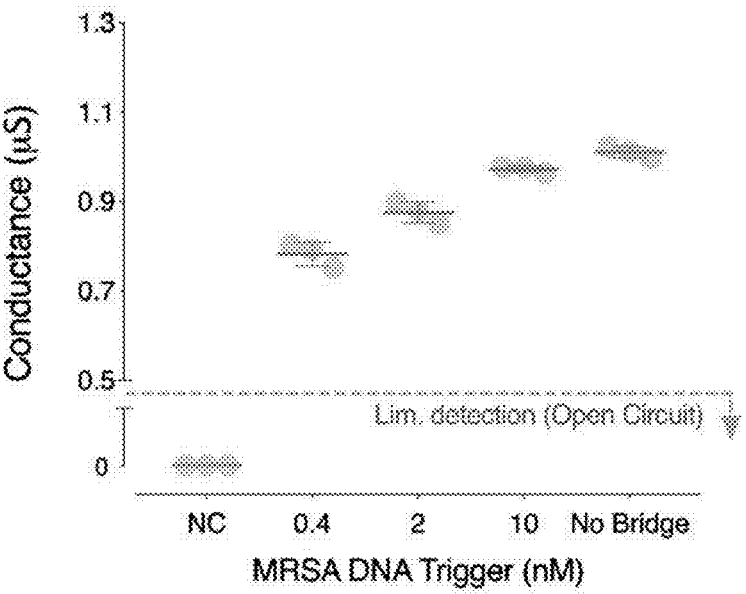

FIG. 15. Endpoint measurements (t=5 min) of electrical conductance during flow for different concentrations of dsDNA MRSA trigger. The Cas12a trans-cleavage reaction mix containing ssDNA gel linker (10 μM) was deposited on the μPAD after 1 h pre-digestion. The PA-DNA hydrogel precursors Ps-X and Ps-Y were produced with 7 wt % acrylamide rather than 4%. The use of a higher polyacrylamide percentage created a higher viscosity precursor which required less ssDNA linker to generate flow-impeding gelation. As a result, this ssDNA linker could be cut sufficiently with reduced pre-incubation times (1 h as opposed to 4 h). However, overall system sensitivity to increasing levels of dsDNA trigger appears to be reduced compared to PA-DNA μPAD using hydrogel precursors produced with 4 wt % acrylamide shown in FIG. 4C.

Figure 16:
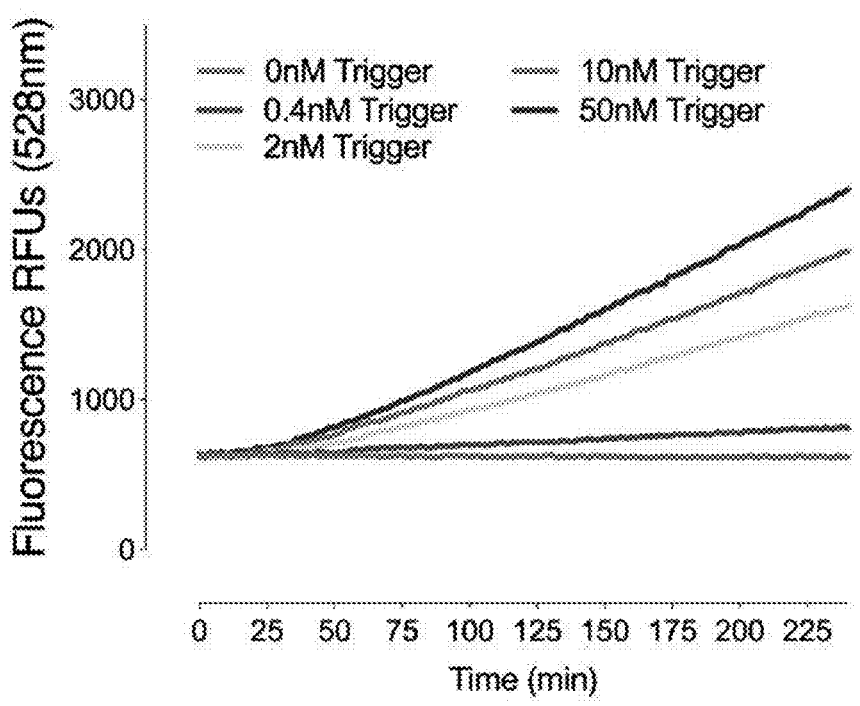

FIG. 16. Cas12a cutting of 100 μM ssDNA Linker in conjunction with 750 nM quenched fluorescent ssDNA. Increasing levels of trigger DNA lead to increased fluorescent signal, which indicates an increased trans-cleavage activity of ssDNA content in solution, including the ssDNA linker used in PA-DNA gelation.

Figure 17A:
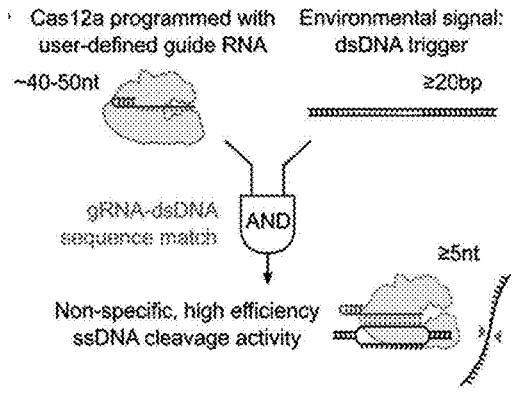
Figure 17B:
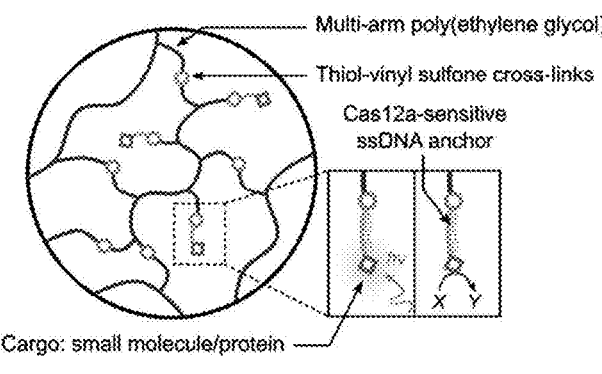
Figure 17C:
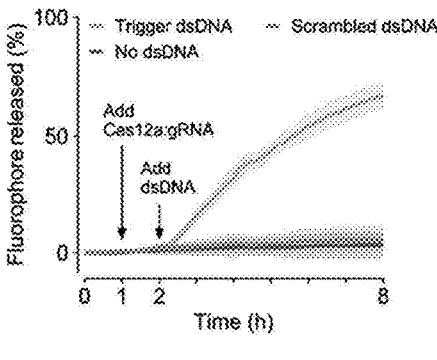
Figure 17D:
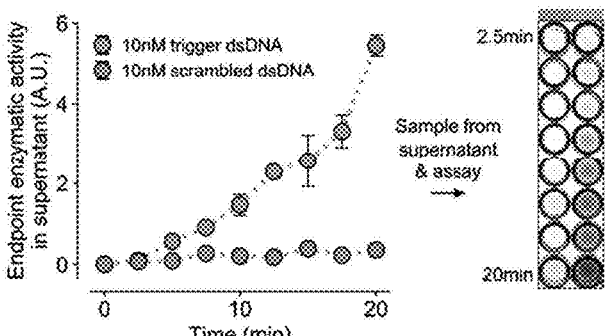
Figure 17E:
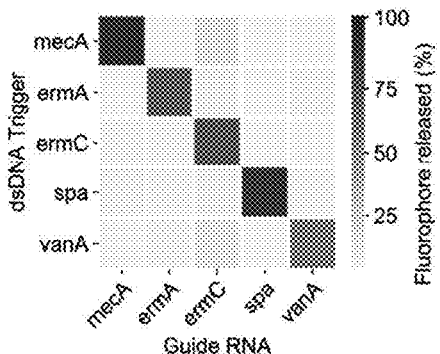
Figure 17F:
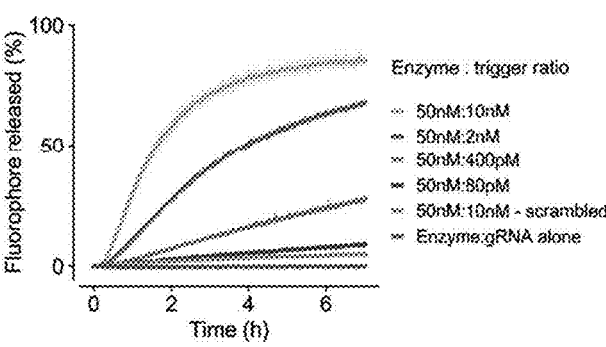
Figure 17G:
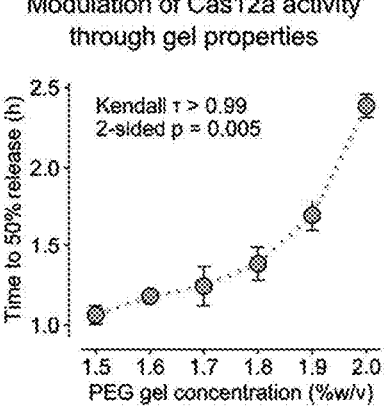
Figure 17H:
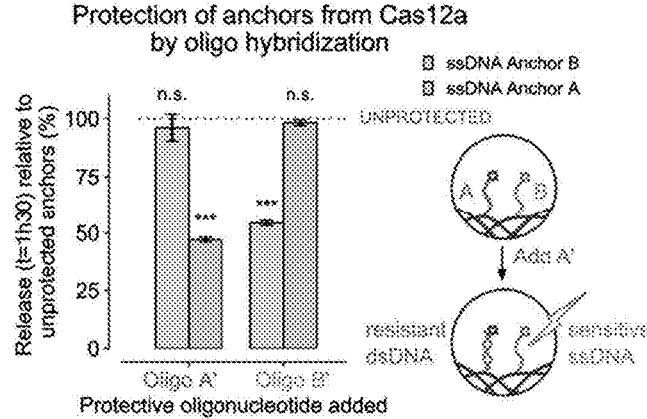

FIGS. 17A-17H. Cas12a-mediated release of small molecules and enzymes from PEG hydrogels. FIG. 17A. The sequence specificity of Cas12a is programmed by a gRNA. Recognition and binding of the corresponding dsDNA trigger activates the ssDNA collateral cleavage activity. FIG. 17B. ssDNA acts as a cleavable linker for attaching molecular payloads to an inert PEG matrix. FIG. 17C. Release of a tethered Cy3 fluorophore by Cas12a is initiated only upon introduction of a specific dsDNA trigger and not a scrambled dsDNA control sequence. FIG. 17D. Functional enzymes can be anchored into the hydrogel and released by Cas12a in sufficient quantities for visual detection in a horseradish peroxidase (HRP) activity assay within minutes. FIG. 17E. Activation of Cas12a and fluorophore release (t=8 h) is defined by the complementarity between a dsDNA sequence and the gRNA of Cas12a. FIG. 17F. In-gel cleavage dynamics are controlled by the amount of dsDNA trigger available for Cas12a activation. FIG. 17G The cross-linking density of the PEG hydrogels modulates the release rate of the cargo by Cas12a. The correlation was analyzed using a Kendall rank test. FIG. 17H. Pre-hybridization of the ssDNA linkers with a matching oligonucleotide selectively reduces the release rate of molecules anchored in the gel (observed at t=1.5 h). The means were compared to independent sample that was not pre-protected with oligonucleotides (gRNA alone. Differences in the means of the four test conditions and the unprotected controls were analyzed using a t-test (Bonferroni adjusted $\alpha$=0.0125, p-values: n.s.>0.05, ***<0.0001). All plots show mean±SD for n≥3 replicates.

Figure 18A:
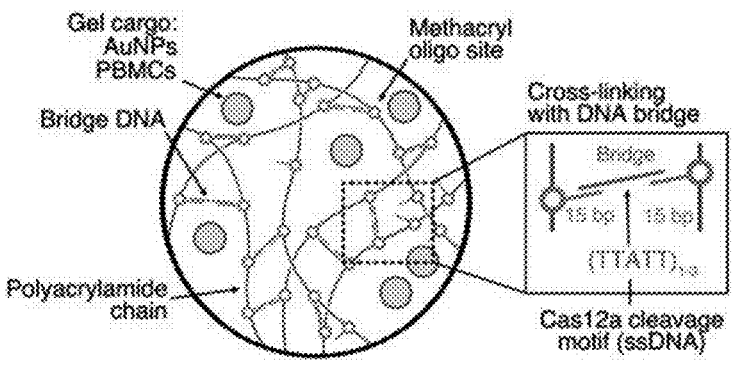
Figure 18B:
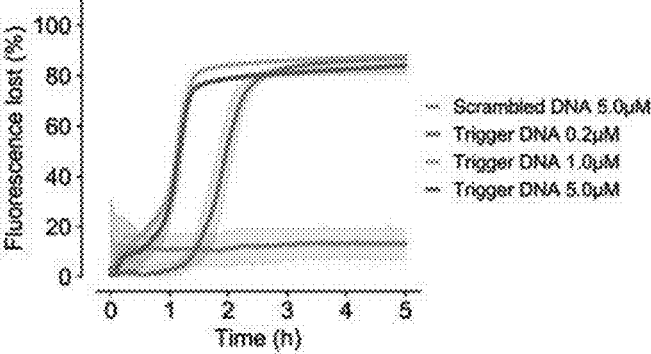
Figure 18C:
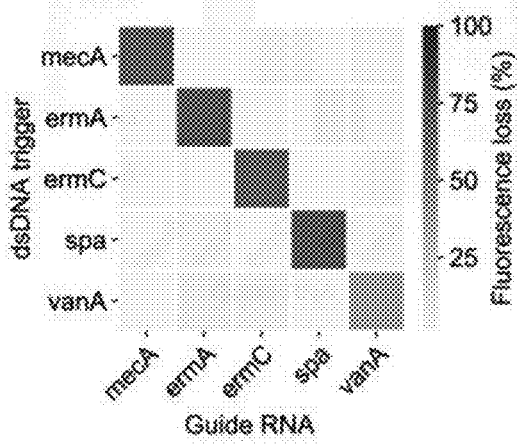
Figure 18D:
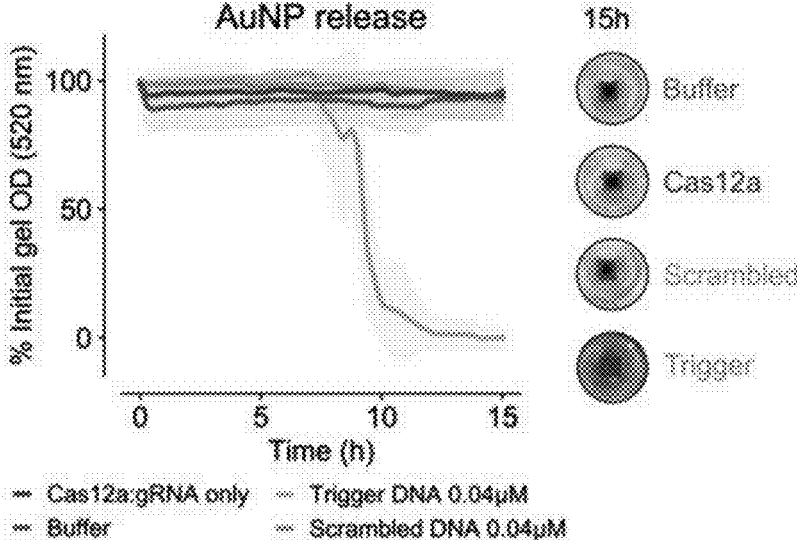

FIGS. 18A-18E. Programmable release of nanoparticles and live cells from polyacrylamide-DNA hydrogels. FIG. 18A. ssDNA bridges lock DNA-functionalized polyacrylamide chains into a 3D network. FIG. 18B. Cas12a-mediated degradation of PA-DNA gels stained with EVAGREEN® intercalating DNA dye. FIG. 18C. Degradation of gel with 25 combinations of gRNAs and dsDNA triggers and comparison of signals after 12 h. FIG. 18D. Release of AuNPs from 7% (w/v) PA-DNA gels using Cas12a collateral cleavage tracked by measuring the optical density (520 nm) through the gel. The Cas12a-gRNA and dsDNA trigger were encapsulated in the gel with the AuNPs (concentrations shown include supernatant volume). FIG. 18E. Sequence-specific degradation of PA-DNA gels leads to the release of encapsulated non-adherent PBMCs. Cells were stained before encapsulation using Calcein blue-AM and ethidium homodimer, and gels were labelled with a fluorescein-functionalized ssDNA bridge. See FIGS. 41A-41C and FIGS. 42A-42B for post-degradation live-dead staining.

Figure 19B:
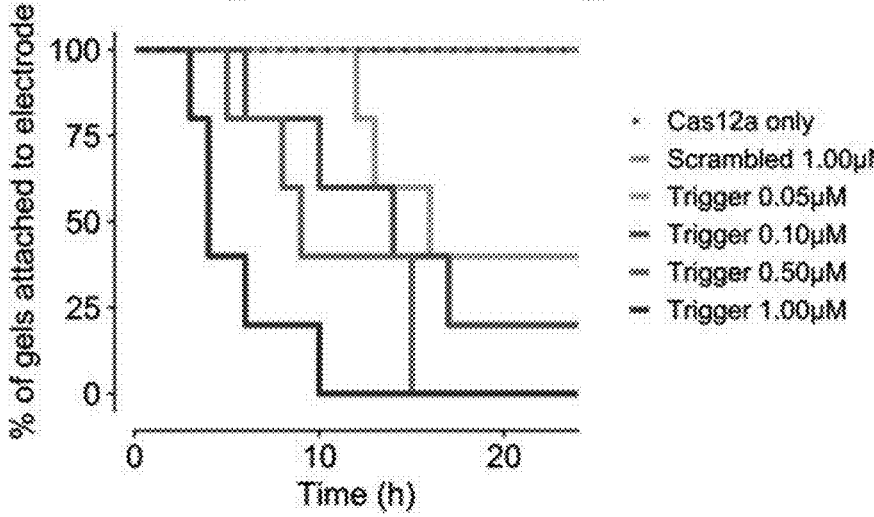
Figure 19C:
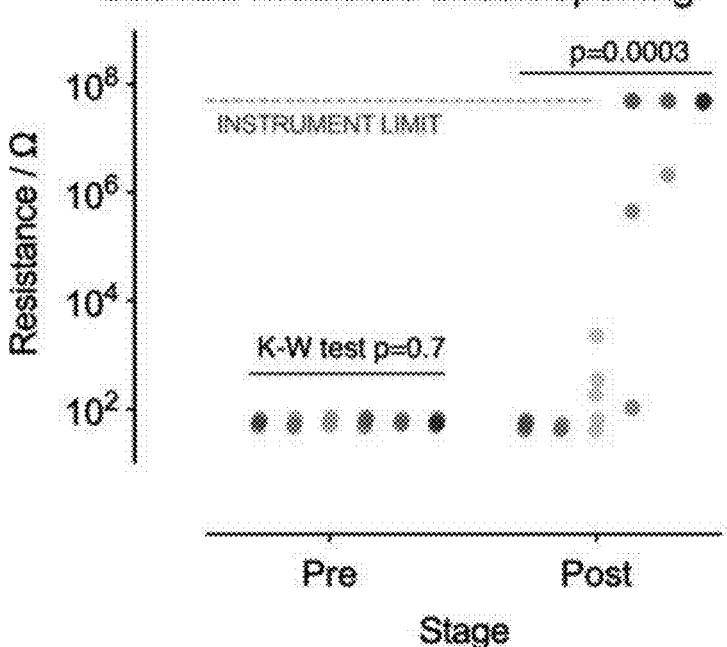
Figure 19D:
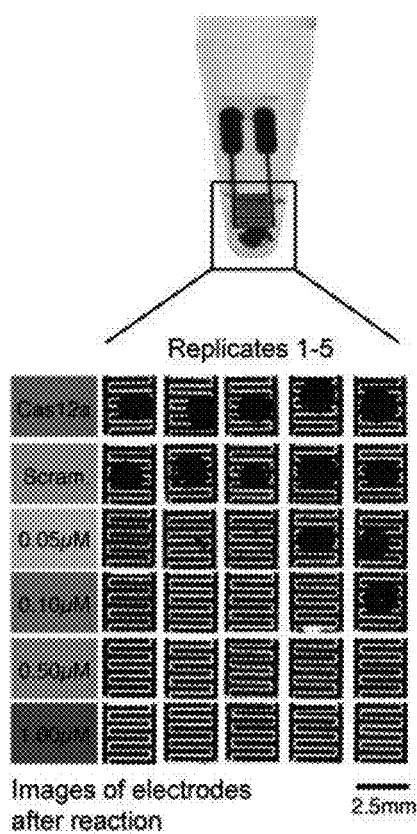

FIGS. 19A-19D. Carbon black-DNA (CB-DNA) hydrogels can be used as Cas12a-actuated electrical fuses. FIG. 19A. Schematic of the experimental workflow. FIG. 19B. Degradation kinetics of carbon black-DNA gels with increasing concentrations of DNA trigger (n=5 per condition). Replicates were inspected at 1 h intervals to detect detachment of CB-DNA gels from inkjet-printed silver interdigitated electrodes (IDEs). FIG. 19C. Electrical resistance across the IDEs in FIG. 19B after removal from the reaction mix upon detachment of the CB-DNA gel or at 24 h if no detachment occurred. Measurements before and after the reaction were compared separately using a Kruskal-Wallis test (before: p=0.7, after: p=0.0003) and Dunn's post-hoc test (before: all>0.99; after: p<0.05 for both 1.0 μM and 0.5 μM vs controls, p>0.05 otherwise). FIG. 19D. A representative image of a gel in the reaction mix detached from its IDE (top) and microscopy images of the IDEs in FIG. 19B after removal from the reaction (bottom). Images are quantified in FIG. 43A.

Figure 20A:
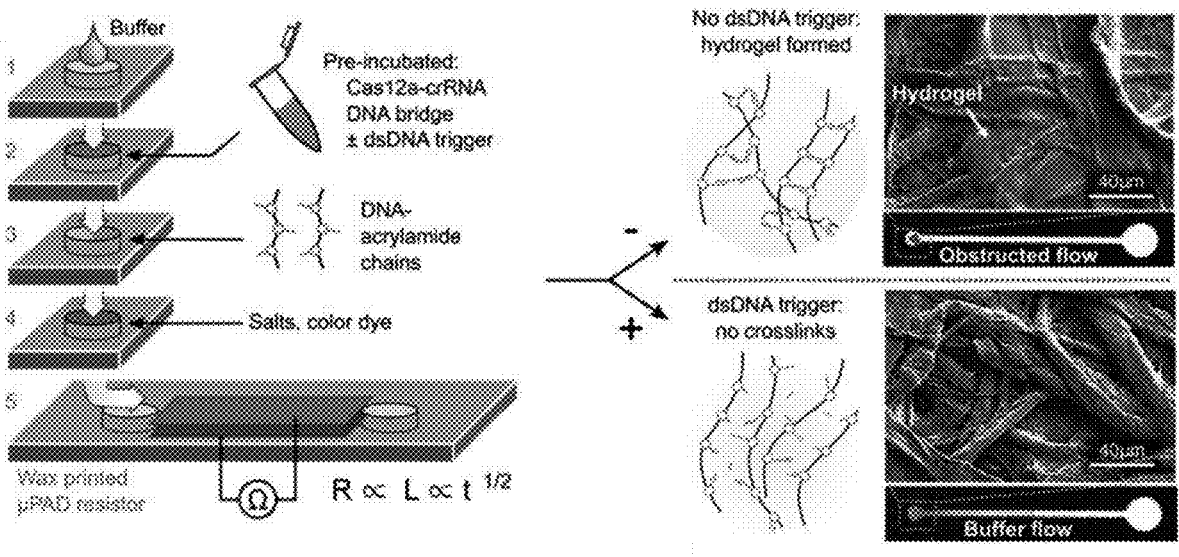
Figure 20D:
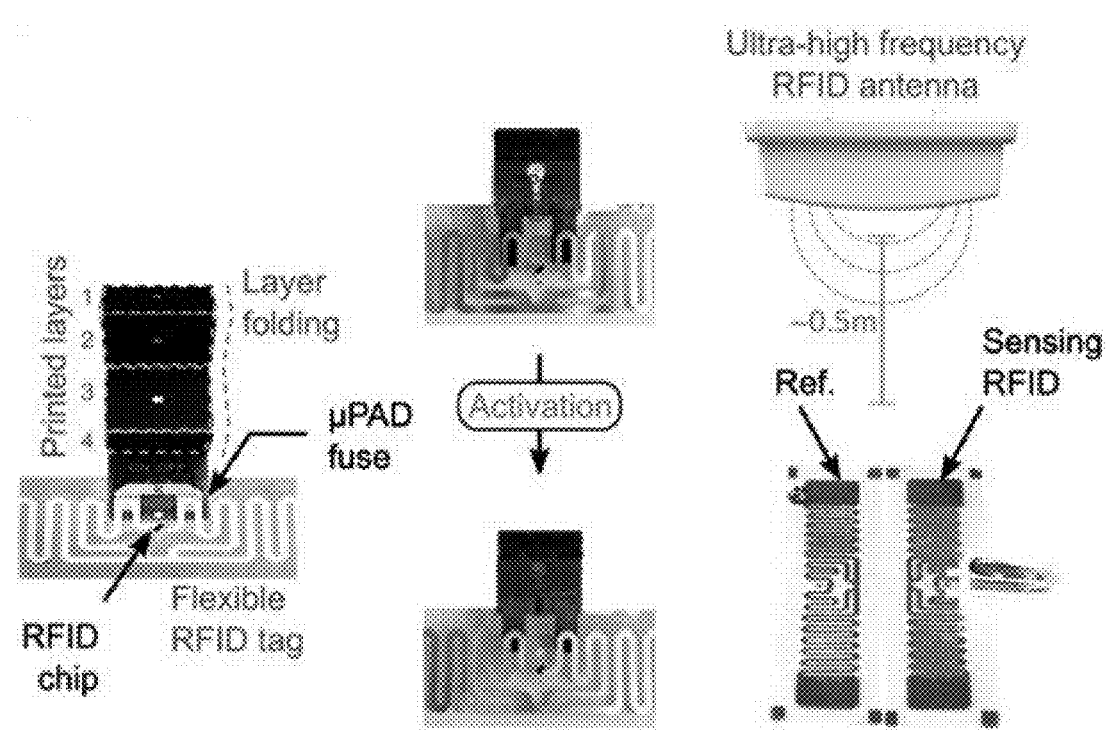
Figure 20E:
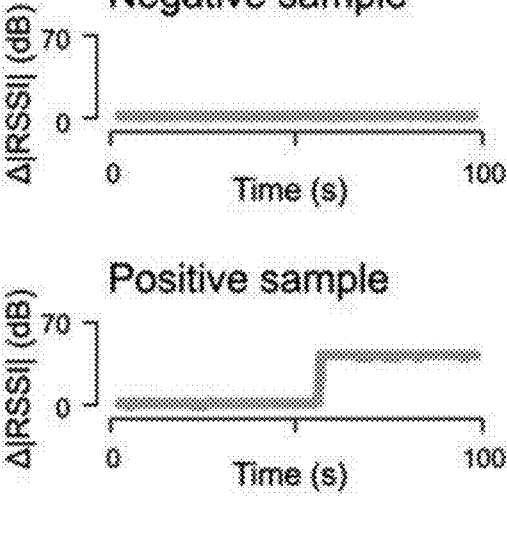
Figure 49:
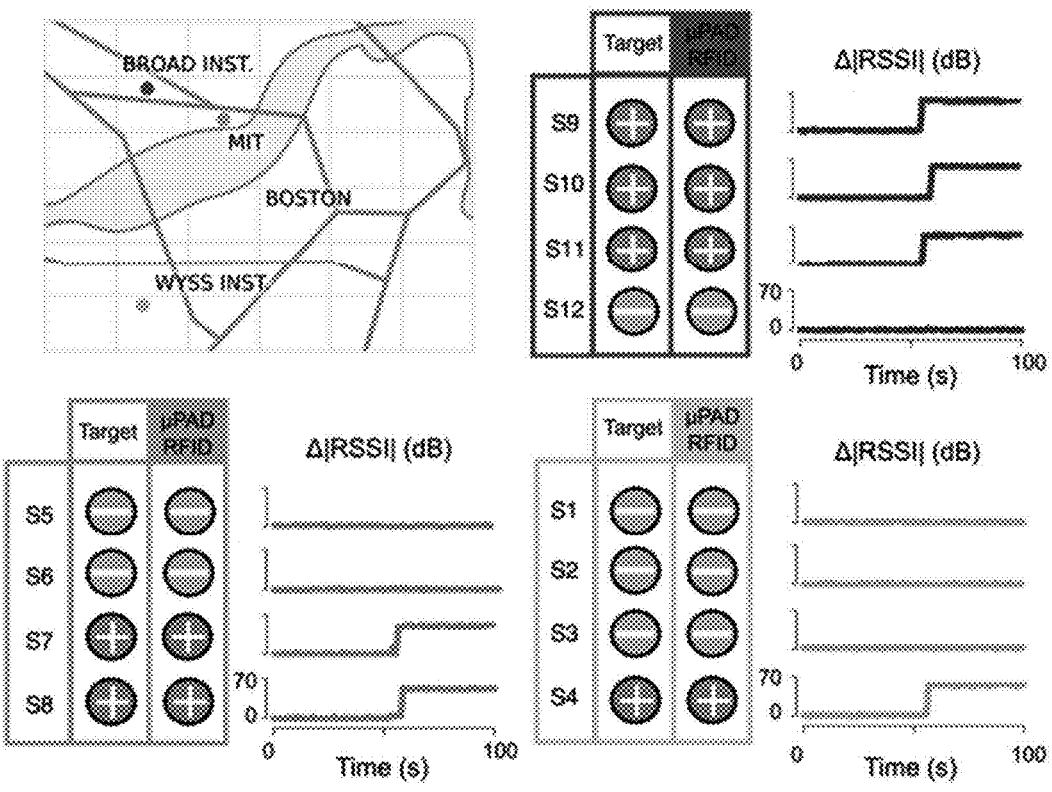

FIGS. 20A-20E. Cas12a digestion of hydrogel precursors modulates permeability of a paper-based microfluidic device (μPAD) with dual visual and electronic readouts for diagnostic applications. FIG. 20A. Schematic of the stackable μPAD design (40) modified for operation with CRISPR-gels and electrical readout. Layers 1-4 of the PAD contain circular hydrophilic regions that form a continuous channel on folding and feed into a lateral flow channel in layer 5. The channel in layer 5 was covered with conductive tape to measure conductivity as a function of buffer wicking. In the presence of target trigger, pre-incubation reaction with Cas12a leads to cleavage of the DNA linker, preventing hydrogel cross-linking in the channel and enabling flow. The inset shows SEM images of paper regions with (top) and without (bottom) cross-linked hydrogel. FIG. 20B. Endpoint measurements (t=5 min) of the colorimetric coupled reverse transcription-recombinase polymerase amplification (RT-RPA) μPAD hydrogel detection system for different concentrations of ssRNA EBOV input (mean±SD, n=3). Representative images of μPAD channel flow are shown. The positive control corresponds to flow with no ssDNA bridging strand in the pre-incubation reaction, and the negative control corresponds to flow with an undigested ssDNA bridging strand. Student's t-test p=0.0057 for differences in the means of the 0 and 11 am ssRNA samples. FIG. 20C. Endpoint measurements (t=5 min) of electrical resistance across the channel for different concentrations of dsDNA MRSA trigger input deposited after the 4 h pre-digestion step. FIG. 20D. Schematic illustrating the integration of the paper-fluidic device with an RFID flexible tag. Cas12a activation in the pre-incubation step results in the short-circuiting of an interdigitated electrode arrangement in the loop RFID tag, thereby altering the received signal strength indicator (RSSI). For the detection of trigger events, the differential signal between a test RFID μPAD and a reference RFID was monitored in real time using an ultrahigh frequency RFID antenna. A sudden increase in absolute RSSI difference between testing and reference RFID tags results from short circuiting events that are indicative of Cas12a activation by a dsDNA trigger. FIG. 20E. Representative signal traces for positive and negative results in the experimenter-blinded trial of the RFID μPAD device (FIG. 49). Samples containing either 0 aM (negative) or 11 aM (positive) EBOV ssRNA trigger were amplified by RT-RPA, incubated with the ssDNA gel bridging strand and Cas12a-gRNA for 4 h, and assayed on a μPAD-RFID device.

Figure 21:
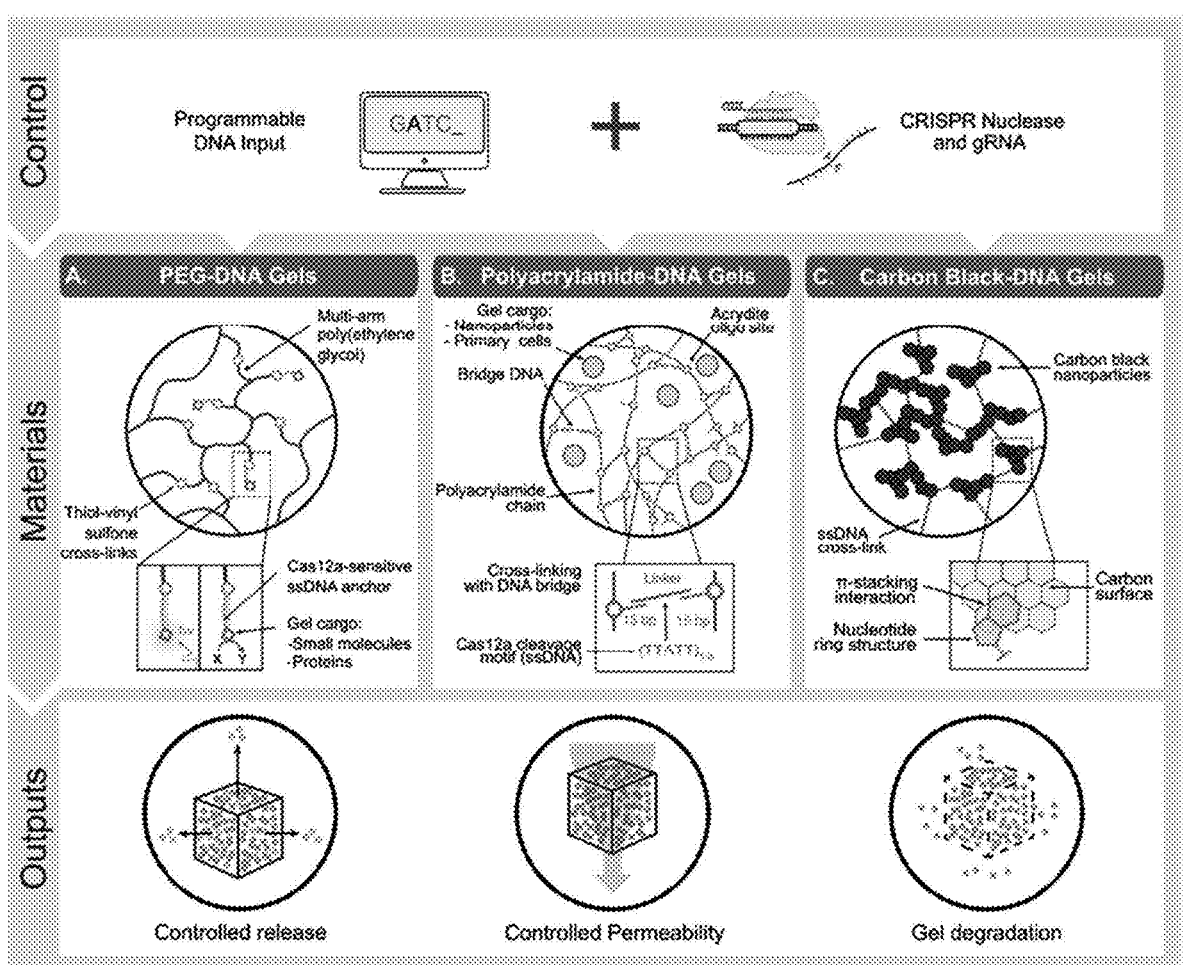

FIG. 21. CRISPR-mediated DNA-hydrogel modulation. RNA-guided Cas endonucleases can be easily programmed for specific DNA inputs (top panel) and used in combination with different hydrogel chemistries (middle panel) to modulate system properties at multiple scales, such as controlled release of molecules, particles, or live cells; fluid permeability; and bulk material degradation (bottom panel). Three basic CRISPR-gel systems were explored: branched poly(ethylene glycol)-based hydrogels for release of DNA-anchored compounds; degradable polyacrylamide-DNA hydrogels for release of encapsulated payloads (e.g., particles or live cells), as well as for controlling permeability of microfluidic systems via cleavage of a hydrogel ssDNA linker; and conductive carbon black-DNA hydrogels for electrical circuit bridging with fuse-like responsiveness to dsDNA trigger activation. All presented CRISPR-gels respond to activation of a Cas12a-gRNA complex through the presence of a dsDNA trigger, and are designed to leverage either the highly specific dsDNA targeted cleavage activity of Cas12a for multiplexed response or the high-turnover ssDNA collateral cleavage activity of Cas12a to modulate large-scale hydrogel properties.

FIG. 22. Programmability of the Cas12a-based mecA detection system. Three gRNAs were generated against different MRSA targets; the ability of gRNA-defined dsDNA triggers to activate Cas12a collateral cleavage activity was tested using a ssDNA fluorophore-quencher probe. The reactions contained 30 nM Cas12a, 90 nM gRNA, 2.5 nM dsDNA specific trigger and 750 nM quenched fluorescently labeled ssDNA reporter, with sequence: 5' (6FAM)-TTATT-(Iowa Black™ FQ)3'. Fluorescence signal increased in a similar manner for all three gRNA/dsDNA target pairs tested as the ssDNA probe was cleaved. The background activities without dsDNA triggers were also similar for the three different gRNAs. Individual replicates are plotted for duplicate experiments.

FIGS. 23A-23F. In-solution validation of Cas12a-based detection system for mecA. FIG. 23A. Fluorescence time-course results for MRSA1 gRNA Cas12a collateral cleavage assays with decreasing concentrations of a specific (SP) dsDNA trigger in solution. FIGS. 23B-23D. The same experiment was repeated as in FIG. 23B, except that the dsDNA trigger respectively contained one mismatch ("1M"), three mismatches ("3M") or was a randomly permutated control sequence (scrambled, "SC"). Full sequences are available in TABLE 4. All reactions contained 50 nM Cas12a, 62.5 nM MRSA1 gRNA, 750 nM quenched fluorescently labeled ssDNA reporter and the specified concentrations of dsDNA triggers. The sequence of the fluorescently labeled reporter was: 5' (6FAM)-TTATT-(Iowa Black™ FQ)3'. (FIGS. 23E-23F) As the number of nucleotide mismatches between the trigger and the gRNA increased, the rate of ssDNA collateral cleavage and the corresponding fluorescence signal at t=60 min decreased. Statistics in (FIG. 23F) represent results from a Brown-Forsythe ANOVA (p=0.002, with p<0.05 for all Games-Howell's multiple comparison tests between means).

FIG. 24. Programmable Cas12a-mediated release of small molecules conjugated to dsDNA linkers. Specific release of pre-programmed fluorescent cargo molecules anchored to dsDNA linkers in branched PEG-gelatin hydrogels using Cas12a cis-cleavage activity without bulk gel degradation (t=14 h). Incubation of a gel harboring two distinct dsDNA anchors for different fluorophores with Cas12a reveals no significant cutting when the Cas12a gRNA sequence does not match that of the dsDNA anchors ("Non-targeting gRNA" directed against an unrelated sequence) as assessed by one-sample t-tests versus the theoretical value 0 (n=4, both p>0.05). On the other hand, when the guide sequence matches one of the two anchor sequences of the gel, Cas12a preferentially cuts the linker matching the gRNA (two-sample t-test versus off-target molecule signal, n=4, p<0.0001). The amount of target molecule released is consistent with a low turnover (statistically no different from the theoretical value of 1 cutting event per enzyme based on a one-sample t test, n=4, p=0.07) as reported in other articles with previous observations (2). "n.s.": non-significant.

FIGS. 25A-25B. Strategy to measure released fluorescent molecules and NPs from hydrogels. FIG. 25A. PEG-DNA hydrogels were formed on the sides of 96-well plates, and a mixture containing Cas12a-gRNA and trigger dsDNA was added in solution. Fluorescence of released small molecules was measured in the middle of the wells (Ex: 554 nm/Em: 625 nm). FIG. 25B. Hydrogels were formed loaded with gold nanoparticles inside Press-to-Seal™ silicone isolators attached to the center of individual wells in a 24-well tissue culture plate. Transmitted light at 520 nm was used to measure the release of nanoparticles and gel degradation.

Figure 26E:
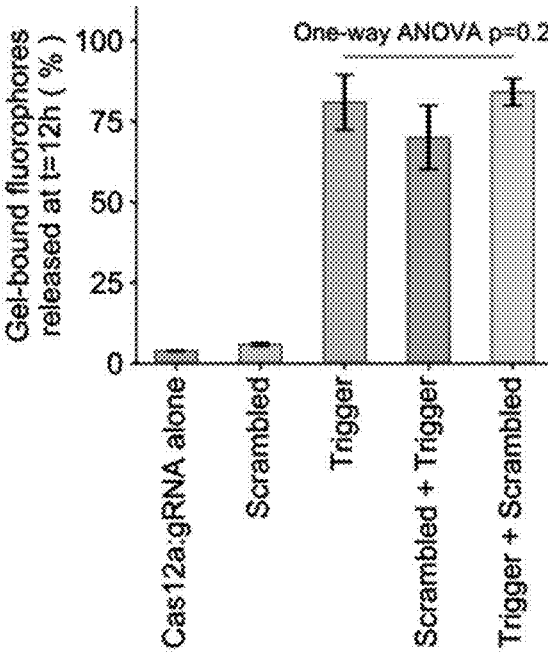

FIGS. 26A-26E. Sequential additions of scrambled dsDNA and trigger dsDNA show that Cas12a-gRNA is only activated upon addition of sequence-specific dsDNA trigger. After 1 h of incubation in buffer, Cas12a-gRNA was added in the supernatant surrounding PEG hydrogels decorated with fluorescent reporter cargos. FIG. 26A. No Cas12a activation was observed when scrambled dsDNA was added at t=2 h followed by addition of buffer at t=4 h. FIG. 26B. Gel-bound fluorophore was released after trigger dsDNA addition at t=2 h, and release continued after addition of buffer at t=4 h. FIG. 26C. No release of fluorophore from hydrogel is observed after addition of scrambled dsDNA at t=2 h, and release started after specific dsDNA trigger was added at t=4 h. FIG. 26D. Fluorophore release started at t=2 h, after addition of dsDNA trigger, and release continued despite the addition of scrambled dsDNA at t=4 h. FIG. 26E. After 12 h, the overall level of cargo release was comparable in all hydrogels that were exposed to dsDNA trigger-activated Cas12a, regardless of the order of addition of scrambled or trigger dsDNA, while little fluorophore release was observed in cases where dsDNA trigger was not present. Mean and SD are plotted for triplicate experiments. FIGS. 26A-26D present different samples from the same experiment (also shown in FIG. 17C).

Figure 27:
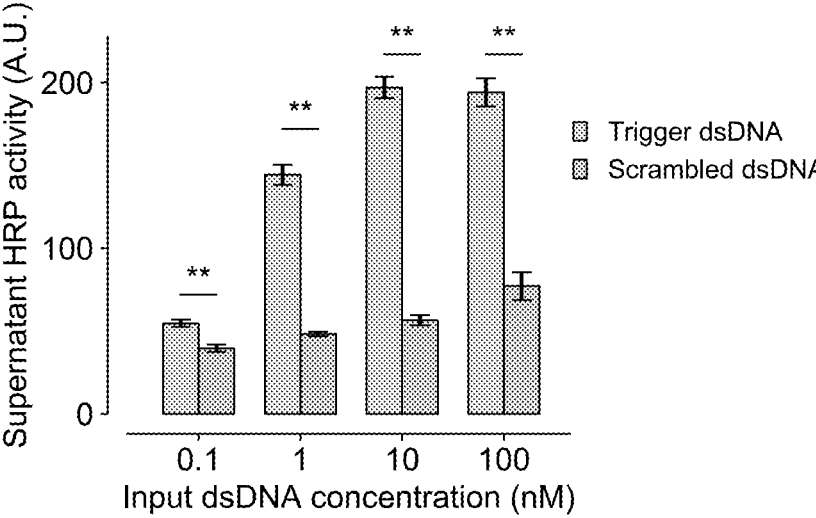
Figure 28B:
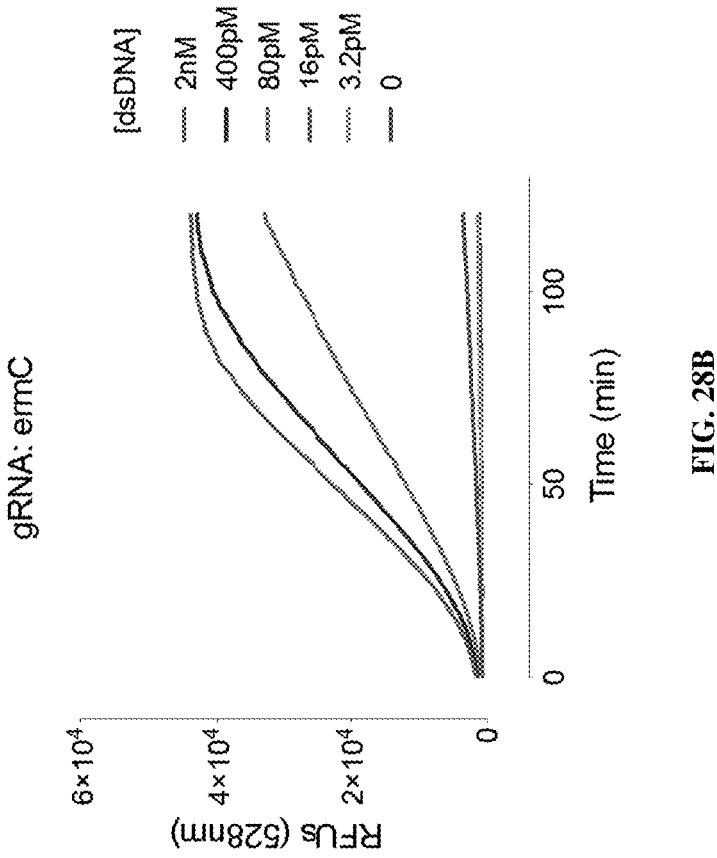
Figure 28A:
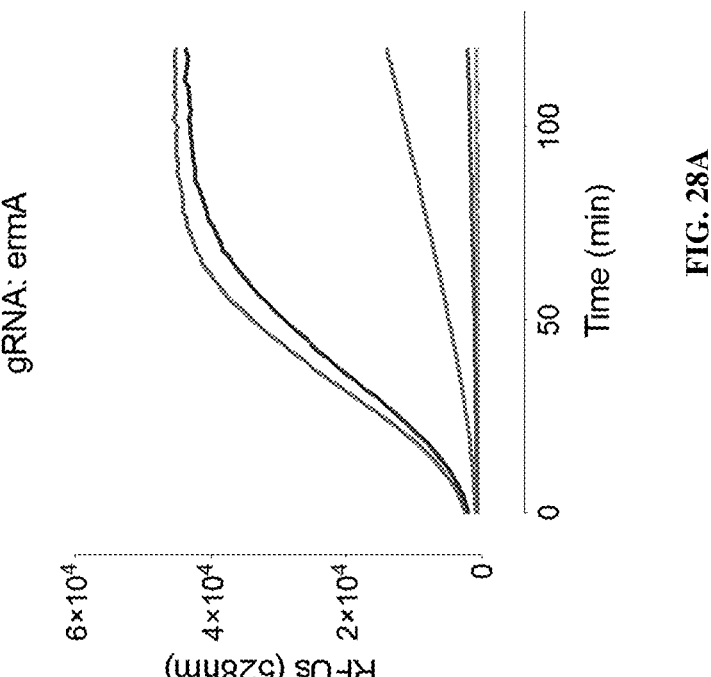
Figure 28D:
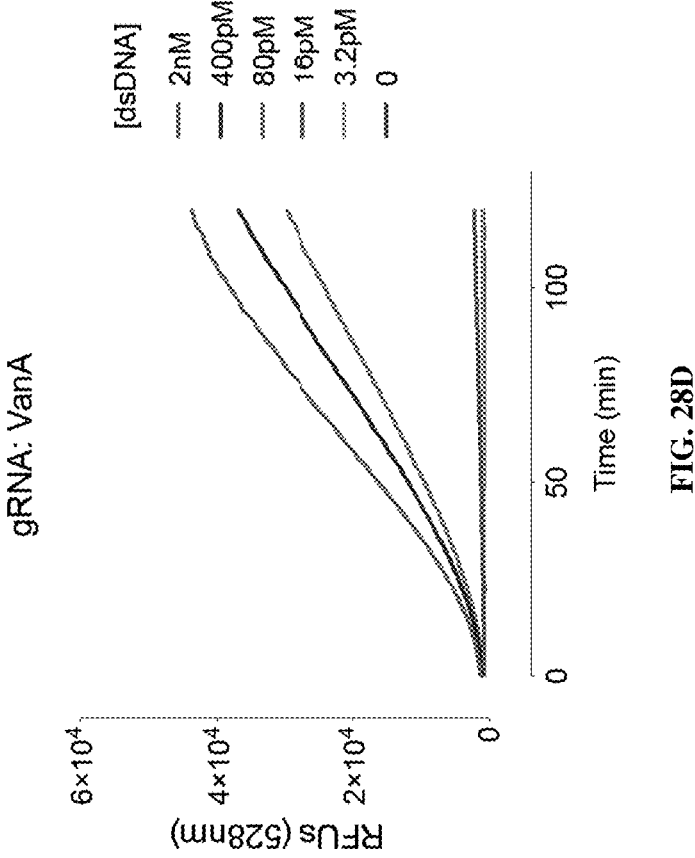
Figure 28C:
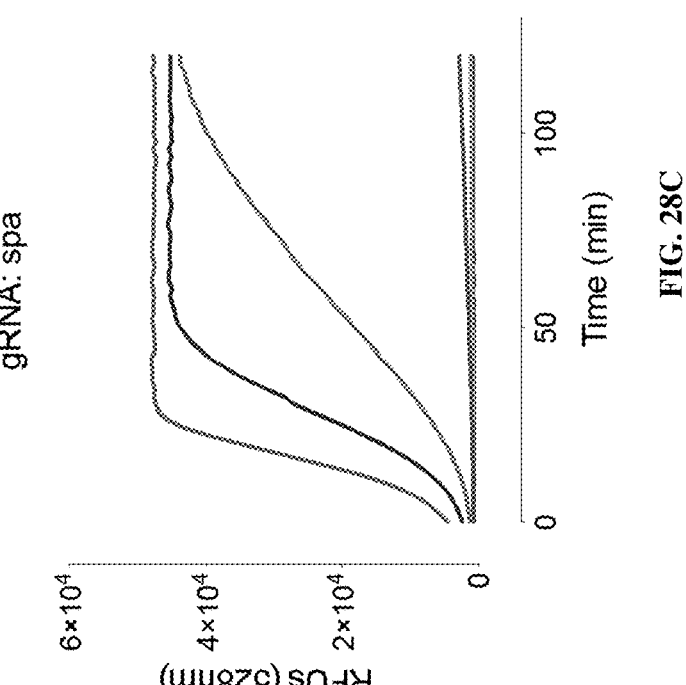

FIG. 27. HRP conjugated to ssDNA anchors on hydrogels is released upon addition of trigger dsDNA. TMB substrate conversion was measured in supernatants from hydrogels in which HRP had previously been conjugated to ssDNA anchors via a streptavidin-biotin interaction. Cas12a, gRNA, and dsDNA were incubated in a 1:2:1 molar ratio in 50 μL of supernatant. Upon Cas12a activation, ssDNA anchors were cleaved, releasing HRP into the supernatant over the course of 3 h. Scrambled dsDNA led to significantly lower Cas12a activation. The significance of the difference between matching conditions was assessed by t-tests (n=3 samples, Bonferroni adjusted, significance threshold α=0.0125, all p-values<0.001). Mean and SD are plotted for triplicate experiments.

FIGS. 28A-28D. Programmability of Cas12a activity targeting *Staphylococcus aureus*-relevant genes. Four gRNAs were generated against different *Staphylococcus aureus*-relevant genes: (FIG. 28A) ermA, (FIG. 28B) ermC. (FIG. 28C) spa and (FIG. 28D) vanA. Fluorescence time-course results for the four gRNA-dsDNA target pairs indicate limits of detection between 16-80 pM. The ability of gRNA-defined dsDNA triggers to activate Cas12a collateral cleavage activity was tested using a ssDNA fluorophore-quencher probe [5' (6FAM)-TTATT-(Iowa Black™ FQ) 3']. The reactions contained 50 nM Cas12a, 62.5 nM MRSA1 gRNA. 750 nM quenched fluorescently labeled ssDNA reporter and the specified concentrations of dsDNA triggers. The background activities without dsDNA triggers were similar for the four different gRNAs. Mean and SD are plotted for triplicate experiments.

Figure 29A:
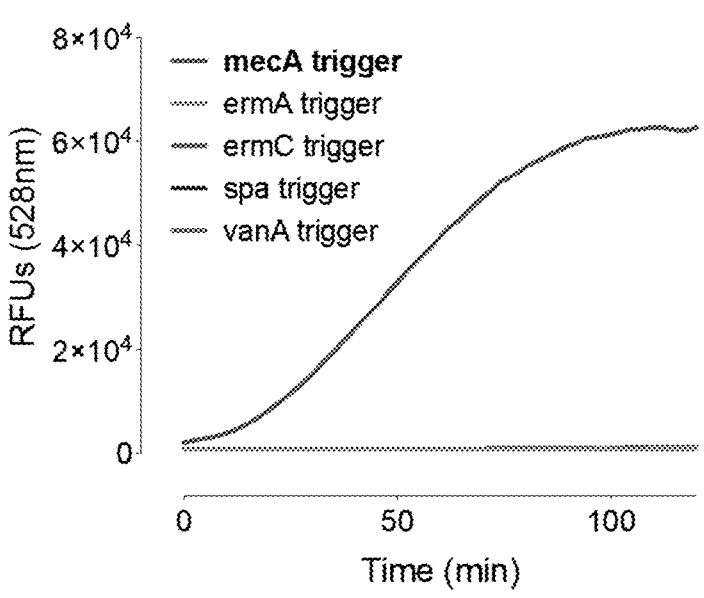
Figure 29B:
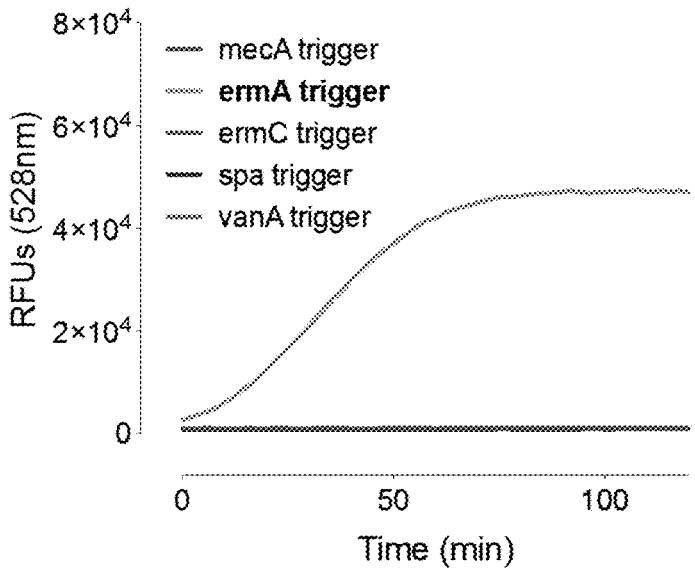
Figure 29C:
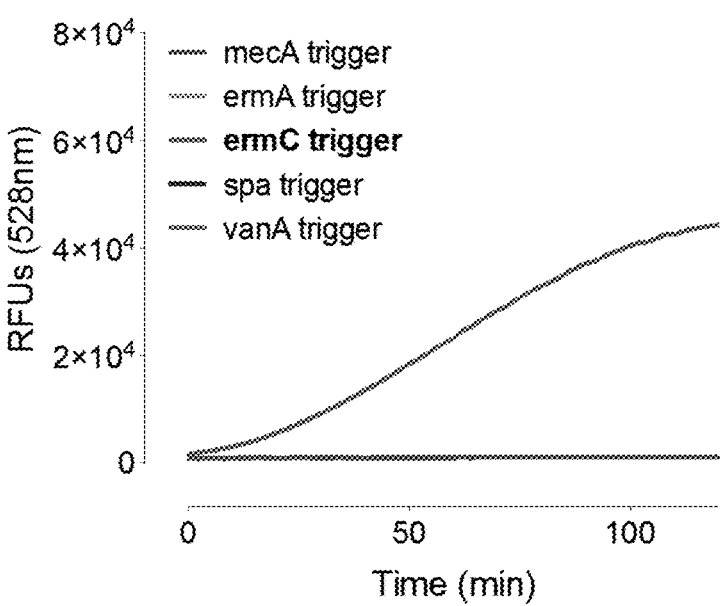
Figure 29D:
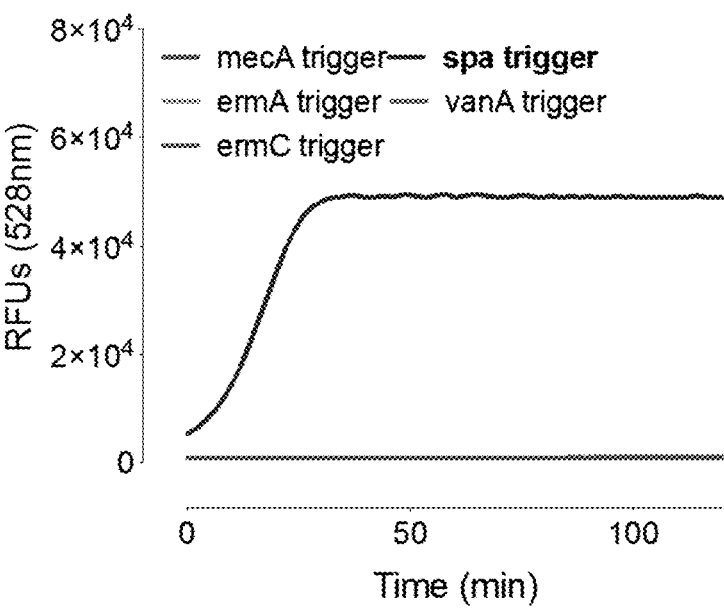
Figure 29E:
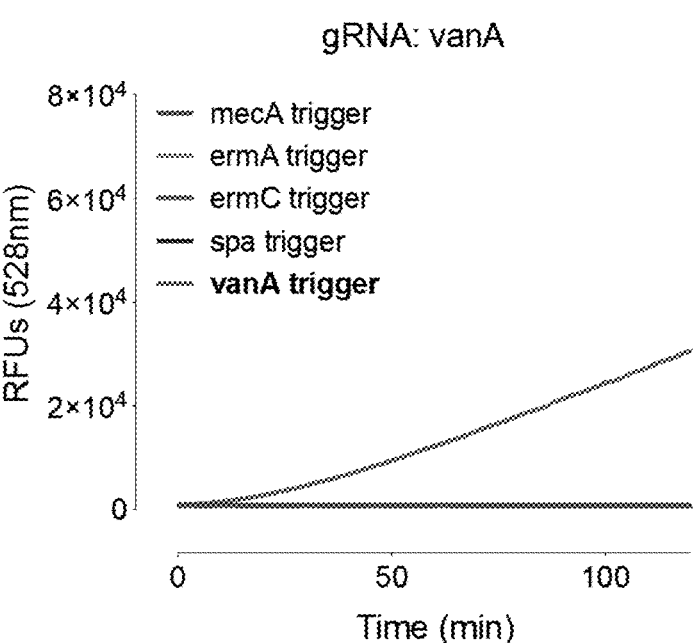
Figure 29F:
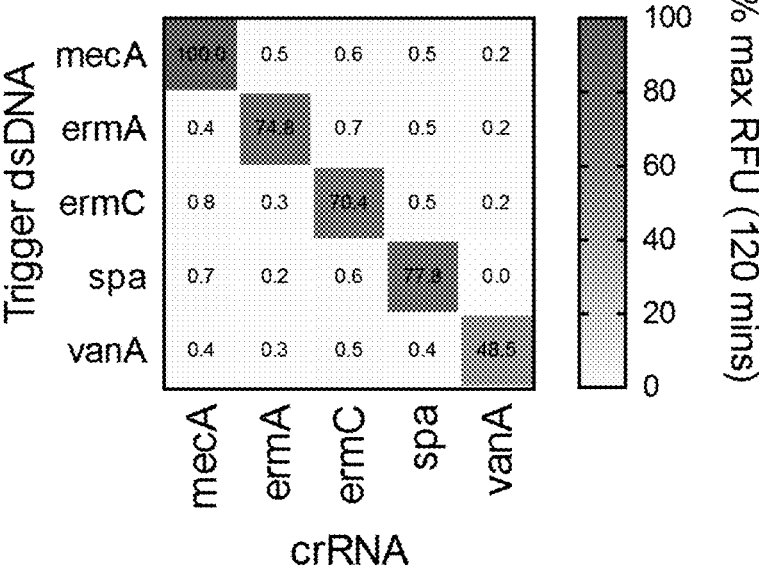

FIGS. 29A-29F. Orthogonality of Cas12a activity targeting *Staphylococcus aureus*-relevant genes in solution. Five gRNAs targeting (FIG. 29A) mecA, (FIG. 29B) ermA, (FIG. 29C) ermC, (FIG. 29D) spa and (FIG. 29E) vanA were tested in pairs with each dsDNA trigger. Fluorescence time-course results for the 25 gRNA-dsDNA target pairs indicate that Cas12a activation and collateral cleavage activity only occurred in the presence of on-target dsDNA. FIG. 29F. Summary heat-map comparing the normalized maximum fluorescence of the 25 combinations of gRNA-dsDNA pairs after 2 h; values in the diagonal represent on-target dsDNA-gRNA pairs. The background activities of off-target dsDNA triggers were comparable for the five different gRNAs. The reactions contained 50 nM Cas12a, 62.5 nM MRSA1 gRNA, 750 nM quenched fluorescently labeled ssDNA reporter [5' (6FAM)-TTATT-(Iowa Black™ FQ) 3'] and 50 nM dsDNA triggers. Mean and SD are plotted for triplicate experiments.

Figure 30:
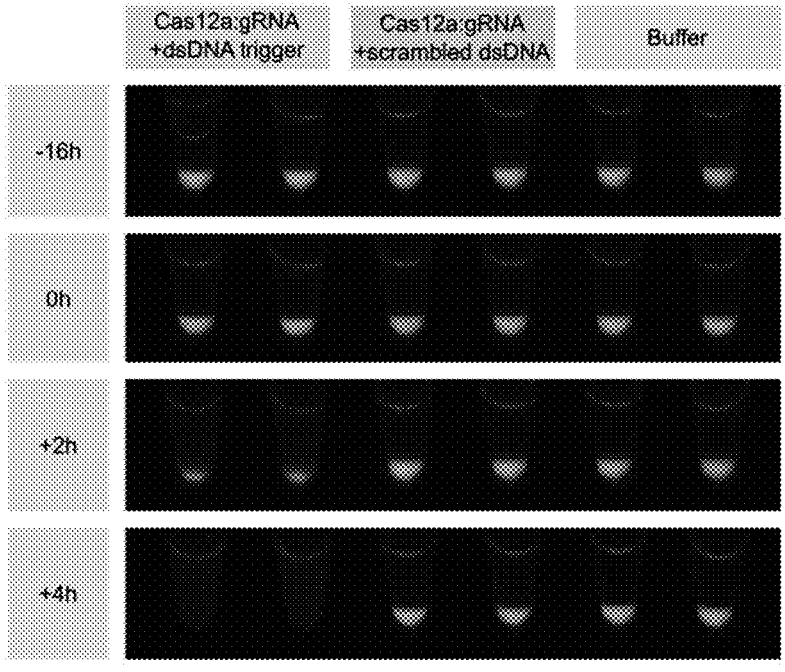

FIG. 30. Macroscopic observation of the degradation of ssDNA anchors and resulting fluorescent cargo release. Fluorescent ssDNA was conjugated to hydrogels in 0.2 mL microtubes. Over the course of 4 h after Cas12a-gRNA addition, hydrogels that received an on-target dsDNA progressively lost their fluorescence signal, while no fluorophore release was apparent in either the samples with the off-target (scrambled) dsDNA sequence or the negative control (Buffer only). Release of ssDNA linkers appeared to be controlled by diffusive processes.

Figure 31A:
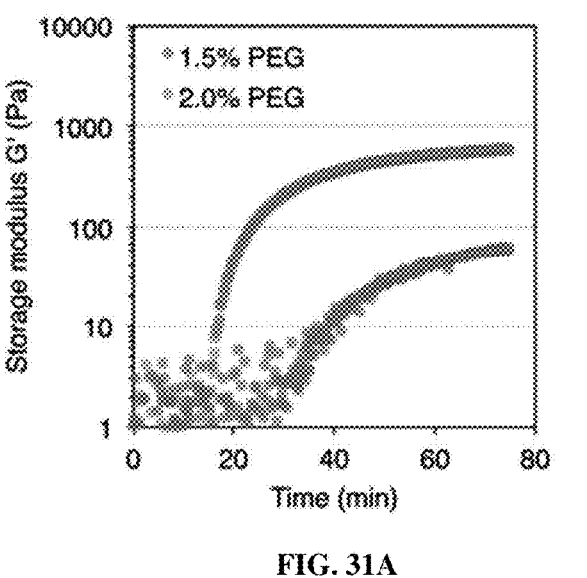
Figure 31B:
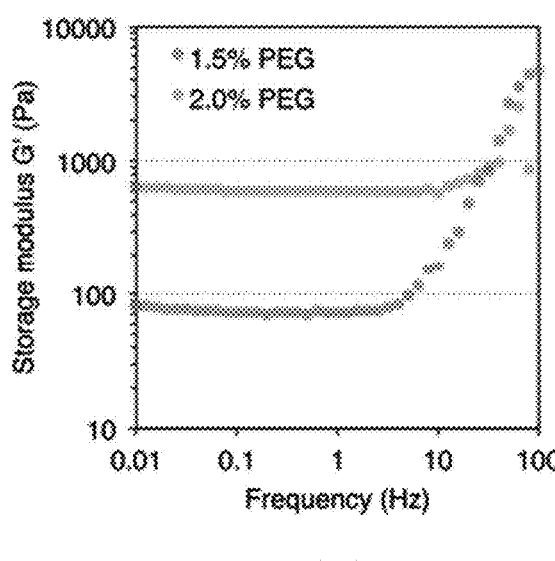

FIGS. 31A-31D. Cross-linking density in PEG gels affects the physical properties of the material. FIGS. 31A (time) and 31B (frequency). High and low concentration PEG hydrogels have fundamentally different physical behaviors, as measured by rheological analysis. FIG. 31C. Both thiol-(top panel, left) and vinyl sulfone-(top panel, right) functionalized precursors must be present to form a gel (bottom panel). FIG. 31D. Close up photograph of the polymerized PEG hydrogel.

FIG. 32. Release kinetics of a fluorescent ssDNA after Cas12a activation can be tuned by hydrogel density. Increasing percentage of PEG in hydrogels lead to slower release kinetics of fluorescent ssDNA after addition of Cas12a-gRNA and on-target dsDNA. Scrambled dsDNA did not lead to substantial release of fluorescent ssDNA. Mean and SD are plotted for n=4 experiments.

FIG. 33. Selective release of fluorescent ssDNA anchors attached on PEG hydrogels can be controlled by the addition of protective complementary ssDNA. Active Cas12a collaterally cleaves ssDNA, but not dsDNA. Thus, complementary ssDNA that can fully hybridize with ssDNA linkers prior to Cas12a activation can be used to slow down the degradation of the anchors. Increasing ratios of complementary ssDNA: anchor ssDNA lead to better protection from Cas12a degradation. The addition of a non-complementary ssDNA sequence does not lead to any detectable protection of the fluorescent ssDNA anchor. Mean and SD are plotted for triplicate experiments.

Figure 34C:
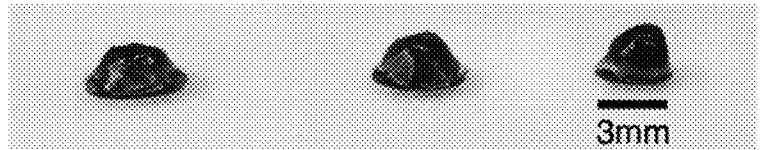

FIGS. 34A-34C. Incorporation of methacryl-functionalized oligos into high molecular weight acrylamide polymers. FIG. 34A. Agarose gel electrophoresis was used to compare the size of methacryl-functionalized ssDNA oligos X and Y (Lanes X and Y) with (FIG. 34B) the product of an APS-catalyzed polymerization reaction containing 4% or 7% acrylamide and ssDNA methacryl oligos X and Y. The significant increase in apparent size after polymerization with acrylamide indicates incorporation of methacryl oligos into polyacrylamide chains of varying lengths (appearing as a high molecular weight band). FIG. 34C. Polyacrylamide hydrogels formed upon mixing PA-X, PA-Y and a bridge ssDNA sequence, stained by incorporation of gold nanoparticles.

Figure 35:
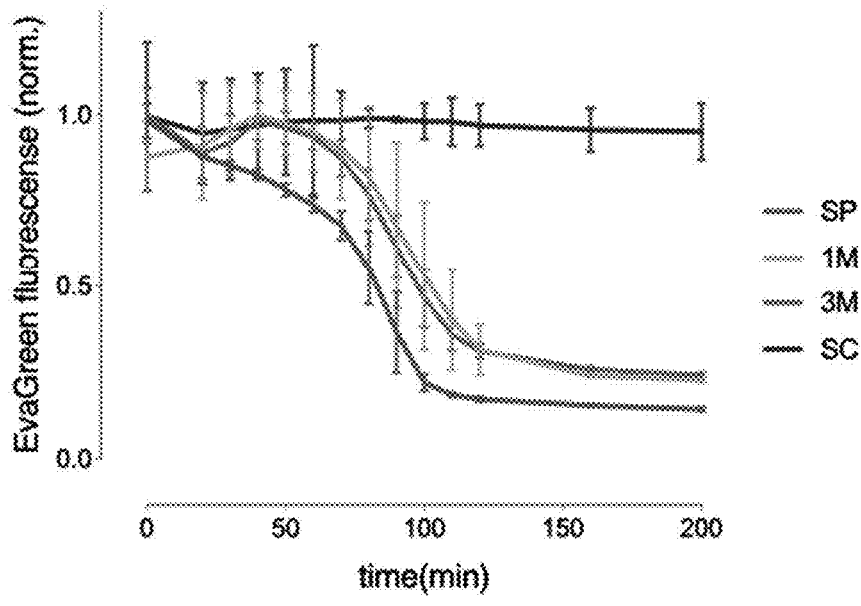

FIG. 35. PA-DNA Hydrogel degradation with mismatched sequences. Cas12a detection specificity was tested for whole-gel degradation reactions using EVAGREEN® (Biotium Inc., Fremont, CA) as an intercalating dye. Specific, perfectly matched dsDNA trigger degraded the gel more efficiently than dsDNA gRNA-Cas12a triggers that contained one or three mismatched bases. A nonspecific dsDNA trigger did not activate gRNA-Cas12a, and the gel did not degrade. Mean and SD are plotted for triplicate experiments.

Figure 36:
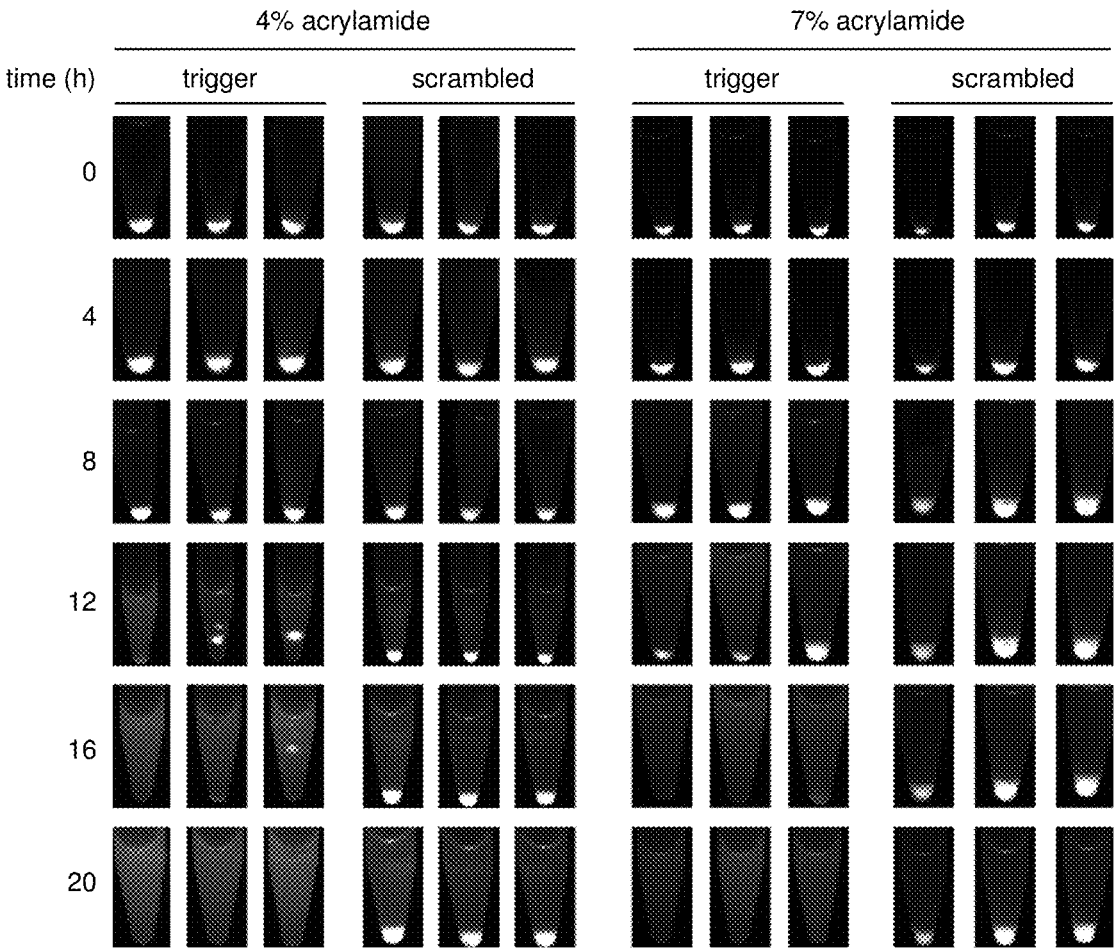
Figure 37E:
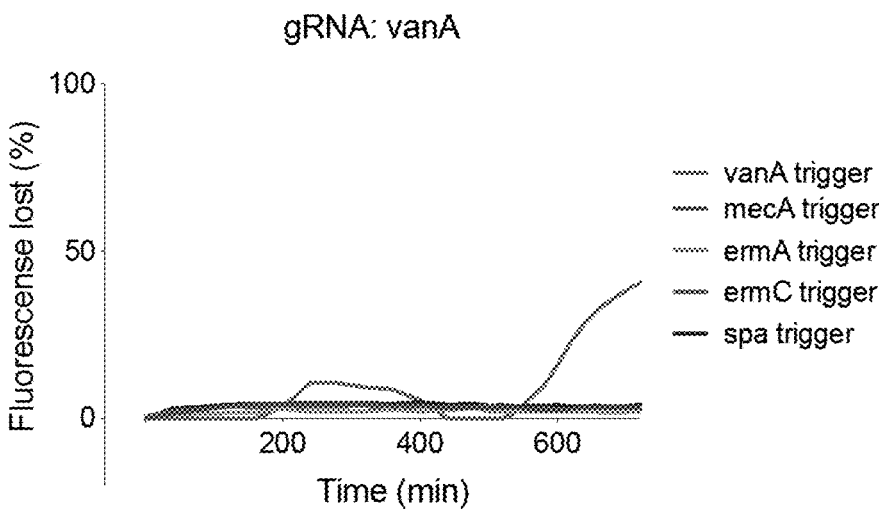

FIG. 36. Degradation of large-scale acrylamide-DNA gels by embedded Cas12a-gRNA. Activation of Cas12a-gRNA with a dsDNA trigger embedded in 4% and 7% acrylamide gels resulted in the degradation of the gel and the release of FITC-dextran into the supernatant (trigger, 20 h bottom row). In contrast, gels embedded with Cas12a-gRNA and a scrambled dsDNA sequence did not degrade, and FITC-dextran remained in the intact gels (scrambled, 20 h bottom row). The gels were incubated at 37° C., inverted and imaged under UV light every 4 h. Increase in gel size at times between 4-8 h was attributed to swelling. The final concentrations of Cas12a and dsDNA trigger or control dsDNA in the reaction (including the supernatant) were 10 nM and 100 nM, respectively. The angle from which gels were imaged varies between time-points in some cases due to changes in the orientation of the tube in the imager.

FIGS. 37A-37E. PA-DNA hydrogel degradation with orthogonal dsDNA triggers. Cas12a detection specificity was tested in whole-gel degradation reactions using EVAGREEN® as a DNA intercalating dye. Five gRNA targeting (FIG. 37A) mecA, (FIG. 37B) ermA, (FIG. 37C) ermC, (FIG. 37D) spa and (FIG. 37E) vanA were tested in pairs with dsDNA triggers corresponding to mecA, ermA, ermC, spa and vanA. Hydrogel degradation occurred only for on-target dsDNA-gRNA pairs. The reactions contained 1 μM Cas12a, 2 μM gRNA and 1 μM dsDNA. Mean and SD are plotted for triplicate experiments.

Figure 38A:
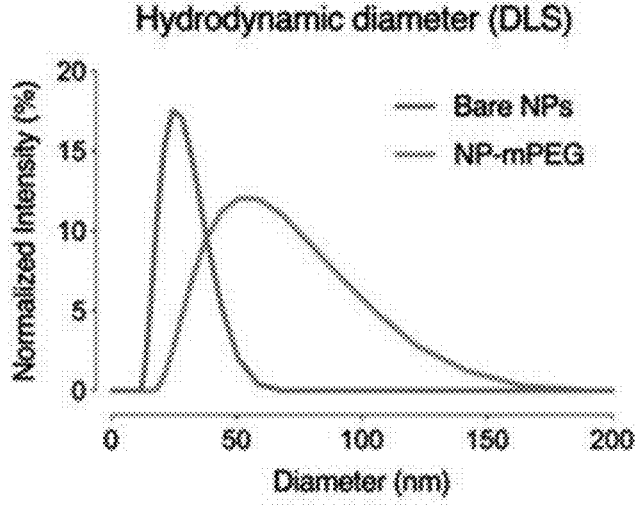

FIGS. 38A-38C. Characterization of nanoparticles encapsulated in PA-DNA hydrogels. (FIG. 38A) Dynamic light scattering, (FIG. 38B) ultraviolet-visible spectroscopy and (FIG. 38C) transmission electronic microscopy (TEM) characterization of gold nanoparticles (NPs) before and after mPEG conjugation. Synthesized bare NPs were 18.4±2.2 nm in diameter, as measured by TEM (N=988). The position of the surface plasmon resonance peak of the NPs (521 nm) did not change after conjugation with mPEG, indicating that the NPs did not aggregate. Upon mPEG conjugation, the hydrodynamic diameter of NPs increased (as synthesized $D_H=24$ nm; after mPEG conjugation $D_H=50$ nm), confirming the attachment of high molecular weight mPEG (n=3). Scale bar is 50 nm.

Figure 39C:
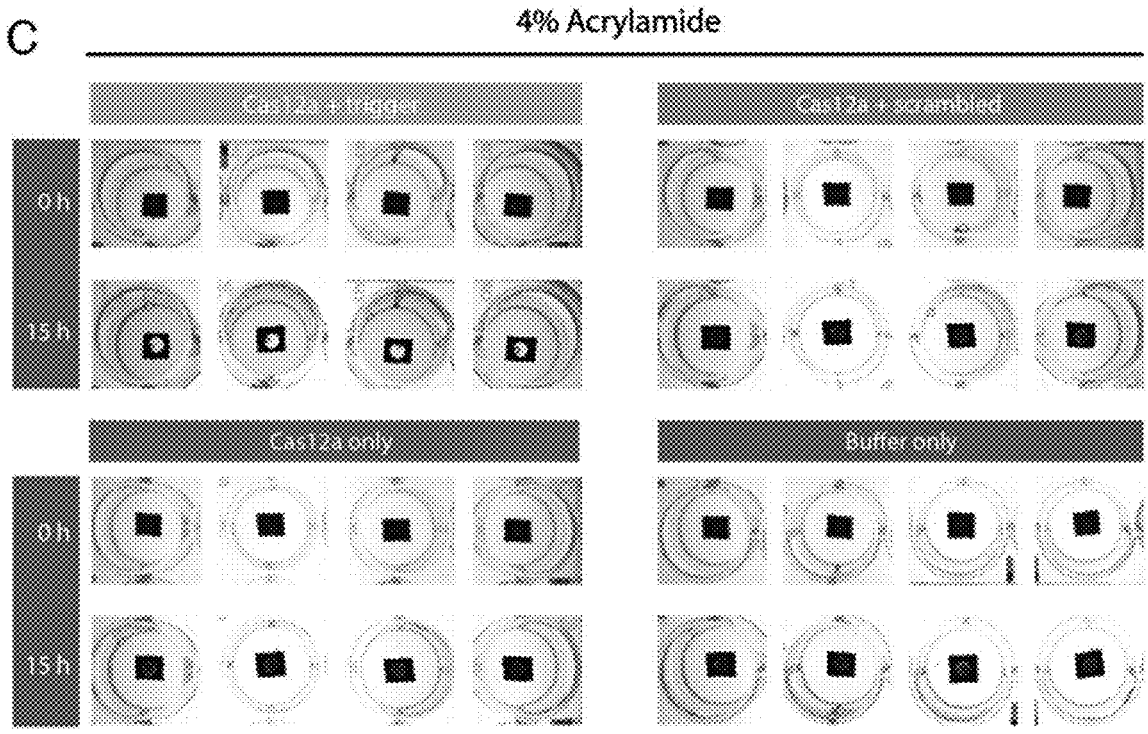
Figure 39D:
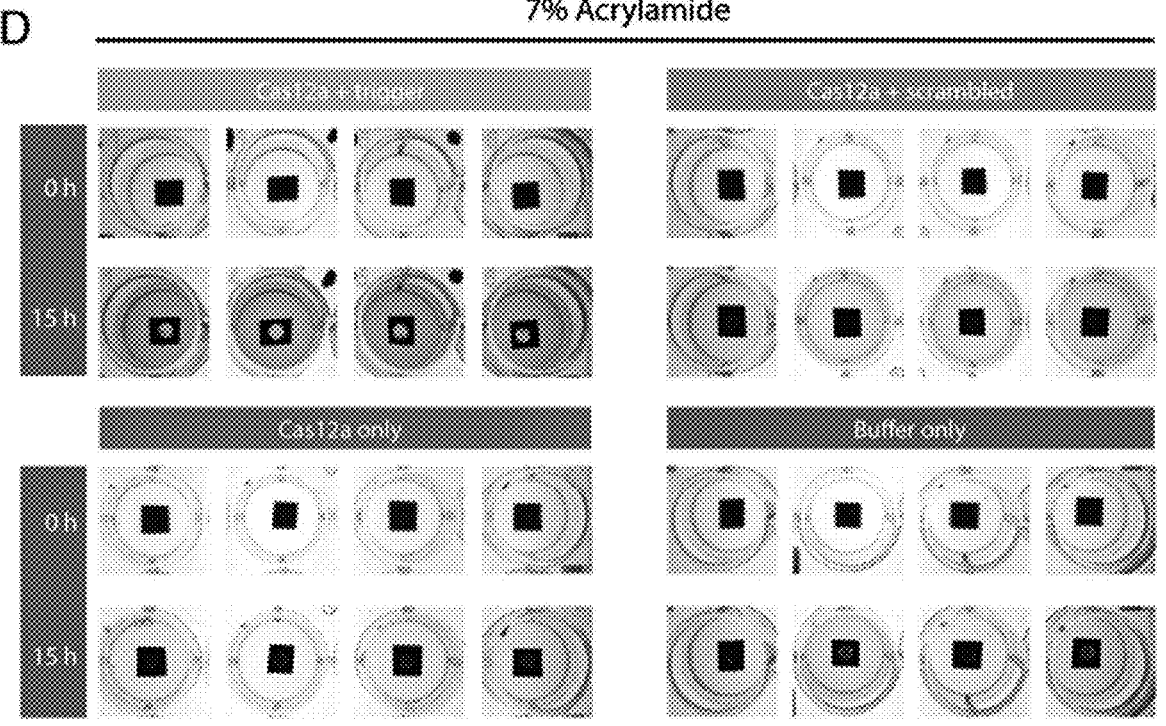

FIGS. 39A-39D. Polyacrylamide-DNA hydrogels of different acrylamide concentration release AuNPs and exhibit different baseline release rates. FIG. 39A. AuNPs are released upon addition of Cas12a-gRNA and target dsDNA trigger. Mean and SD are plotted for four replicate experiments. FIG. 39B. Release comparison at t=15 h between 7% (FIG. 2D) and 4% acrylamide show that higher hydrogel percentages lead to lower nonspecific release of AuNPs. For both 4% and 7% PA-DNA gels, one-way ANOVA followed by Tukey's post hoc test indicated significant differences between the trigger and all three controls (p<0.0001), and no significant difference amongst the three controls (p>0.5). The differences in means between 4% and 7% PA-DNA gels for each condition were assessed by Bonferroni-corrected multiple t-tests. There was no significant difference between samples containing dsDNA triggers (p>0.99) and for the three controls the mean background release was significantly higher in 4% gels than in 7% gels (p<0.03). Images of hydrogels in silicone isolators in the center of 24-well tissue culture plates at (FIG. 39C) 4% polyacrylamide and (FIG. 39D) 7% polyacrylamide before and after 15 h for gels containing Cas12a-gRNA+dsDNA trigger, Cas12a-gRNA+ scrambled dsDNA, Cas12a-gRNA or buffer only. In all images, the loaded gels are submerged in 850 µl 1×NEB 2.1 buffer.

Figure 40:
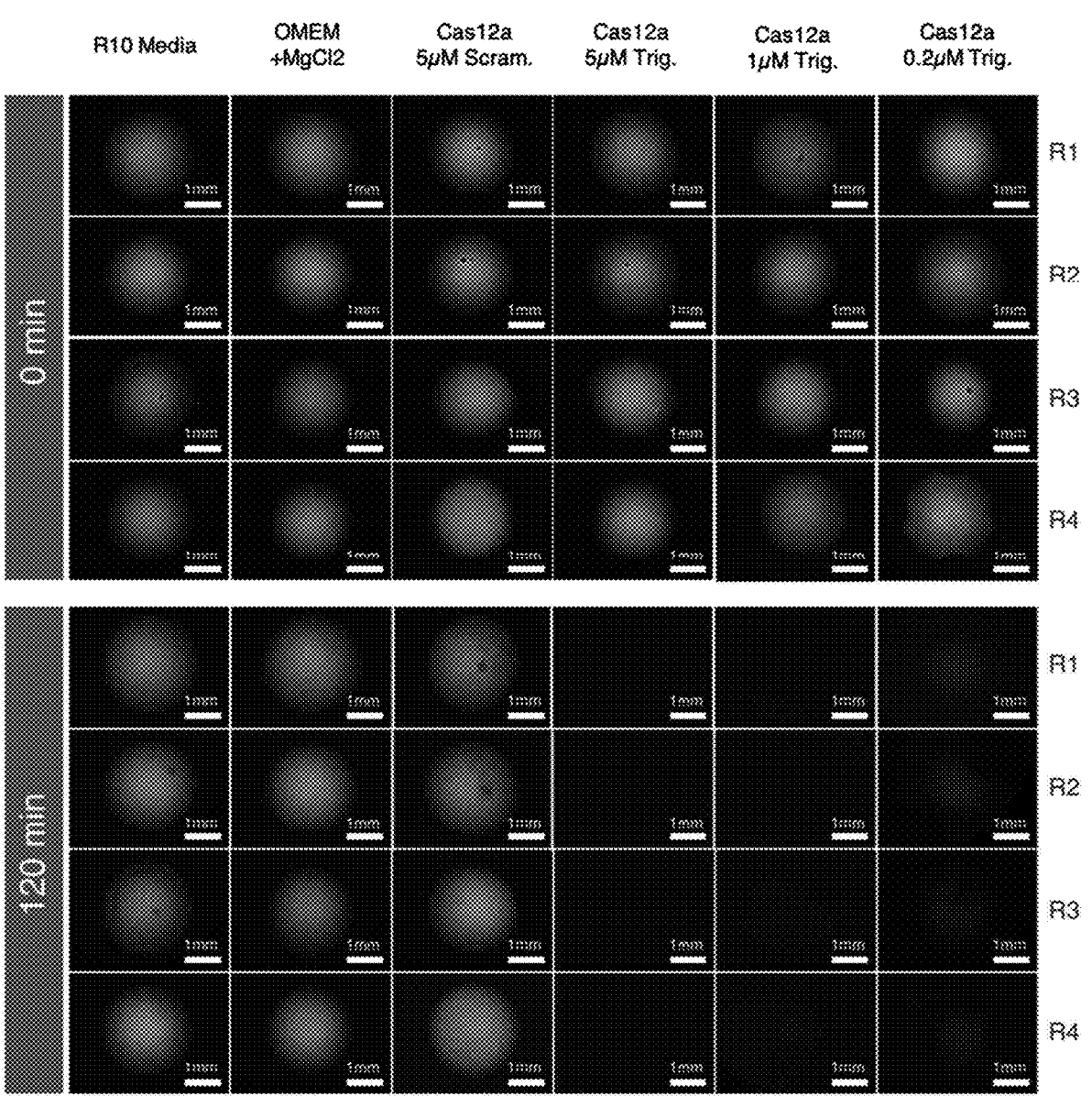

FIG. 40. Cell release from PA-DNA hydrogels. Human primary peripheral blood mononuclear cells (PBMCs) were encapsulated into PA-DNA hydrogels. Replicates (n=4) for six different solution conditions are shown before and after a 120-min incubation with a mixture of Cas12a-gRNA and dsDNA. Gel degradation is visible after 2 h in all the incubation conditions that included an on-target dsDNA trigger (+Trig). Little to no hydrogel degradation was observed in R10 medium (RPMI+10% FBS), OMEM medium with 10% FBS and 10 mM $MgCl_2$ (OMEM+ MgCl2), and OMEM, 10 mM $MgCl_2$, and Cas12a-gRNA with an off-target (Scram.) dsDNA during the 120 min incubation. Scale bars are 1 mm. PBMC viability after hydrogel degradation is shown in FIGS. 41A-41C, while PBMC viability in bulk Cas solution is shown in FIGS. 42A-42B.

Figure 41A:
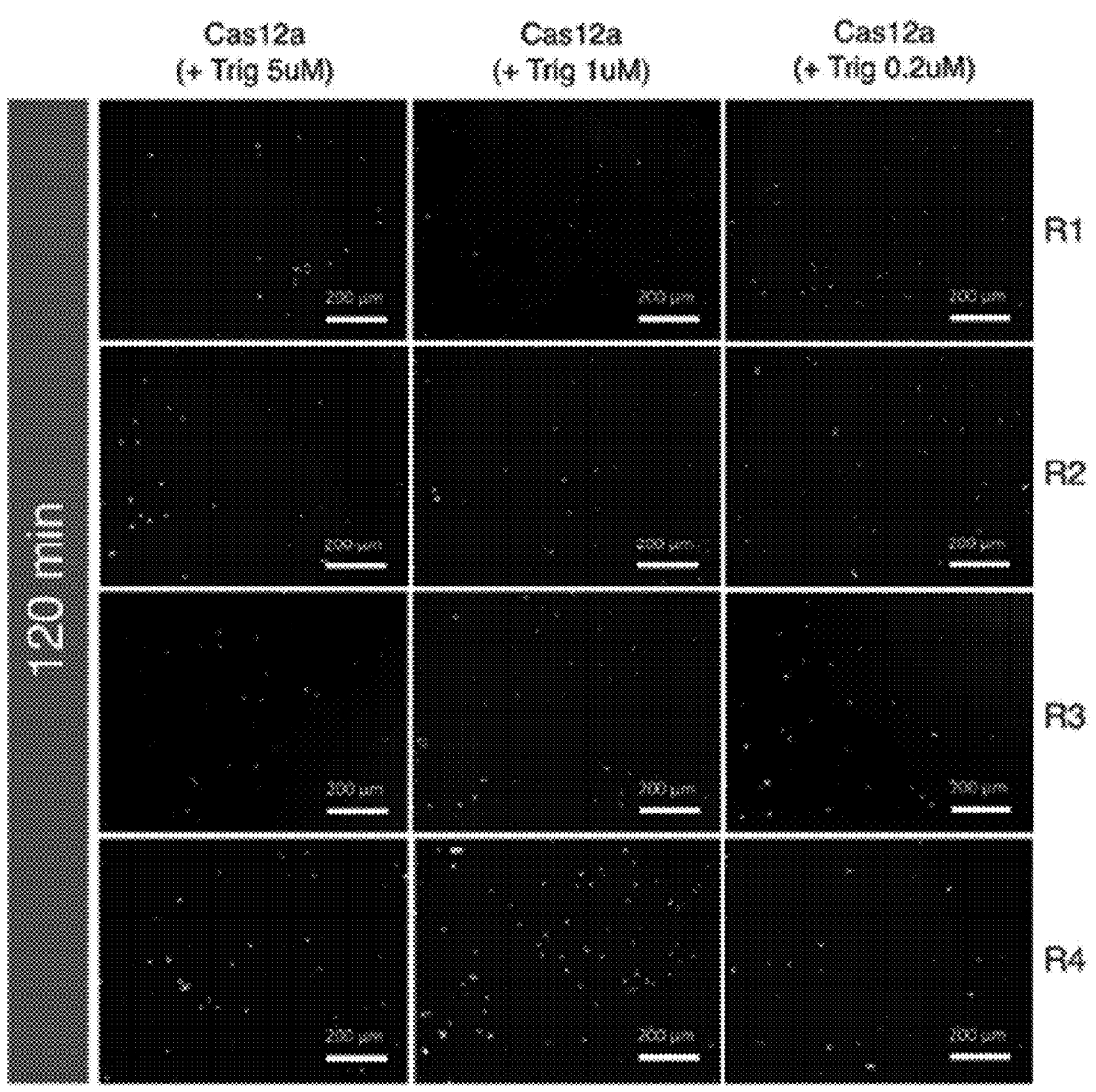
Figure 41B:
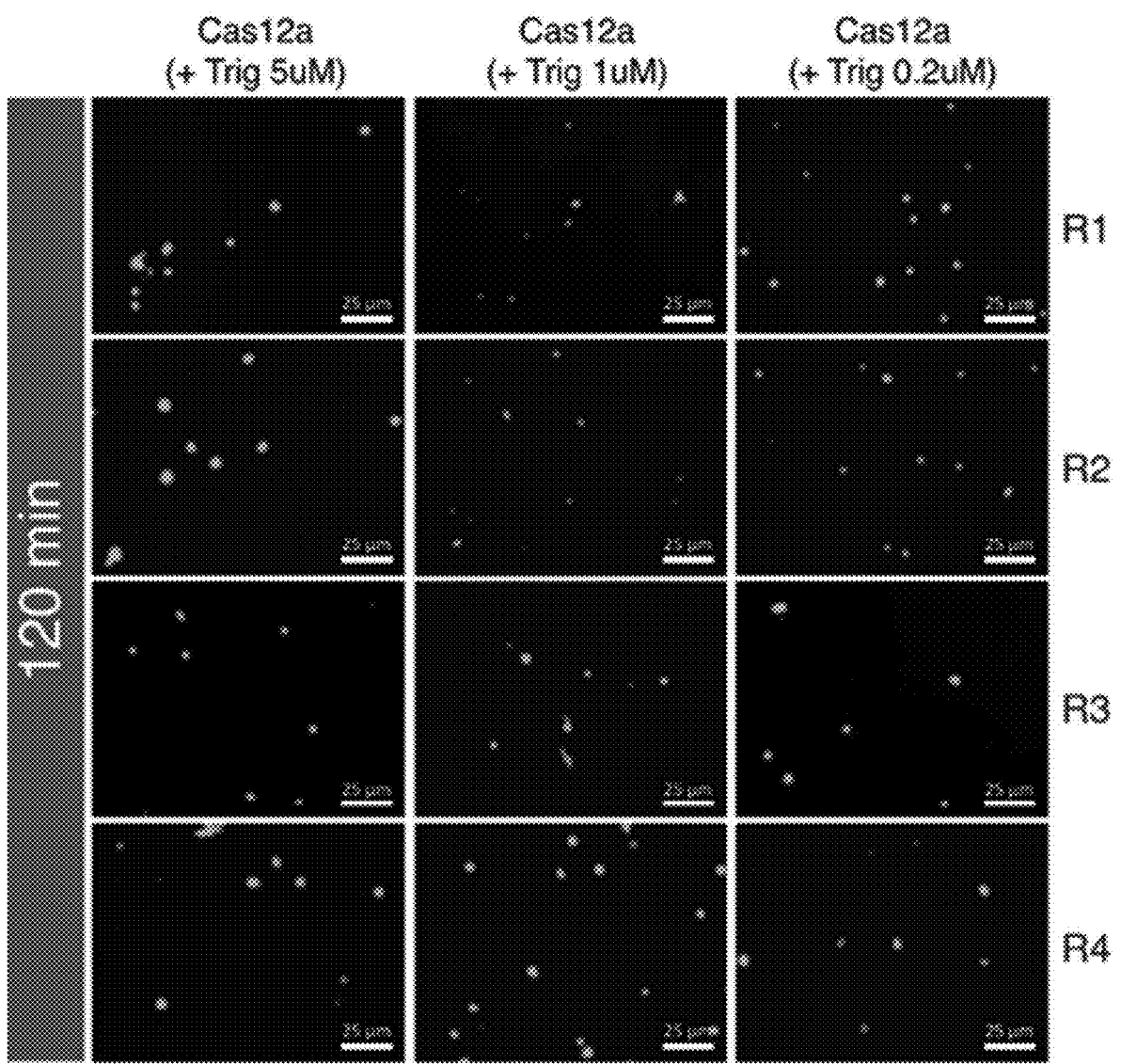
Figure 41C:
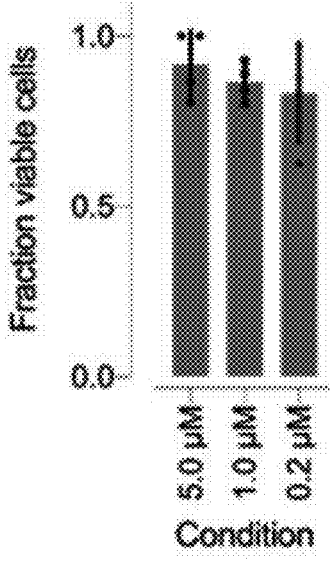

FIGS. 41A-41C. Viability assay of released primary PBMCs from PA-DNA hydrogels. Experiment following the cell release (t=2 h) from PA-DNA hydrogels from FIG. 40. After hydrogel degradation live-dead stain was added to the wells and released cells were imaged. FIG. 41A. Image overlays acquired with a 20× objective. FIG. 41B. Digitally zoomed sections of corresponding wells. Cells were stained for viability using calcein blue-AM (live) and ethidium homodimer-1 (dead). Most cells were viable (blue) after release from hydrogels. FIG. 41C. Quantification of the cell counts from the replicates in (FIG. 41A) using ImageJ. Total number of cells counted: 5.0 µM, 172; 1.0 µM, 270; 0.2 µM, 204. One-way ANOVA p=0.55 for differences in the means.

Figure 42A:
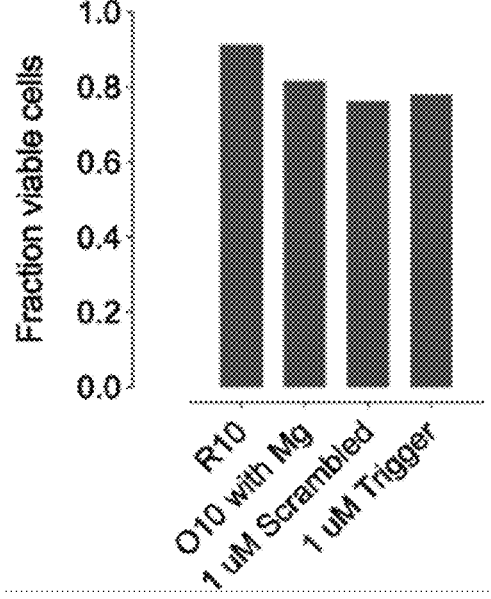
Figure 42B:
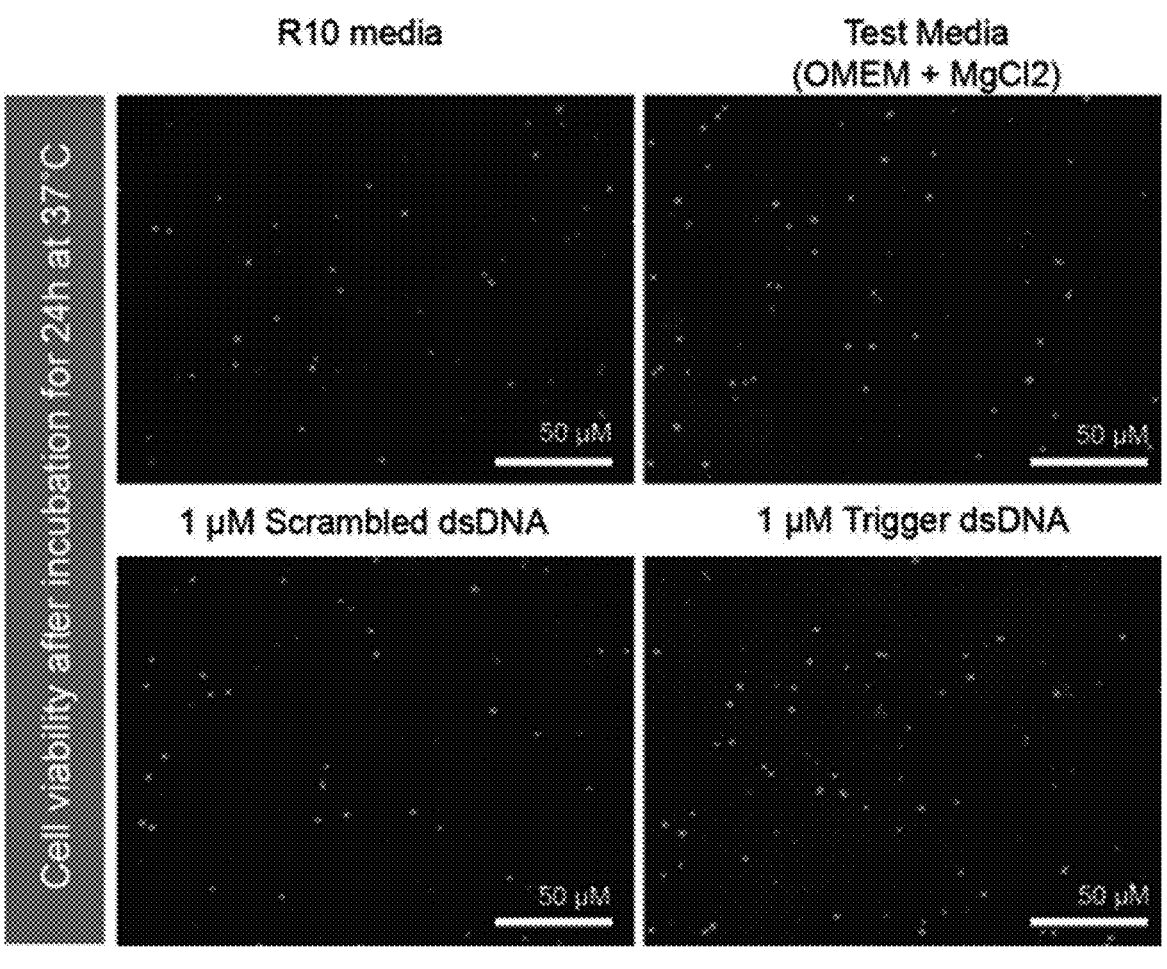

FIGS. 42A-42B. Primary cell viability in Cas12a solution. FIG. 42A. Quantification of the viability of human primary peripheral blood mononuclear cells (PBMCs) after 24 h incubation in a Cas12a solution. For each condition, n>130 cells were counted across two replicates (R10: 138 cells; O10 test media: 196 cells; scrambled dsDNA: 198 cells; trigger: 186 cells). R10 contained RPMI and 10% FBS, O10 test media contained OMEM media, 10% FBS and 10 mM $MgCl_2$; TM+Scr and TM+Trig contained O10 test media with 0.5 µM Cas12a. 1 µM gRNA, 0.1×NEBuffer 2.1 and 1

µM scrambled or trigger dsDNA, respectively. FIG. 42B. Representative imaging of PBMCs showing live and dead cells after 24 h incubation in activated Cas12a (Cas12a-gRNA with specific trigger), inactive Cas12a (Cas12a-gRNA with nonspecific trigger) and media-only solutions. Scale bar is 50 µm.

Figure 43A:
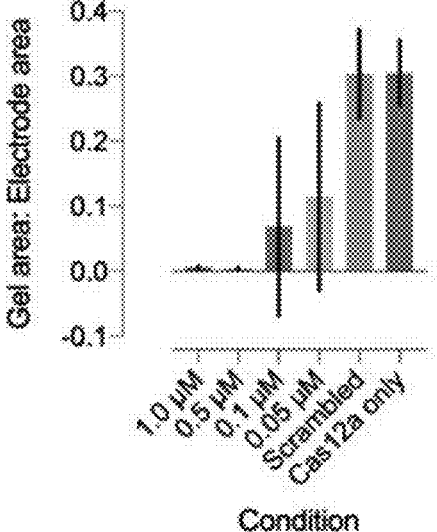
Figure 43B:
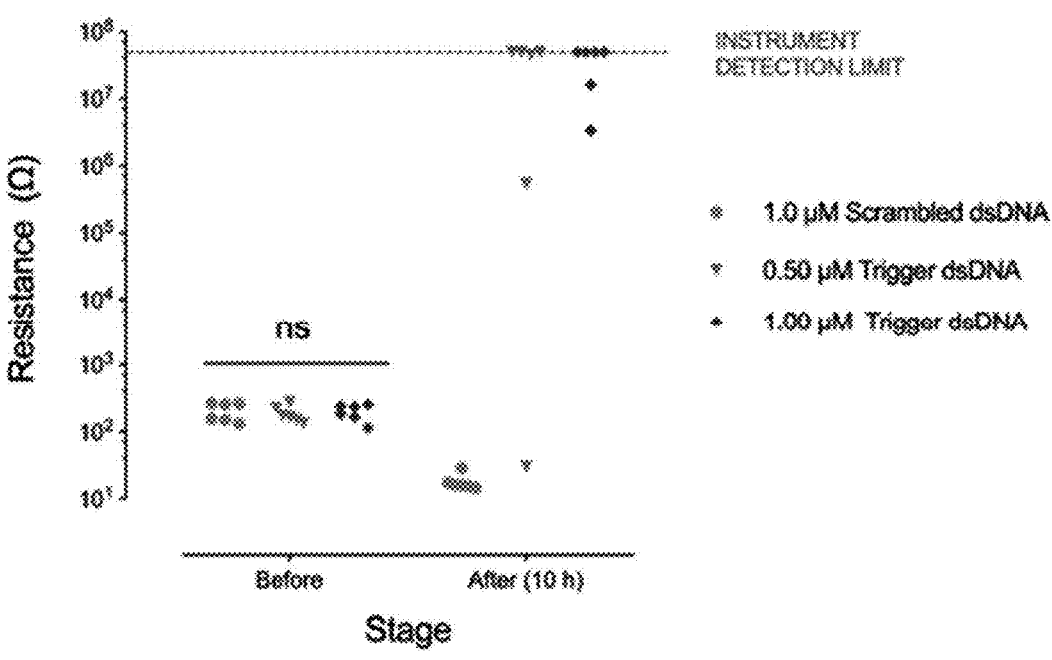
Figure 43C:
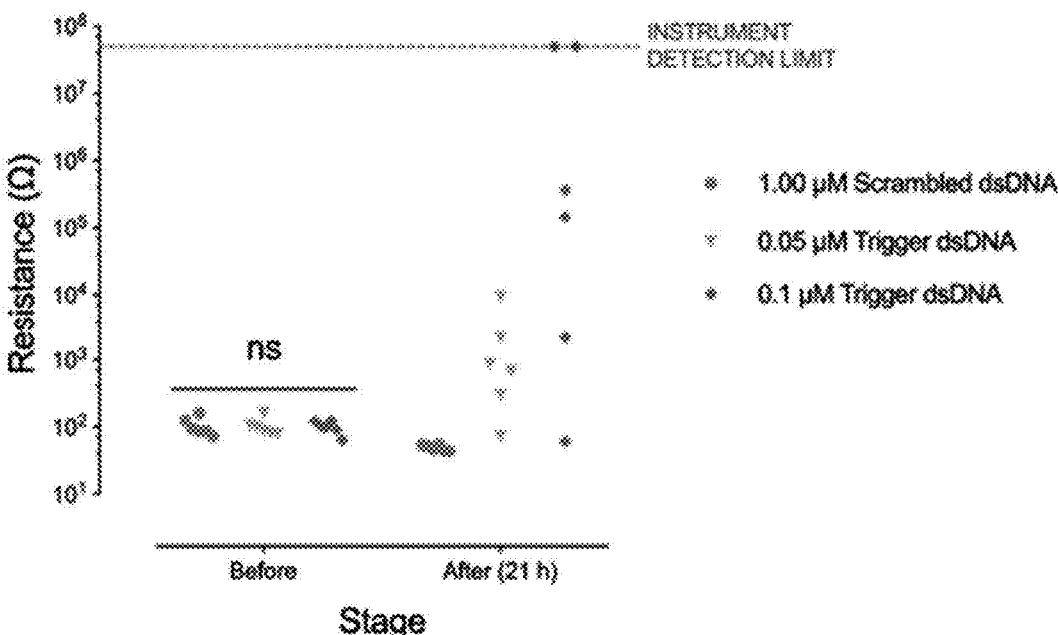
Figure 43D:
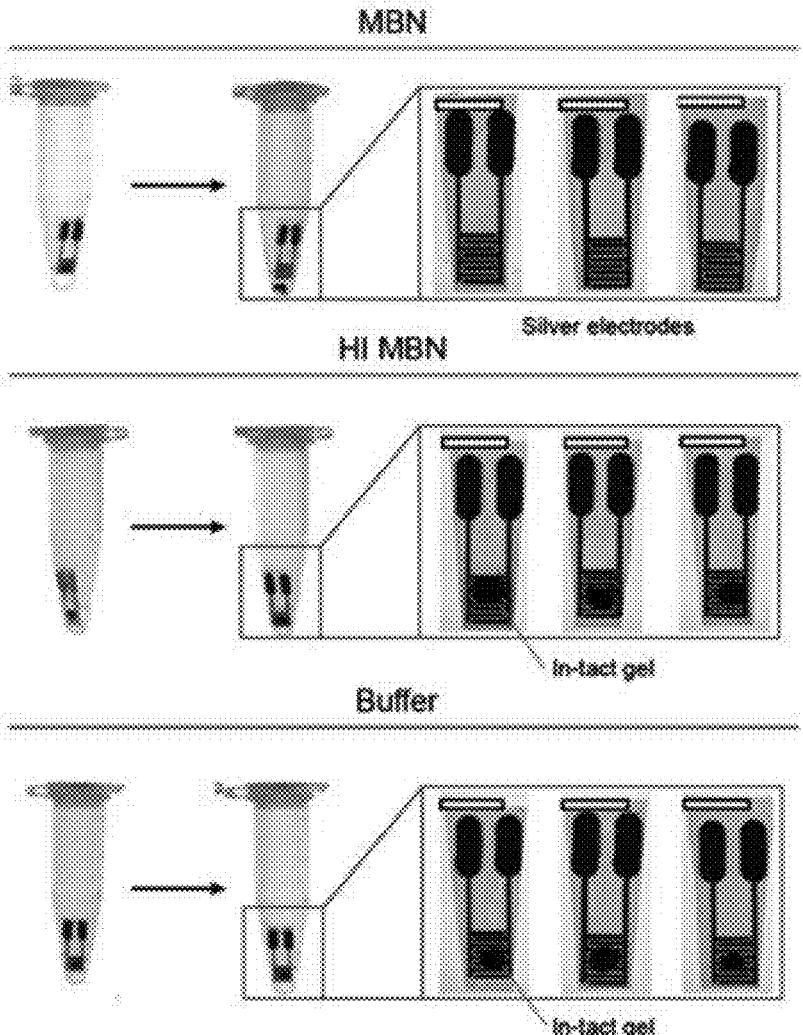
Figure 43E:
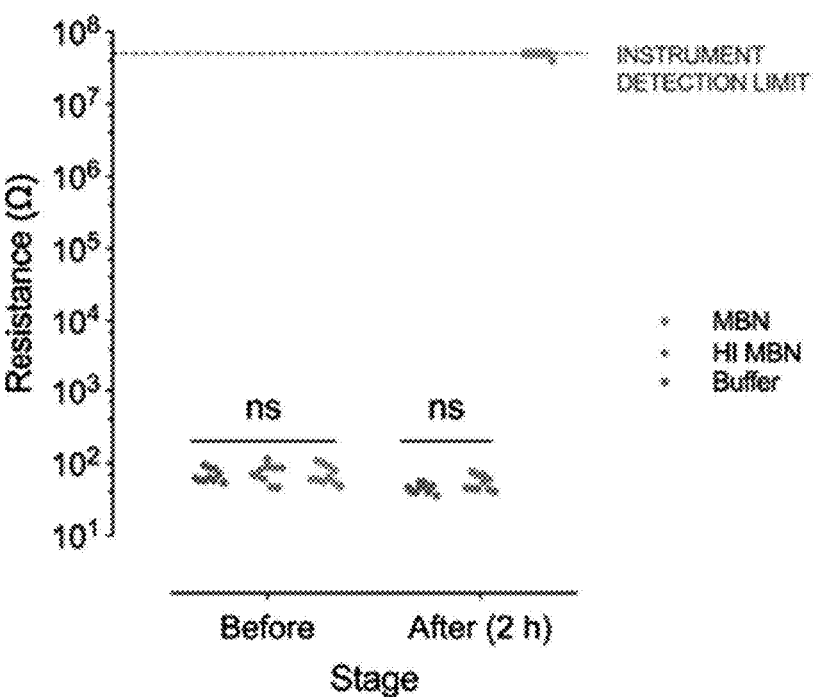

FIGS. 43A-43E. CB-DNA hydrogel degradation. FIG. 43A. Gel area was quantified relative to electrode area for the electrodes presented in FIG. 19D. The analysis was performed on ImageJ by measuring pixel counts on each photograph. FIG. 43B. CB-DNA hydrogels were incubated with Cas12a-gRNA and 1 µM and 0.5 µM dsDNA trigger. After 10 h, the electrodes were dried and their electrical resistance was measured. Initial resistance measurements were not significantly different based on a Kruskal-Wallis test with Dunn's post hoc multiple comparison (adjusted p>0.99). Post-incubation, a similar analysis showed a significant difference between the control and both trigger conditions (p<0.016), but no significant difference between the two dsDNA concentrations (p>0.99). FIG. 43C. CB-DNA hydrogels were incubated with Cas12a-gRNA and 0.1 µM and 0.05 µM trigger dsDNA and resistance was measured after 21 h. Initial resistance measurements were not significantly different based on a Kruskal-Wallis test with Dunn's post hoc multiple comparison (adjusted p>0.99). Post-incubation, a similar analysis showed a significant difference only between the 0.1 µM dsDNA trigger condition and the control (p=0.0013). FIG. 43D. Representative images of the electrodes in FIG. 43E. The ssDNA-specific Mung Bean nuclease (MBN) was used as a positive control for CB-hydrogel degradation. CB-DNA hydrogels were detached from the electrodes after 2 h in a MBN solution while heat-inactivated (HI) MBN did not detach the hydrogels. Scale bar is 3 mm. FIG. 43E. Conductivity measurements for the electrodes in the experiment in FIG. 43D, with n=10 for each condition. Initial resistance measurements for the electrodes in FIG. 43D were not significantly different based on a Kruskal-Wallis test with Dunn's post hoc multiple comparison (adjusted p>0.99). Post-incubation, the MBN treatment was significantly different from the two controls (p<0.0001), while the two controls were not significantly different from each other (p>0.99).

Figure 44A:
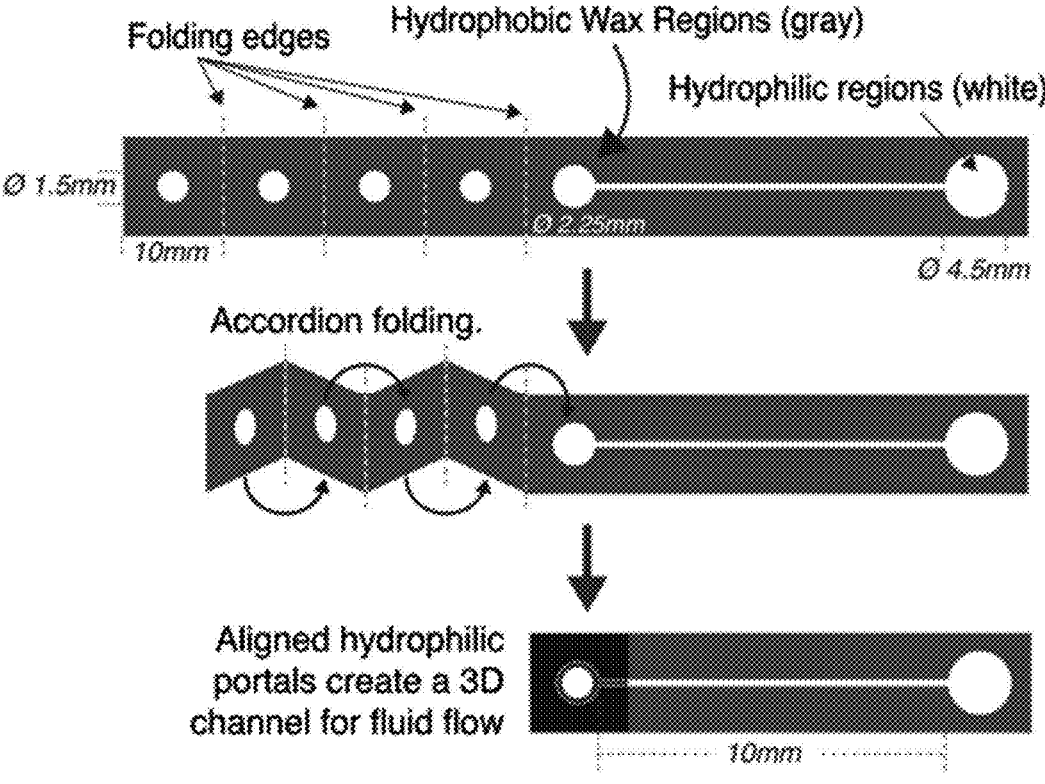

FIGS. 44A-44C. PA-DNA hydrogel resistor µPAD format and device. FIG. 44A. Dimensional details of a single µPAD wax inkjet printing pattern. The folding process outlined was performed once the different components had been added to their respective layers. FIG. 44B. An assembly and testing schematic for electrical resistance measurements of the Cas12a-mediated permeability assay in the µPAD. FIG. 44C. Photograph of assembled µPAD used for Cas12a-mediated permeability testing.

FIG. 45. Cas12a cutting of 100 µM ssDNA Linker in conjunction with 750 nM quenched fluorescent ssDNA. Increasing levels of trigger DNA lead to increased fluorescent signal, which indicates an increased collateral cleavage activity of ssDNA content in solution, including the ssDNA linker used in PA-DNA gelation. The ssDNA reporter had the sequence: 5' (6FAM)-TTATT-(Iowa Black™ FQ) 3'.

Figure 46:
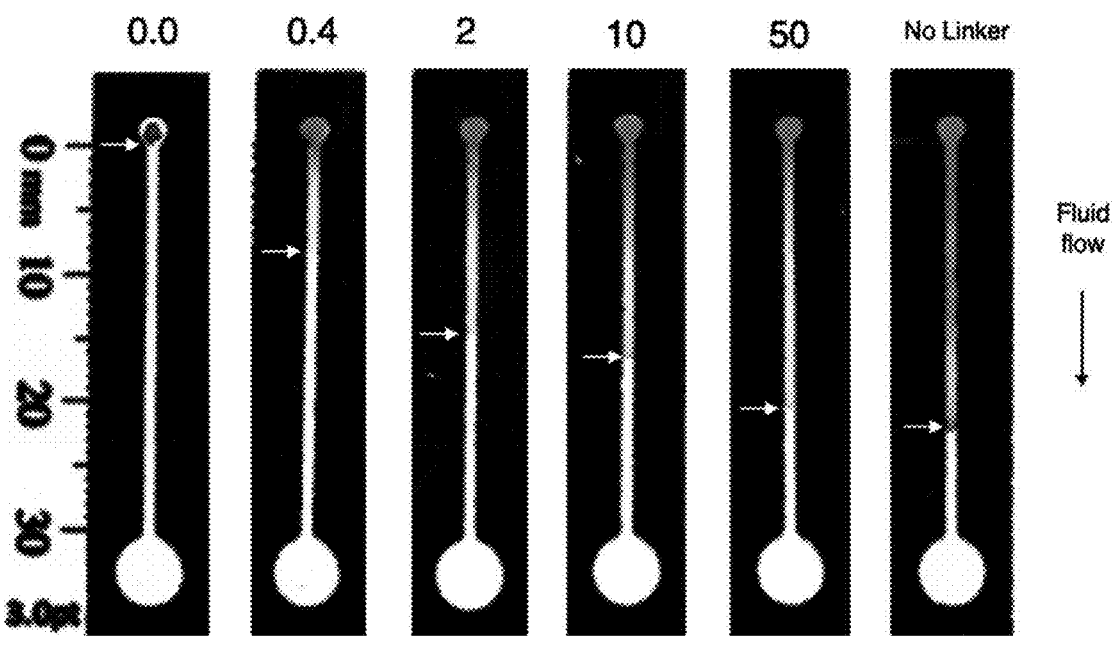

FIG. 46. PA-DNA hydrogel µPAD as a fluidic capillary resistor. Representative µPAD channel buffer wicking lengths at the 5-min endpoint. µPADs were filled with 0.3 µl of DNA linker (100 µM) pre-incubated for 4 h at 37° C. in a cutting solution containing Cas12a (300 nM), MRSA gRNA (1 µM), dsDNA MRSA Trigger (0 nM, 0.4 nM, 2 nM, 10 nM, 50 nM) and 1×NEB Buffer 2.1.

Figure 47:
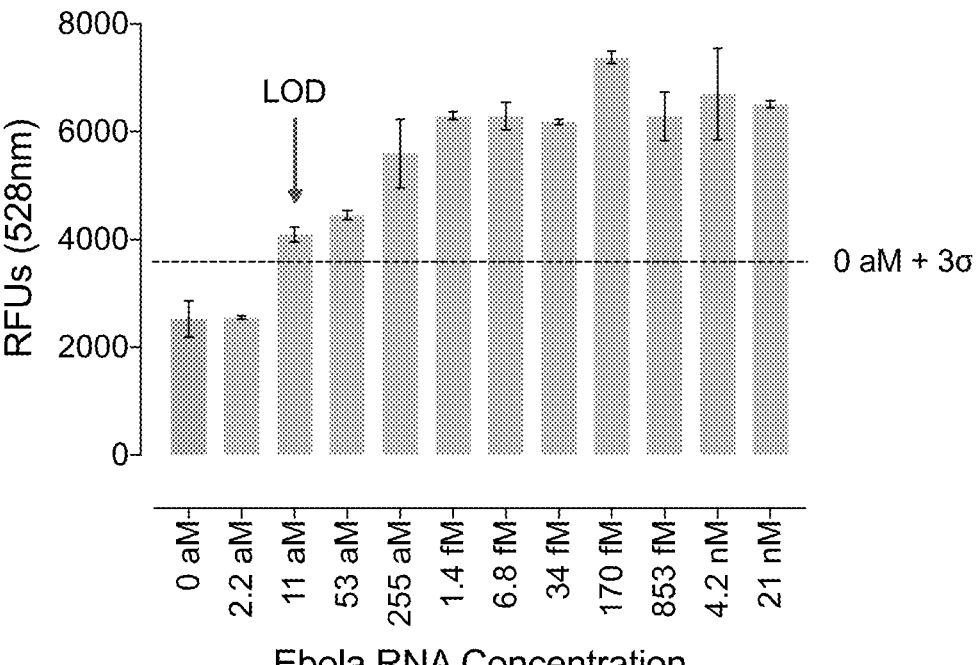

FIG. 47. Verification of Cas12a EBOV detection system. In-solution readouts from RT-RPA reactions (0 aM, 2 aM, 11 aM, 53 aM, 255 aM, 1.4 fM, 6.8 fM, 34.1 fM, 170 fM, 853 fM, 4.2 nM and 21 nM EBOV RNA trigger). Final concentrations of 50 nM Cas12a: 62.5 nM gRNA: 750 nM FQ reporter in 1×NEB 2.1 buffer were added to 50 µl of RT-RPA reactions. Student's t-test p=0.0017 for a difference in the means of the 0 and 11 am ssRNA samples. Reactions (3 µl, 384-well microplate) were incubated at 37° C. for 2 h and fluorescence was recorded in a plate reader (Biotek NEO HTS) (Ex: 485 nm; Em: 535 nm). The ssDNA reporter had the sequence: 5' (6FAM)-TTATT-(Iowa Black™ FQ) 3'. Mean and SD are shown for triplicate experiments.

Figure 4A:
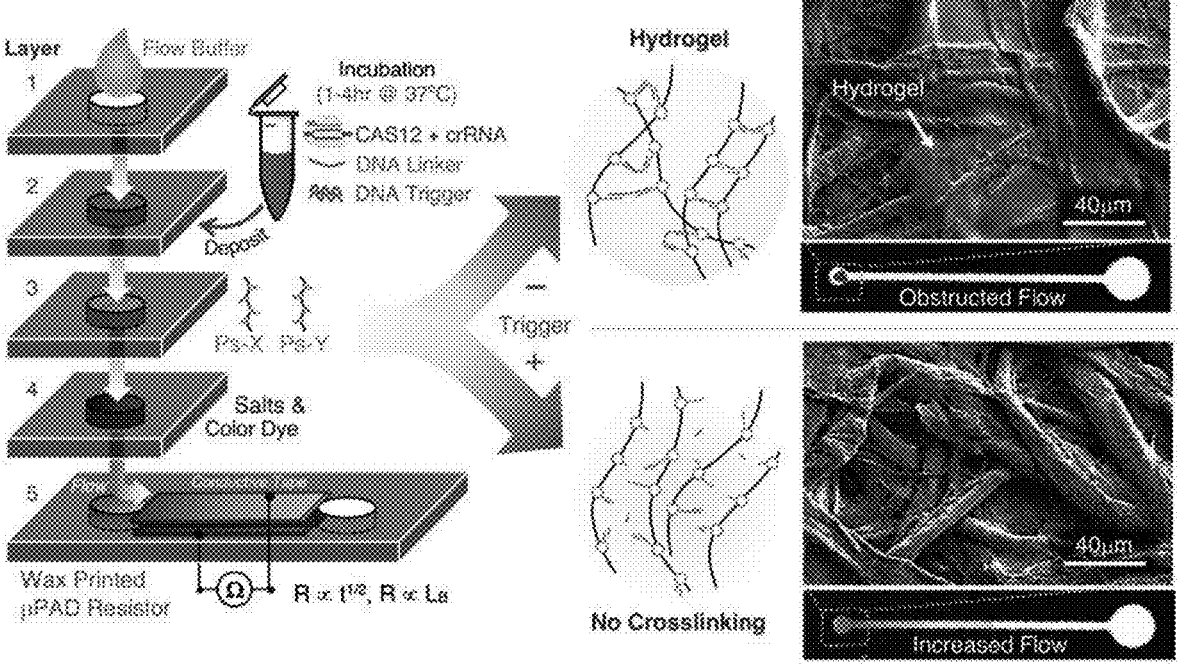
FIGS. 4A-4F. An electronic sensor based on controlling the permeability of a paper-based microfluidic device (μPAD) using Cas12a-mediated pre-digestion of hydrogel precursors.
Figure 4B:
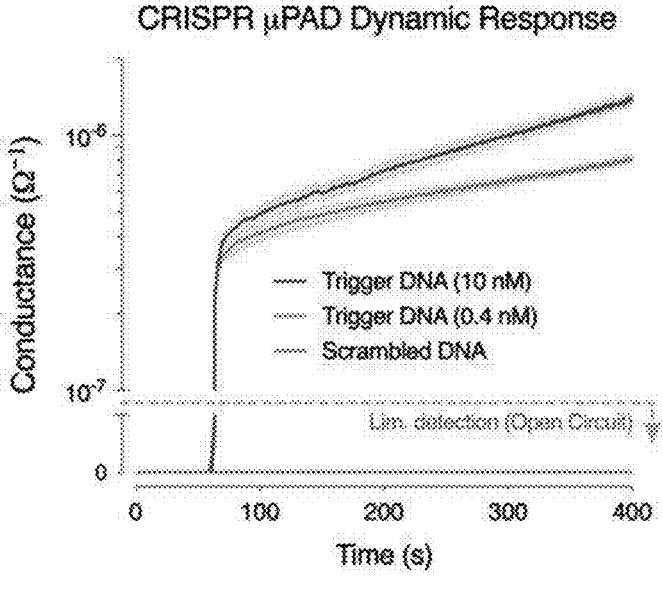
Figure 4C:
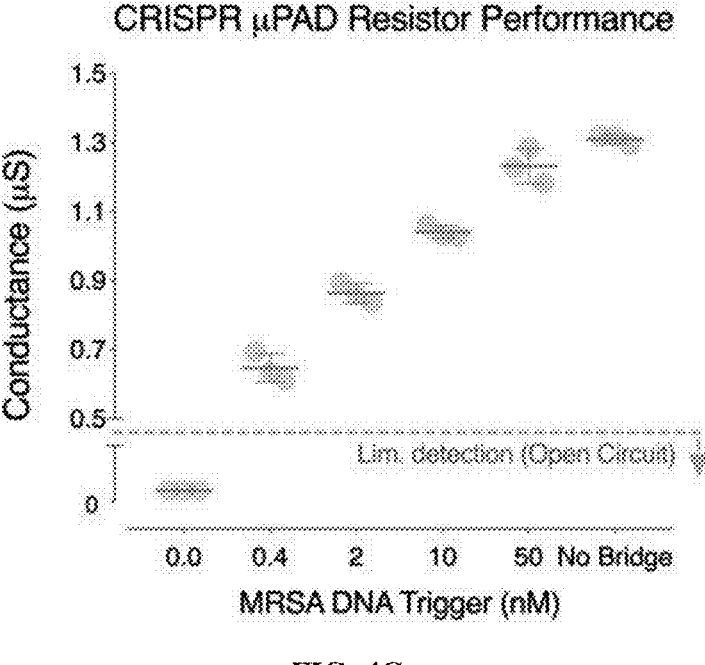

FIGS. 48A-48D. Measurements of µPAD channel electrical conductance and RFID activation for different concentrations of dsDNA MRSA trigger. FIG. 48A. Real-time measurement of electrical resistance of MRSA PAD lateral flow sensors with 4% (w/v) acrylamide for two different concentrations of dsDNA MRSA Trigger (0.4 nM, 10 nM) and scrambled DNA (10 nM) (mean±SD for n=3). Cas12a collateral cleavage reaction mix was deposited containing ssDNA gel linker (10 µM) after 4 h pre-digestion incubation. Results of 5-min electrical-conductance endpoints from similar experiments are shown in FIG. 4C. FIG. 48B. The Cas12a collateral cleavage reaction mix containing ssDNA gel linker (10 µM) was deposited on a 7% (w/v) acrylamide MRSA µPAD after 1 h pre-digestion incubation. The use of a higher polyacrylamide percentage created a higher viscosity precursor which required less ssDNA linker to generate flow-impeding gelation. As a result, this ssDNA linker could be cut sufficiently with reduced pre-incubation times (1 h as opposed to 4 h). Overall system sensitivity to increasing levels of dsDNA trigger appears to be reduced compared to PA-DNA µPAD using hydrogel precursors produced with 4% (w/v) acrylamide shown in FIG. 20C. NC=scrambled dsDNA trigger (10 nM). FIG. 48C. Schematic of operation of Cas12a-activated µPAD RFID device without reference tag. This example used a 4 layer µPAD without the lateral flow channel for operation, as opposed to the device used in FIGS. 20A-20E which contained a section of the lateral flow Layer 5 and a reference RFID tag. FIG. 48D. Characteristic signal trace of the MRSA CRISPR-µPAD RFID sensor in the presence of a dsDNA Trigger and a scrambled control sequence.

FIG. 49. Diagnostic results from an experimenter-blinded trial of the µPAD RFID system. Samples (S1-12) containing either 0 aM (negative, n=6) or 11 aM (positive, n=6) EBOV ssRNA trigger were amplified by RT-RPA, incubated with the ssDNA gel bridging and Cas12a-gRNA strand for 4 h, and assayed on a µPAD-RFID device. The corresponding time traces for the RFID output are shown adjacent to the samples. The diagnostic decision was based on the RFID traces themselves, where an increase in the Δ|RSSI| (dB) after ~50s indicates a positive result (the presence of EBOV ssRNA in the original sample). Increase in signal strength was defined for the test tag in relationship with an attached reference RFID tag, where a complete loss of test tag RFID signal led to a sudden increase in the calculated Δ|RSSI|. The measurement of the twelve samples was divided over three different sites, with the UHF RFID antenna, µPADs and the computer used for signal processing transported between sites by the experimenter.

DETAILED DESCRIPTION

Microbial clustered regularly interspaced short palindromic repeats (CRISPR) and CRISPR-associated (Cas) adaptive immune systems contain programmable RNA-guided endonucleases, some capable of multiple-turnover kinetics (1, 2). Due to their specificity, programmability, and enzymatic activity, CRISPR-Cas have been exploited as efficient genome editing tools (3), and more recently in diagnostic applications such as SHERLOCK (4, 5) and DETECTR (2). However, the use of CRISPR system components for effecting multiscale, programmable changes in the physical properties of macroscopic materials such as hydrogels remains unexplored.

Figure 1:
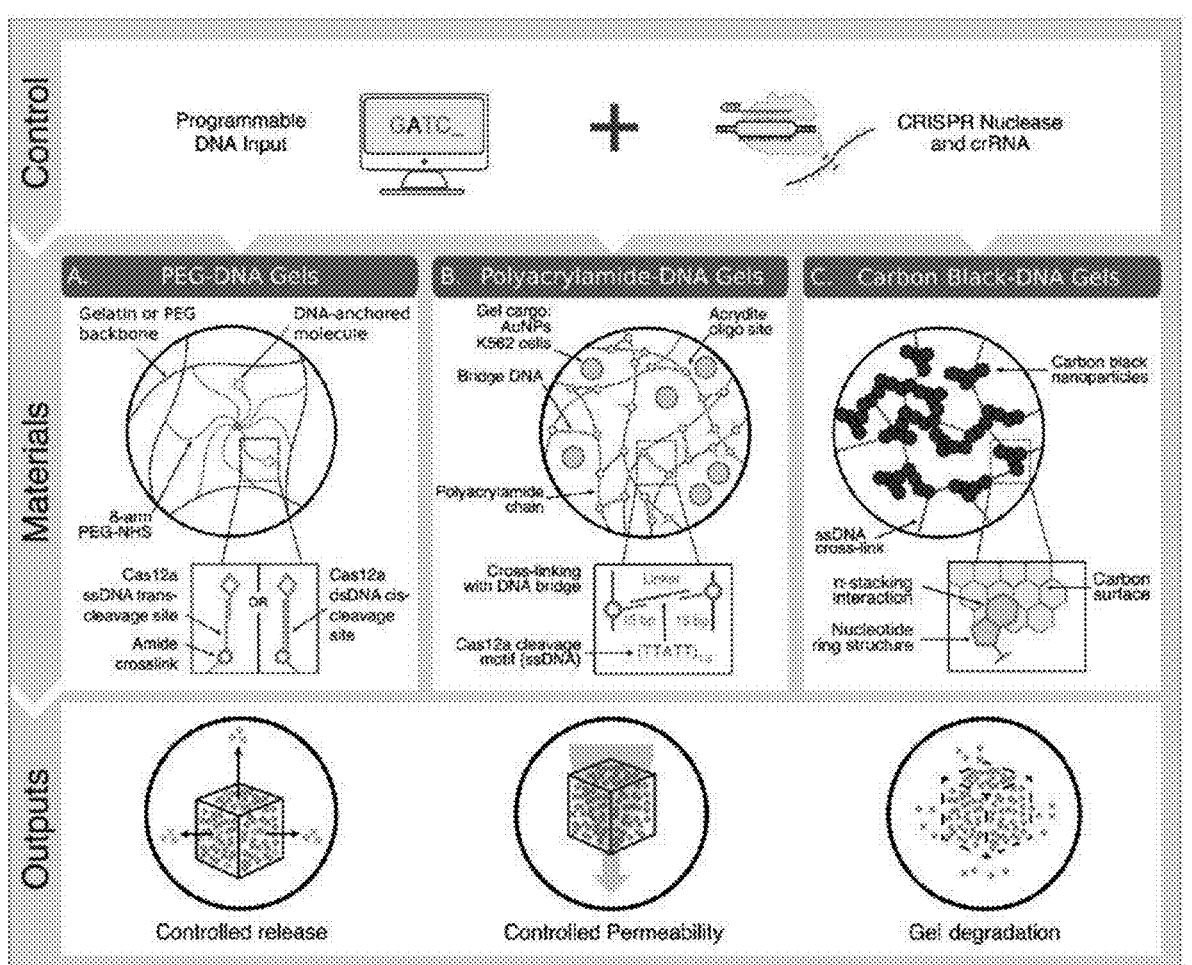
FIG. 1. CRISPR-mediated DNA-hydrogel modulation. RNA-guided Cas endonucleases can be easily programmed for specific DNA inputs (top panel) and used in combination with different hydrogel chemistries (middle panel) to modulate system properties at multiple scales, such as controlled release of molecules, particles. or live cells; fluid permeability; and bulk material degradation (bottom panel). Three basic CRISPR-gel systems were explored: (A) branched polyethylene glycol-based hydrogels for release of DNA-anchored compounds; (B) degradable polyacrylamide-DNA hydrogels for release of encapsulated payloads (e.g., particles or live cells), as well as for controlling permeability of microfluidic systems via cleavage of a hydrogel ssDNA linker; and (C) conductive carbon black-DNA hydrogels for electrical circuit bridging with fuse-like responsiveness to dsDNA trigger activation. All presented CRISPR-gels respond to activation of a Cas12a-crRNA complex through the presence of a dsDNA trigger, and are designed to leverage either the highly-specific dsDNA cis-cleavage activity of Cas12a for multiplexed response or the high-turnover ssDNA trans-cleavage activity of Cas12a to modulate large-scale hydrogel properties.

As disclosed herein, CRISPR system components were used to control the properties of DNA-based hydrogels at multiple scales (from targeted payload release to bulk gel actuation) and in a modular fashion by eliminating the need to encode sequence specificity into the gel structure itself. Different hydrogels were engineered to demonstrate a variety of triggered responses for use in therapeutic, diagnostic and sensing applications, including the release of small molecules, nanoparticles (NPs), and live cells, as well as for the modulation of bulk electrical and permeability properties of DNA-hydrogels (FIG. 1).

Hydrogel Compositions

In some aspects the disclosure relates to hydrogels. As used herein, the term "hydrogel" refers to three-dimensional polymeric network structure which can absorb and retain water. The hydrogels described herein may comprise a plurality of structural components (i.e., polymer chains), which may differ chemically. For example, a hydrogel my comprise polyacrylamide chains, polyethylene glycol chains, gelatin, fibrillary proteins, or a combination thereof. However, at least one structural component of each of the hydrogels described herein is a polynucleotide-based structural component (i.e., "a nucleic acid molecule component"). Of the total structural components of a hydrogel, the percentage that are nucleic acid molecule components may vary. For example, in some embodiments, at least 1, at least 2, at least 3, at least 4, at least 5, at least at least 7, at least 8, at least 9, at least 10, at least 15, at least 20, at least 25, at least 30, at least 35, at least 40, at least 45, at least 50, at least 55, at least 55, at least 60, at least 65, at least 70, at least 80, at least 85, at least 85, at least 90, or at least 95 of the structural components are nucleic acid molecule components.

A nucleic acid molecule component may comprise a polynucleotide sequence of at least 4, at least 5, at least 6, at least 7, at least 8, at least 9, at least 10, at least 15, at least 20, at least 25, at least 30, at least 35, at least 40, at least 45, at least 50, at least 60, at least 70, at least 75, at least 80, at least 85, at least 90, at least 100, at least 150, at least 200, at least 250, at least 300, at least 350, at least 400, at least 450, at least 500, at least 600, at least 700, at least 800, at least 900, at least 1000, at least 5000, or at least 10000 nucleotides. The polynucleotide sequence of the nucleic acid molecule components may vary. A hydrogel may comprise two or more nucleic acid molecule components that comprise the same polynucleotide sequence. Alternatively or in addition a hydrogel may comprise two or more nucleic acid molecule components that comprise different polynucleotide sequences (i.e., different in one or more nucleotides).

In some embodiments, at least one nucleic acid molecule component comprises the polynucleotide sequence of a protospacer adjacent motif (PAM). Examples of PAM sequences are known to those having skill in the art. In some embodiments, at least one nucleic acid molecule component lacks the polynucleotide sequence of a PAM.

A nucleic acid molecule component of a hydrogel may comprise a double-stranded nucleic acid region. In some embodiments, the double-stranded nucleic acid region is formed from two nucleic acid molecules. In other embodiments, the double-stranded nucleic acid region is formed from one nucleic acid molecule (e.g., a hairpin). Alternatively or in addition, a nucleic acid molecule component of a hydrogel may comprise a single-stranded nucleic acid region.

A nucleic acid molecule component of a hydrogel may comprise one or more monomer species selected from the group consisting of a ethylene glycol monomer (which when polymerized with another ethylene glycol monomer forms the polymer polyethylene glycol) and a acrylamide monomer (which when polymerized with another acrylamide monomer forms the polymer polyacrylamide). Mixtures of different monomers also can be polymerized to form copolymers, which also can be used in the hydrogels disclosed herein. Indeed, a nucleic acid molecule component may comprise any natural or synthetic polymeric matrix that can be functionalized with a nucleic acid. A nucleic acid molecule component of a hydrogel may comprise polyethylene glycol, polyacrylamide, gelatin, a fibrillar protein, or a combination thereof. As described in the Examples below, a nucleic acid molecule component may be manufactured by connecting a polynucleotide to a previously formed polymer (e.g., polyacrylamide or polyethylene glycol).

Alternatively or in addition, a hydrogel may comprise one or more structural component that comprises a nanostructured/microstructured conductive particle, such as metallic particles (gold, silver, etc.) or carbon particles. Example of nanostructured conductive particles are known to those having skill in the art. For example, in some embodiments, one or more structural component is selected from the group consisting of a carbon black nanoparticle, a carbon nanocone, a carbon nanofiber, a carbon nanoscroll, a carbon nanothread, a diamondoid, a nanodiamond, a single-walled carbon nanohorn, a carbon nanotube, graphene, graphene oxide, and fullerene.

In some embodiments, a hydrogel comprises a plurality of structural components, wherein: (i) three or more structural components of the plurality of structural components of the hydrogel are nucleic acid molecule components comprising at least 5 nucleotides and one or more species of monomers, wherein at least one monomer species is selected from the group consisting of an ethylene glycol monomer and an acrylamide monomer; and (ii) the three or more nucleic acid molecule components in (i) differ in sequence.

Methods of Altering a Property of a Hydrogel

In some aspects the disclosure relates to methods of altering a property of a hydrogel. A "property" of a hydrogel may be a physical property of the hydrogel. Physical properties include, but are not limited to, shape, volume, texture, color, odor, density, solubility, temperature, and charge. As described above, the hydrogels described herein have a polynucleotide-based structural component (i.e., a nucleic acid molecule component). A hydrogel property is "altered" according the methods described herein, when a chemical bond within a nucleic acid molecule component of the hydrogel is broken, for example, by enzymatic cleavage (e.g., CRISPR-mediated cleavage).

Accordingly, in some embodiments, the method of altering a property of a hydrogel comprises contacting the hydrogel with a CRISPR component comprising at least one clustered regularly interspaced short palindromic repeats (CRISPR) protein and at least one guide RNA, wherein the polynucleotide sequence of at least one nucleic acid molecule component in the hydrogel is cleaved when contacted with the CRISPR component, thereby altering a property of the hydrogel.

A guide RNA of a CRISPR component may be a CRISPR RNA (crRNA), a trans-acting crRNA (tracrRNA), or a single guide RNA (sgRNA). A CRISPR component may comprise multiple guide RNAs comprising the same polynucleotide sequence. Alternatively or in addition, a CRISPR component may comprise multiple guide RNAs comprising different polynucleotide sequences. For example, in some embodiments a CRISPR component comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 different guide RNAs.

A guide RNA of a CRISPR component may comprise a spacer region that complements (i.e., comprises a polynucleotide sequence that complements) one or more nucleic acid molecule component of the hydrogel. In some embodiments, a spacer region of a guide RNA is at least 60%, at least 65%, at least 70%, at least 75%, at least 80%, at least 85%, at least 90%, at least 95%, or at least 99% complementary to a polynucleotide sequence of one or more nucleic acid molecule component of the hydrogel. In some embodiments, a spacer region of a guide RNA comprises a polynucleotide sequence that is 100% complementary to a nucleic acid molecule component of the hydrogel.

Alternatively, a guide RNA of a CRISPR component may comprise a spacer region that complements (i.e., comprises a polynucleotide sequence that complements) a trigger molecule. As used herein, the term "trigger molecule" refers to a nucleic acid molecule that is not a structural component of a hydrogel and that, when cleaved my a CRISPR protein, increases the enzymatic activity of the CRISPR protein (e.g., single- and/or double-stranded endonuclease activity). A trigger molecule may increase one or more enzymatic activity of a CRISPR protein (e.g., single- and/or double-stranded endonuclease activity) by at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, at least 500%, at least 600%, at least 700%, at least 800%, at least 900%, at least 10000%, or at least 50000%. Methods of measuring the enzymatic activity of CRISPR proteins are known to those having skill in the art and are disclosed herein in Example 2.

In some embodiments, a spacer region of a guide RNA comprises a polynucleotide sequence that is at least 60%, at least 65%, at least 70%, at least 75%, at least 80%, at least 85%, at least 90%, at least 95%, or at least 99% complementary to a polynucleotide sequence of a trigger molecule. In some embodiments, a spacer region of a guide RNA comprise a polynucleotide sequence that is 100% complementary to a polynucleotide sequence of a trigger molecule.

In some embodiments, the method further comprises contacting a CRISPR component with a trigger molecule. A trigger molecule may comprise a single-stranded region. A trigger molecule may comprise a double-stranded region. The length of a trigger molecule may vary. For example, a trigger molecule may be at least 20, at least 25, at least 30, at least 35, at least 40, at least 45, at least 50, at least 60, at least 70, at least 75, at least 80, at least 85, at least 90, at least 100, at least 150, at least 200, at least 250, at least 300, at least 350, at least 400, at least 450, or at least 500 nucleotides in length.

Clustered regularly interspaced short palindromic repeats (CRISPR) proteins are a family of RNA-guided endonucleases. Various CRISPR proteins have been identified and characterized previously. Any CRISPR protein that can cut DNA/RNA may be utilized herein. A CRISPR protein may comprise RNA-guided dsDNA endonuclease activity. Alternatively or in addition, a CRISPR protein may comprise ssDNA endonuclease activity.

A CRISPR protein of a CRISPR component may comprise the amino acid sequence of Cas9, Cas12a, C2c1, C2c2, C2c3, or functional variants thereof. Examples of these CRISPR proteins (e.g., Cas9, Cas12a, C2c1, C2c2, C2c3) have been identified in various species.

The term "functional variant" includes polypeptides which are about 70% identical, at least about 80% identical, at least about 90% identical, at least about 95% identical, at least about 98% identical, at least about 99% identical, at least about 99.5% identical, or at least about 99.9% identical to a protein's native amino acid sequence (i.e., wild-type amino acid sequence) and which retain functionality.

The term "functional variant" also includes polypeptides which are shorter or longer than a protein's native amino acid sequence by about 5 amino acids, by about 10 amino acids, by about 15 amino acids, by about 20 amino acids, by about 30 amino acids, by about 40 amino acids, by about 50 amino acids, by about 75 amino acids, by about 100 amino acids or more and which retain functionality.

In the context of a CRISPR protein, the term "retain functionality" refers to a functional variant's ability to cleave a nucleic acid molecule at least about 5%, 10%, 20%, 25%, 30%, 40%, 50%, 60%, 70%, 75%, 80%, 90%, 100%, or more than 100% as efficiently as the respective non-variant (i.e., wild-type) protein. Methods of measuring the enzymatic activity of CRISPR proteins are known to those having skill in the art and are disclosed herein in Example 2.

Methods of Releasing a Property of Interest from a Hydrogel

In some aspects the disclosure relates to methods of releasing a product of interest from a hydrogel. In some embodiments, the method comprises altering a property of the hydrogel according to the methods described herein (e.g., "Methods of Altering a Property of a Hydrogel"), thereby releasing the product of interest from the hydrogel.

In some embodiments, the product of interest is a molecule that is anchored to the hydrogel. In some embodiments, the product of interest is encapsulated by the hydrogel.

In some embodiments, the product of interest is selected from the group consisting of a molecule, a nanoparticle, and a live cell.

Methods of Modulating the Flow of a Product of Interest Through a Hydrogel

In some aspects the disclosure relates to methods of modulating the flow of a product of interest through a hydrogel. In some embodiments, the method comprises altering a property of the hydrogel according to the methods described herein (e.g., "Methods of Altering a Property of a Hydrogel"), thereby modulating the flow of the product of interest through the hydrogel.

In some embodiments, the product of interest is an electric signal. In some embodiments, the electric signal is selected from the group consisting of voltage, impedance, capacitance, resistance and current.

In some embodiments, the product of interest is a solution. In some embodiments, the solution conducts an electric current.

In some embodiments, the method further comprises detecting the electric current/signal.

Compositions Comprising a Hydrogel and a CRISPR Component

In some aspects the disclosure relates to compositions comprising a hydrogel and a CRISPR component.

In some embodiments, the composition comprises: (i) a hydrogel as described herein; and (ii) a CRISPR component comprising a guide RNA that complements a structural component of the hydrogel, wherein the composition lacks a CRISPR protein corresponding to the guide RNA. A CRISPR protein corresponds to a guide RNA, when it is capable of binding the guide RNA and mediating RNA-guided endonuclease activity. The composition may further comprise a triggering nucleic acid molecule.

In some embodiments, the composition comprises: (i) a hydrogel as described herein; and (ii) a CRISPR component comprising a CRISPR protein, wherein the composition lacks a guide RNA that complements a structural component of the hydrogel (i.e., the degree of complementation is insufficient to facilitate RNA-guided endonuclease activity of the CRISPR protein).

In some embodiments, the composition comprises: (i) a hydrogel as described herein; and (ii) a CRISPR component comprising a trigger molecule, wherein the composition lacks a guide RNA that complements the trigger molecule (i.e., the degree of complementation is insufficient to facilitate RNA-guided endonuclease activity of a CRISPR protein). In some embodiments, the composition further comprises a CRISPR protein.

In some embodiments, the composition comprises: (i) a hydrogel as described herein; and (ii) a CRISPR component comprising a guide RNA that complements a structural component of the hydrogel and a CRISPR protein, wherein the composition lacks a trigger molecule.

A guide RNA of a CRISPR component may be a CRISPR RNA (crRNA), a trans-acting crRNA (tracrRNA), or a single guide RNA (sgRNA). A CRISPR component may comprise multiple guide RNAs comprising the same polynucleotide sequence. Alternatively or in addition, a CRISPR component may comprise multiple guide RNAs comprising different polynucleotide sequences. For example, in some embodiments a CRISPR component comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 different guide RNAs.

A guide RNA of a CRISPR component may comprise a spacer region that complements (i.e., comprises a polynucleotide sequence that complements) one or more nucleic acid molecule component of the hydrogel. In some embodiments, a spacer region of a guide RNA is at least 60%, at least 65%, at least 70%, at least 75%, at least 80%, at least 85%, at least 90%, at least 95%, or at least 99% complementary to a polynucleotide sequence of one or more nucleic acid molecule component of the hydrogel. In some embodiments, a spacer region of a guide RNA comprises a polynucleotide sequence that is 100% complementary to the nucleic acid molecule component of the hydrogel.

In some embodiments, a spacer region of a guide RNA is at least 60%, at least 65%, at least 70%, at least 75%, at least 80%, at least 85%, at least 90%, at least 95%, or at least 99% complementary to a polynucleotide sequence of a trigger molecule. In some embodiments, a spacer region of a guide RNA comprises a polynucleotide sequence that is 100% complementary to a polynucleotide sequence of a trigger molecule.

A CRISPR component may comprise multiple trigger molecules comprising the same polynucleotide sequence. Alternatively or in addition, a CRISPR component may comprise multiple trigger molecules comprising different polynucleotide sequences. For example, in some embodiments a CRISPR component comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 different trigger molecules.

A trigger molecule may comprise a single stranded region. A trigger molecule may comprise a double stranded region. The length of a trigger molecule may vary. For example, a trigger molecule may be at least 20, at least 25, at least 30, at least 35, at least 40, at least 45, at least 50, at least 60, at least 70, at least 75, at least 80, at least 85, at least 90, at least 100, at least 150, at least 200, at least 250, at least 300, at least 350, at least 400, at least 450, or at least 500 nucleotides in length.

A CRISPR protein of a CRISPR component may comprise the amino acid sequence of Cas9, Cas12a, C2c1, C2c3, C2c2, or functional variants thereof. Examples of these CRISPR proteins (i.e., Cas9, Cas12a, C2c1, C2c3, C2c2) have been identified in various species.

The term "functional variant" includes polypeptides which are about 70% identical, at least about 80% identical, at least about 90% identical, at least about 95% identical, at least about 98% identical, at least about 99% identical, at least about 99.5% identical, or at least about 99.9% identical to a protein's native amino acid sequence (i.e., wild-type amino acid sequence) and which retain functionality.

The term "functional variant" also includes polypeptides which are shorter or longer than a protein's native amino acid sequence by about 5 amino acids, by about 10 amino acids, by about 15 amino acids, by about 20 amino acids, by about 30 amino acids, by about 40 amino acids, by about 50 amino acids, by about 75 amino acids, by about 100 amino acids or more and which retain functionality.

In the context of a CRISPR protein, the term "retain functionality" refers to a functional variant's ability to cleave a nucleic acid molecule at least about 5%, 10%, 20%, 25%, 30%, 40%, 50%, 60%, 70%, 75%, 80%, 90%, 100%, or more than 100% as efficiently as the respective non-variant (i.e., wild-type) protein. Methods of measuring the enzymatic activity of CRISPR proteins are known to those having skill in the art and are disclosed herein in Example 2.

CRISPR-Responsive Switches

In some aspects the disclosure relates to CRISPR-responsive switches. A CRISPR-responsive switch may comprise a composition as described above in "Compositions Comprising a Hydrogel and a CRISPR Component."

In some embodiments, a CRISPR-responsive switch comprises: (i) a first compartment, wherein the first compartment comprises a composition comprising: (a) a hydrogel as described herein; and (b) a CRISPR component comprising a guide RNA, wherein the composition lacks a CRISPR protein corresponding to the guide RNA; and (ii) a second compartment, wherein the second compartment comprises a CRISPR protein corresponding to the guide RNA of (i)(b).

In some embodiments, a CRISPR-responsive switch comprises: (i) a first compartment, wherein the first compartment comprises a composition comprising: (a) a hydrogel as described herein; and (b) a CRISPR protein, wherein the composition lacks a guide RNA that complements a structural component of the hydrogel of (i)(a); and (ii) a second compartment, wherein the second compartment comprises a guide RNA that complements a structural component of the hydrogel of (i)(a).

In some embodiments, a CRISPR-responsive switch comprises: (i) a first compartment, wherein the first compartment comprises a composition comprising: (a) a hydrogel as described herein; and (b) a CRISPR component comprising a trigger molecule, wherein the composition lacks a guide RNA that complements the trigger molecule; (ii) a second compartment, wherein the second compartment comprises a guide RNA that complements the trigger molecule of (i)(b).

In some embodiments, a CRISPR-responsive switch comprises: (i) a first compartment, wherein the first compartment comprises a composition comprising: (a) a hydrogel as described herein; and (b) a CRISPR component comprising a guide RNA and a CRISPR protein, wherein the composition lacks a trigger molecule; (ii) a second compartment, wherein the second compartment comprises the trigger molecule of (i)(b).

In some embodiments, in the OFF state, the components of the first compartment are not in contact with the components of the second compartment; and wherein, in the ON state, the components of the first compartment are in contact with the components of the second compartment.

In some embodiments, turning the switch from OFF to ON releases a product of interest from the hydrogel. In some embodiments, turning the switch from OFF to ON alters the flow of a product of interest through the hydrogel.

In some embodiments, the product of interest is selected from the group consisting of a molecule, a nanoparticle, and a live cell. In some embodiments, the product of interest is selected from the group consisting of an electric signal and a solution.

In some aspects, the disclosure relates to devices comprising a CRISPR-responsive switch as described above.

EXAMPLES

Example 1. Programmable CRISPR-Responsive Smart Materials

Stimuli-responsive hydrogels activated by biological signals play an increasingly important role in biotechnology applications. Here, the programmability and specificity of CRISPR-associated nucleases is exploited to fabricate programmable DNA-based smart hydrogels (CRISPR-gels) that modulate their multiscale properties in response to specific DNA inputs. Four applications of CRISPR-gels are reported: (i) branched polyethylene glycol-based hydrogels for release of DNA-anchored compounds; (ii) polyacrylamide-DNA degradable hydrogels that release encapsulated molecules, nanoparticles, and live cells; (iii) conductive carbon black-DNA hydrogels that act as degradable electrical fuses; and (iv) a tunable polyacrylamide-DNA hydrogel crosslinking system operating as a fluidic valve with electrical readout for RFID remote signaling. These new functionalities of DNA-responsive smart materials will allow for a diverse range of novel applications in cell therapy, tissue engineering, drug delivery, bio-electronics, and nucleic acid diagnostics.

Example 2. Characterization of Cas12a Enzymatic Activity

Cas12a, a deoxyribonuclease (DNase) that can be programmed with CRISPR guide RNAs (crRNAs), was selected for its ability to sense specific DNA sequences and subsequently generate broad catalytic responses. A Cas12a ortholog from Lachnospiraceae bacterium ND2006 (LbaCas12a) (1, 2) that displays two activities: specific cleavage of dsDNA fragments matching the crRNA sequence (cis-cleavage) and subsequent indiscriminate ssDNA cleavage (trans-cleavage) was exploited. Once the Cas12a-crRNA complex binds and cleaves its dsDNA target, trans-cleavage of nearby ssDNA is multiple-turnover at a rate of ~1250 s−1 with a high catalytic efficiency (kcat/Km) ~1.7×109 s−1M−1 (2). crRNAs were developed to detect specific fragments of the mecA antibiotic-resistance gene of methicillin-resistant *Staphylococcus aureus* (MRSA), as a clinically relevant model to demonstrate the target programmability of CRISPRgels.

Figure 5:
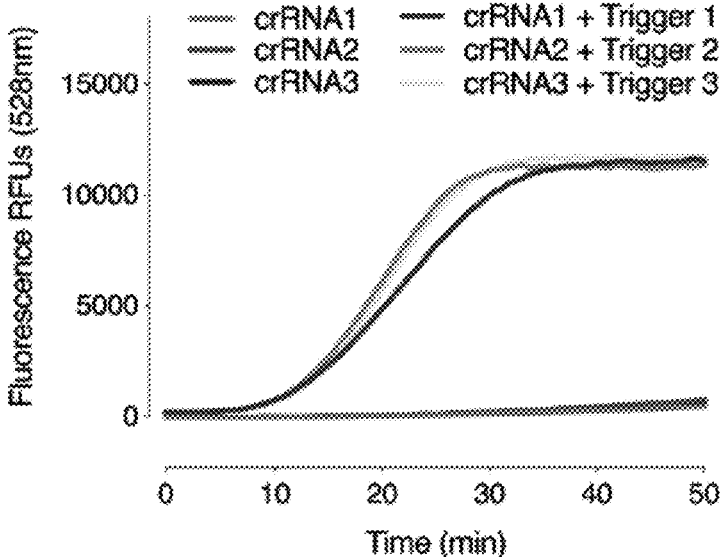
FIG. 5. Programmability of the Cas12a-based MecA detection system. Three crRNAs were generated against different MRSA targets; the ability of crRNA-defined dsDNA triggers to activate Cas12a trans-cleavage activity was tested using a ssDNA fluorophore-quencher probe. The reactions contained 30 nM Cas12a, 90 nM crRNA, 2.5 nM dsDNA specific trigger and 750 nM quenched fluorescently labeled ssDNA reporter. Fluorescence signal increased in a similar manner for all three crRNA/dsDNA target pairs tested as the ssDNA probe was cleaved. The background activities without dsDNA triggers were also similar for the three different crRNAs.

The trans-cleavage activity of Cas12a-crRNA in solution was validated by incubating the LbaCas12a with crRNA, a MRSA-specific dsDNA trigger, and a quenched fluorescently labeled ssDNA as the reporter. All tested MRSA crRNA and dsDNA trigger pairs showed comparable performances (FIG. 5). MRSA1 crRNA had a detection limit of ~16 pM (FIG. 6A) and was selected for subsequent experiments to standardize results. Sequence mismatches between the crRNA and trigger reduced the trans-cleavage rate (FIGS. 6B-6C), consistent with patterns observed in previous studies (2, 13). Nonspecific dsDNA triggers did not 5 result in significant enzymatic activation (FIG. 6D), confirming the crRNA-defined target specificity of Cas12a. Cas12a's high dsDNA target specificity and rapid nonspecific ssDNA trans-cleavage activity make it an ideal candidate for modulating a wide range of physical and mechanical hydrogel properties (FIG. 1).

Example 3. Polyethylene Glycol-Based DNA Hydrogels and Uses Thereof

Figure 2A:
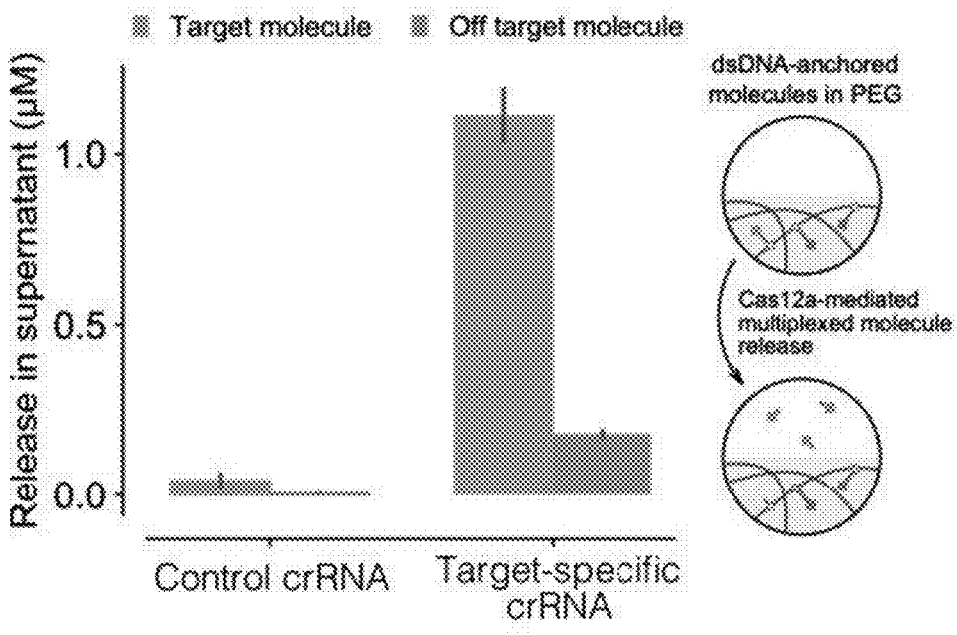
FIGS. 2A-2E. Programmable Cas12a-mediated release of small-molecules, nanoparticles, and live cells from DNA hydrogels.
Figure 2B:
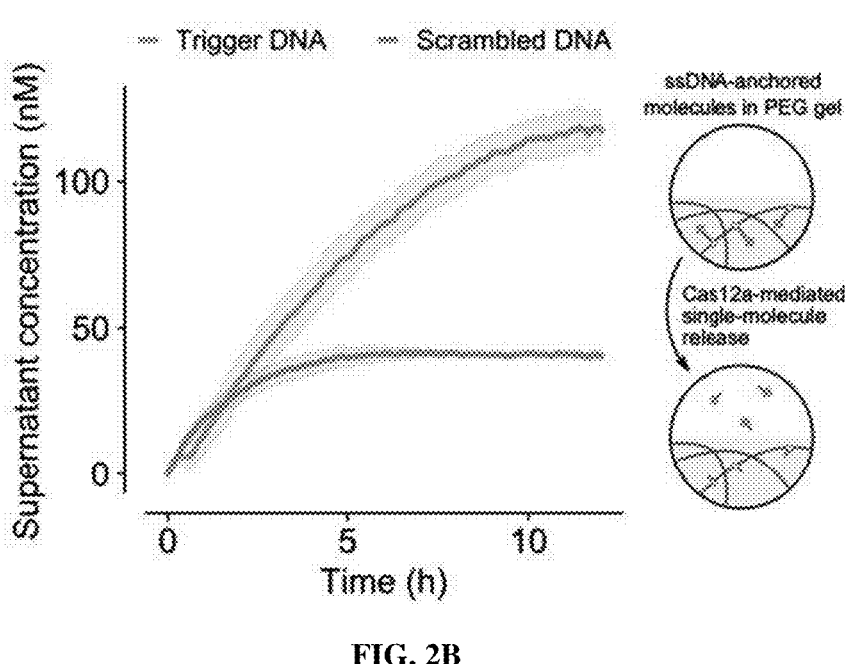

Programmable, biocompatible materials capable of the controlled release of soluble compounds, as well as encapsulated cells, have broad utility in various therapeutic and research applications (14-17). To model specific, orthogonal small molecule release from CRISPR-gels, poly(ethylene glycol) (PEG)-based DNA hydrogels were fabricated with dsDNA anchors (FIG. 1, Panel A). Two distinct fluorophores were tethered to PEG chains through different dsDNA linkers, one of them harboring the target mecA sequence (FIG. 2A). In this cis-cutting experiment, 6-carboxyfluorescein (6-FAM) was used as the target release molecule, while 6-carboxyhexachlorofluorescein (6-HEX) was used as the off-target control. Cas12a recognized and cleaved the specific dsDNA activators within the PEG hydrogel, resulting in the preferential release of the associated 6-FAM into solution (FIG. 2A). The orthogonal release of user-defined molecules from the hydrogel suggests a potential for high-level multiplexing, albeit limited by the turnover of Cas12a cis-cleavage activity. In order to increase the release rate of small molecules from PEG-based gels, the potential to exploit Cas12a's multi-turnover ssDNA trans-cleavage activity upon activation with dsDNA triggers was tested. A single fluorophore was conjugated to the PEG polymer via a partially hybridized ssDNA linker (FIG. 1A). The activation of crRNA-Cas12a led to a significantly increased release of the fluorescent molecule compared to gels incubated with crRNA-Cas12a enzymes exposed to a scrambled trigger (FIG. 2B), consistent with the efficient ssDNAse activity of dsDNA-activated Cas12a.

Example 4. Polyacrylamide-Based DNA Hydrogels and Uses Thereof

Figure 2C:
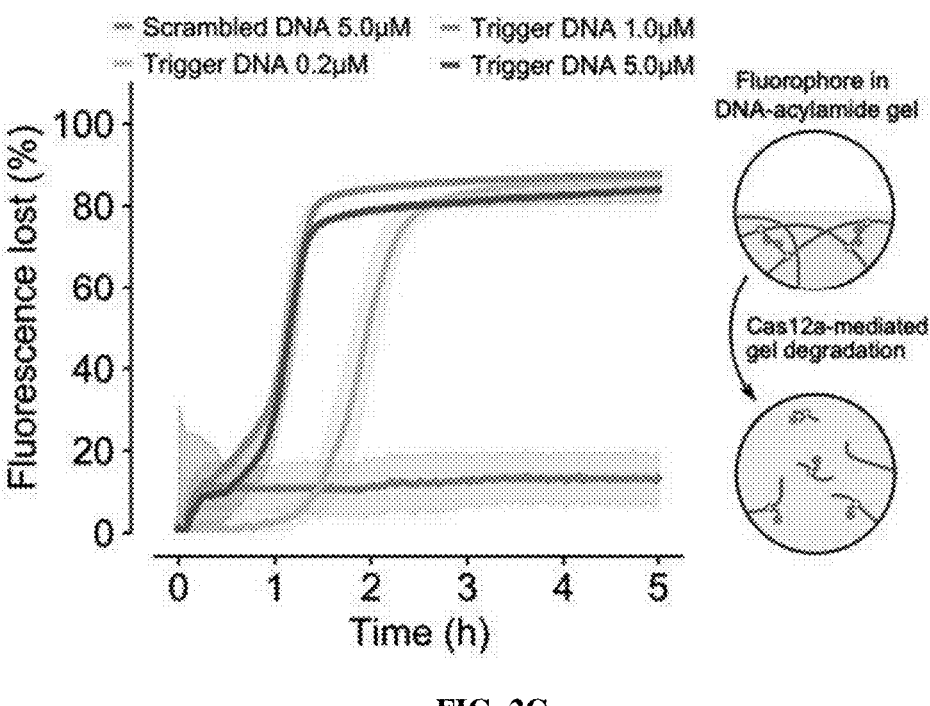

Recognizing the potential to utilize Cas12a trans-cleavage to modulate properties of DNA-based materials at a larger scale, polyacrylamide-DNA hydrogels were designed next (9). Two non-complementary methacryl-modified oligonucleotides were separately conjugated into polyacrylamide (PA) chains (Ps-X and Ps-Y) (FIG. 7). The PA-DNA chains were cross-linked with partially single-stranded DNA bridges harboring TTATT trans-cleavage sites (FIG. 1B). In this PA-based CRISPR-gel, Cas12a ssDNA cleavage physically disrupts the polymer networks by degrading the DNA crosslinks (FIG. 2C). The Cas12a-induced degradation of PA-based CRISPR-gels was initially evaluated with a DNA-intercalating dye to label bridge sequences in PA-DNA gels and track gel integrity. Bridge sequences were degraded upon exposure to crRNA-Cas12a and trigger dsDNA, as revealed by the dissipation of gel fluorescence in a manner dependent on trigger concentration (FIG. 2C). This effect was also clearly observed by visual inspection (FIG. 8). Cleavage rates decreased when dsDNA sequences contained nucleotide mismatches (FIG. 9), demonstrating crRNA-Cas12a's sequence-specificity.

Figure 2D:
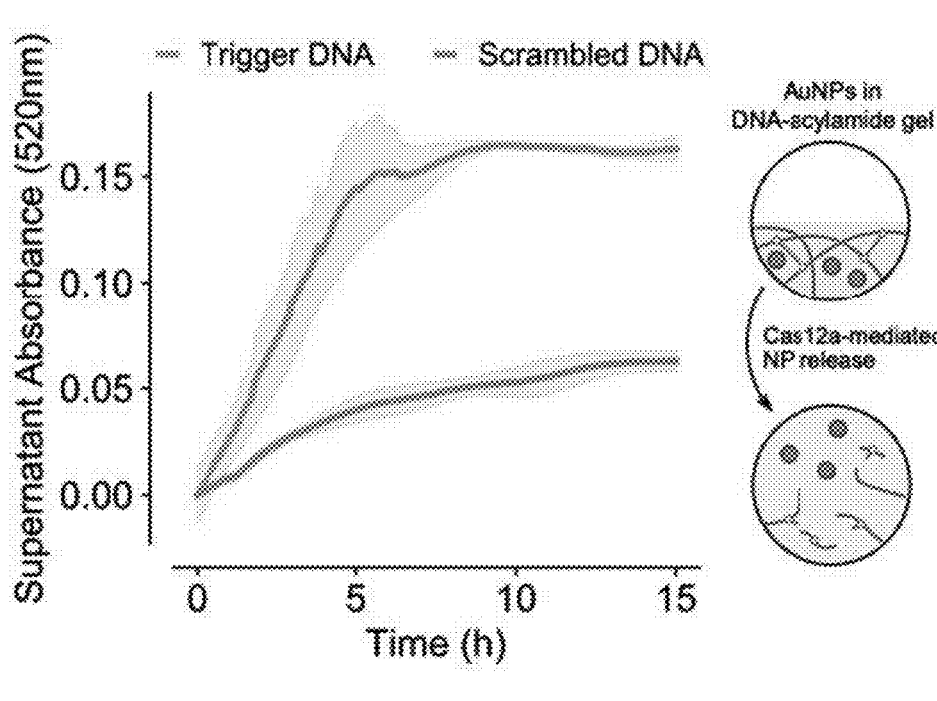
Figure 2E:
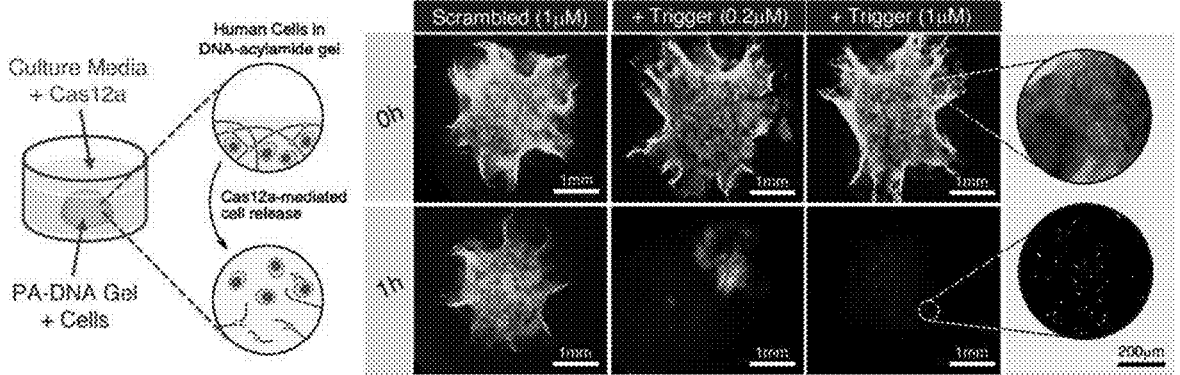

The triggered release of nanoparticles (NPs) was tested by encapsulating 18-nm PEG-coated gold NPs (FIG. 10) in PA-DNA hydrogels. Exposure to dsDNA trigger led to significant nanoparticle release via crRNA-Cas12a complex activation and gel cleavage, whereas gels incubated with a scrambled dsDNA trigger showed minimal NP release (FIG. 2D). The triggered release of a living cargo was then performed by encapsulating a suspension of human K562 cells into PA-DNA hydrogels and exposing the gels to activated crRNA-Cas12a. Complete gel degradation and cell release were observed within 1 hour in the presence of 1 μM dsDNA trigger (FIGS. 2E and 11), without significantly compromising cell viability (FIG. 12). In contrast, gels exposed to a scrambled dsDNA trigger control remained intact. These results demonstrate that payloads ranging from small molecules to live cells can be immobilized in biocompatible hydrogels and released upon addition of programmable target dsDNA sequences without the need for hydrogel redesign. This opens up future possibilities for the in-situ modulation of the cellular microenvironment, such as the intervention-free release of bioactive compounds and matrix remodeling in response to sequence-specific, cell-free DNA inputs.

Example 5. Carbon Black-Based DNA Hydrogels and Uses Thereof

For the third CRISPR-gel design, the degradation of a conductive DNA-based hydrogel was sought to be modulated to act as an electrical fuse capable of changing conductivity upon exposure to a specific DNA trigger (FIG. 1C). Such a conductive CRISPR-gel system may be desirable for a variety of sensing and diagnostic applications where the direct interface to electrical devices (e.g., analog circuits and microcontrollers) is required. These conductive, self-assembled materials consisted of ssDNA networks cross-linked with carbon black (CB) conductive nanoparticles (CB-DNA gels). CB is composed of 10-100 nm spherical particles (18), which contain graphitic-like domains arranged concentrically (19). CB is widely used in industrial applications to impart electrical conductivity to insulating polymers (20) and is used here as a conductive cross-linker in the hydrogels. CB-DNA gels were synthesized through thermal melting of dsDNA followed by fast cooling in the presence of CB nanoparticles. This leads to the strong, non-covalent association of the aromatic DNA nucleotides with nearby CB graphitic surfaces (21) through hydrogen bonding and π-π stacking interactions (22-24). In this hydrogel, DNA behaves as the main structural component capable of linking carbon black particles together to form a robust, three-dimensional network (22, 25). The conductive paths within the network can be eroded via Cas12a-crRNA catalytic activity.

Figure 3A:
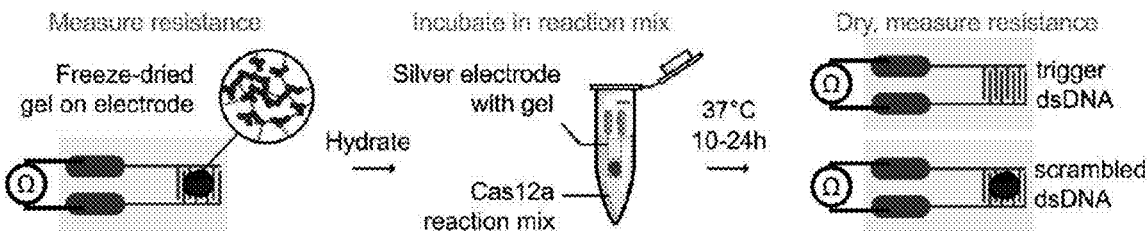
FIGS. 3A-3C. Carbon black-DNA (CB-DNA) hydrogels can be used as Cas12a-actuated electrical fuses.

To test this system, CB-DNA droplets were spotted onto silver printed 50 μm-gap interdigitated electrodes (IDEs) and lyophilized (FIG. 3A). CB-DNA gels were then incubated in a solution containing Cas12a, crRNA and dsDNA trigger. The integrity of CB-DNA hydrogels during Cas12a-mediated degradation was monitored visually (FIG. 3B) and tested electrically (FIG. 3C) with increasing concentrations of dsDNA inputs. It was found that crRNA-Cas12a with 50 nM dsDNA trigger was able to completely detach 50% of the hydrogels from electrodes in 10 h, and 83% of hydrogels after 20 h. Incubation in higher dsDNA trigger concentrations (1 μM and 500 nM) led to CB-DNA detachment in the majority of electrodes within 10 h.

Figure 3B:
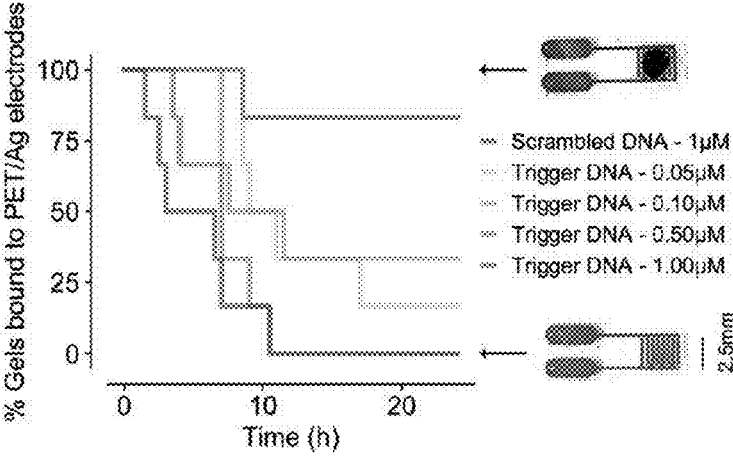
Figure 3C:
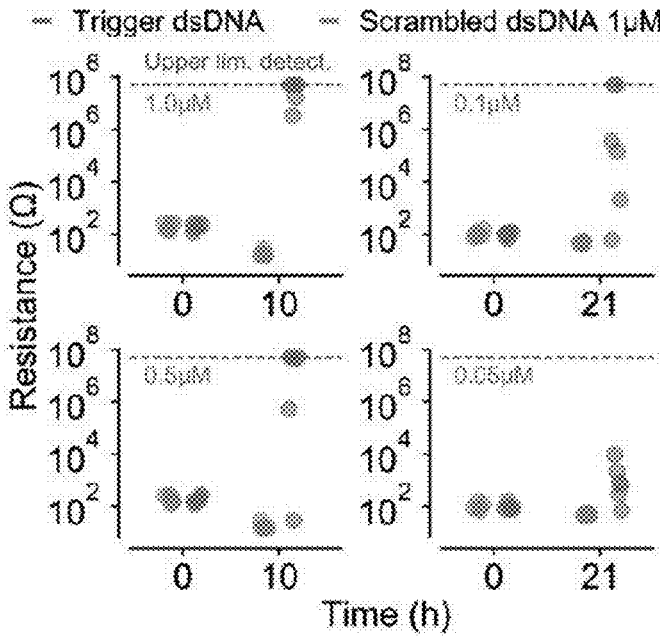

Before Cas12a-mediated degradation, lyophilized CB-DNA hydrogels showed high conductivity (~4 mS/cm), comparable to that reported for graphene-DNA gels of similar compositions (22). After initial electrical testing, IDEs spotted with CB-DNA hydrogels were incubated in Cas12acrRNA solutions containing dsDNA triggers or scrambled dsDNA. Samples incubated in increasing concentrations of specific dsDNA triggers showed higher degradation and higher resistivity than controls incubated with nonspecific scrambled dsDNA (FIG. 3C). In this system, binding between crRNA-Cas12a and the target dsDNA activator catalyzes a programmable CBDNA hydrogel erosion. In turn, the bulk polymer loss and material detachment led to a fuse-like loss in conductivity along the IDE terminals after drying (FIG. 3B and FIG. 3C). This easily implementable CB-DNA gel formulation provides a direct link between dsDNA triggers and electrical outputs, increasing the applicability of DNA-hydrogels for a variety of sensing and diagnostic uses.

Example 6. DNA Hydrogel Switches and Uses Thereof

To demonstrate the use of CRISPR-gels in biological sensors, a tunable PA-DNA hydrogel was used to control the permeability and electrical readout of a paper-based microfluidic device (FIG. 4). Paper-based technologies have shown promise for point-of-care diagnostics as they are low cost, equipment-free, and easy to use (26, 27). The CRISPR-gel device (FIG. 4A, FIG. 13) expands on the concept of multilayered paper microfluidic chips (μPAD) that rely on the capacity of hydrogels to form within porous networks and obstruct flow through them (28).

The paper layers of the device were folded in an accordion arrangement to create a three-dimensional, multilayered structure where the hydrophilic regions are topologically aligned. Capillary-driven fluid movement through the device terminated in a fifth and final layer where the output was measured (FIGS. 4A and 10). One of the upper layers contained PA-DNA gel precursors (Ps-X and Ps-Y) that, when mixed with ssDNA cross-linker, formed a hydrogel in the paper microchannels (29, 30 and FIG. 4A Inset). The extent of gel formation, and therefore the rate of buffer flow, was dependent on the extent of degradation of the ssDNA gel cross-linker during a pre-incubation step. By degrading the cross-linker using activated Cas12a, the level of buffer flow was able to be coupled to the concentration of dsDNA trigger added to the 4-hour Cas12a reaction.

In the presence of a specific dsDNA trigger, colored dye in the channel confirmed that the hydrogel did not form; that is, the ssDNA cross-linker had been degraded by Cas12a during the pre-incubation step. In contrast, when nonspecific dsDNA trigger was present during preincubation, ssDNA cross-linkers were not cleaved, allowing for hydrogel assembly in the microchannel (FIG. 4A, top and bottom). Using a standard visual output, it was found that the rate of buffer flow through the μPAD is inversely related to the concentration of the dsDNA trigger (FIG. 14).

Visual readouts of buffer flow are commonly used, yet they are difficult to couple to downstream hardware for data processing and transmission. To overcome this limitation, the CRISPR-actuated fluidic system was modified to read buffer flow directly as an electric signal (FIG. 4B and FIG. 4C). To perform these measurements, the microfluidic channel in the final layer was sandwiched between two electrodes and connected to an ohmmeter (FIG. 4A, FIG. 13). Electrical conductivity between the electrodes required the presence of electrolytes provided by the flowing buffer.

The electrical conductivity was directly correlated to the buffer penetration length in the μPAD channel: as expected, the evolution of signal across time in the presence of dsDNA activated Cas12a could be described by a Washburn equation (FIG. 4B, r2>0.98 for both samples) (31). End-point electrical conductivity increased with increasing dsDNA trigger concentrations. Using this approach, sub-nanomolar concentrations of dsDNA trigger were successfully detected at a 5-45 minute timepoint, demonstrating the potential of the CRISPR μPAD for embedded sensor applications (FIG. 4C). Nonspecific dsDNA trigger did not activate Cas12a and failed to prevent gel formation, thus leaving the electrical circuit open (FIG. 4B and FIG. 4C). It was possible to reduce the pre-incubation time required to observe a signal to 1 hour by tuning the properties of the precursors Ps-X and Ps-Y (FIG. 15).

Figure 4D:
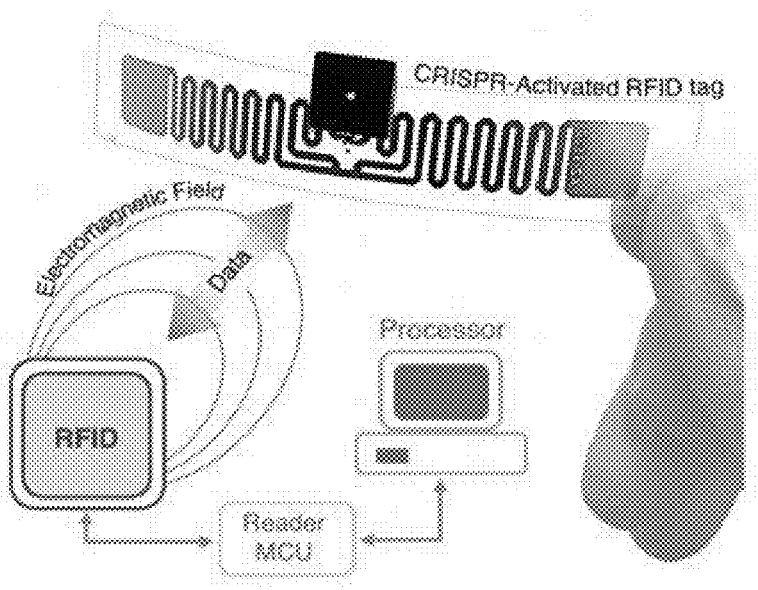
Figure 4E:
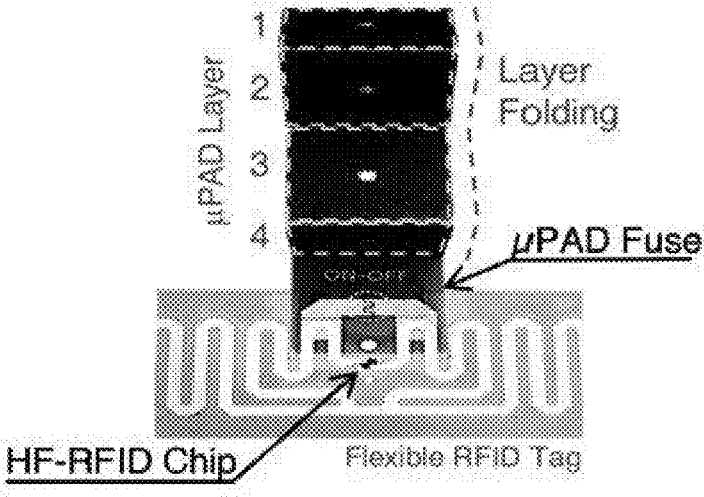
Figure 4F:
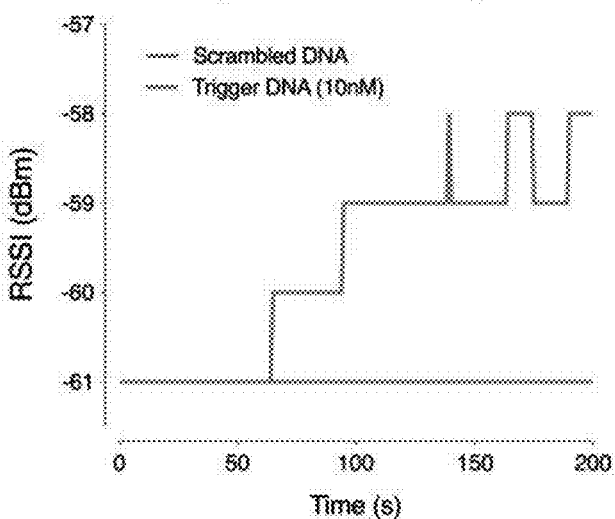

To demonstrate the feasibility of interfacing CRISPR-Cas reactions with larger electronic systems through hydrogel actuation, a wireless radio-frequency identification (RFID) module was incorporated into the CRISPR-gel μPAD (FIG. 4D). The previous μPAD assembly was modified to replace the final layer with a short-circuiting, interdigitated electrode in a flexible RFID tag (FIG. 4E). This allowed for the remote reading of digital signals from the RFID. For samples pre-incubated with dsDNA trigger and Cas12a, buffer flow through the μPAD caused RFID antenna short-circuiting that could be detected in real-time using the signal strength of the RFID tag (FIG. 4F). Similar signals were not detected for samples pre-incubated with a scrambled dsDNA control.

Example 7. Discussion

Taken together, several strategies to interface biological signals with materials that combine the inherent programmability of CRISPR-associated enzymes with simple hydrogel designs were demonstrated. These strategies offer control over a variety of complex behaviors and properties, including the release of small molecules, nanoparticles, and live cells, as well as bulk hydrogel degradation, electronic signal transduction, and microfluidic valve actuation. By exploiting the enzymatic properties of Cas12a, novel formulations that substantively improve on existing hydrogel capabilities were designed. This includes increasing programmability, as well as providing new forms of output for these platforms. These new capabilities of CRISPR-responsive materials are expected to enhance existing biomaterial-based approaches for cell therapy (32, 33), drug delivery (14), regenerative medicine (5), molecular diagnostics, and novel bio-electronic interfaces with programmable readouts.

Example 8. Materials and Methods for Examples 1-7

In Vitro Cas12a Reagent Validation with ssDNA

Trans-degradation of non-target ssDNA upon Cas12a activation was measured in solution by mixing trigger dsDNA with Cas12a-crRNA complex and using a quenched, fluorescently labeled reporter. Cas12a-crRNA complex was assembled by incubating 200 nM Cas12a with 250 nM crRNA in 1×NEB 2.1 buffer at 37° C. for 10 min. The reaction initiated upon mixing the Cas12a complexes with dsDNA triggers and ssDNA-quenched, fluorescently labeled reporter (FQ reporter) to a final concentration of 50 nM Cas12a: 62.5 nM crRNA: 750 nM FQ reporter and dsDNA triggers in NEB 2.1 buffer. Reactions (3 μl, 384-well microplate) were incubated in a fluorescence plate reader (Biotek NEO HTS) for 120 minutes at 37° C. Fluorescence readings were recorded every 2 min (Ex: 485 nm; Em: 535 nm).

Synthesis of Gelatin-PEG Gels and Controlled Release Experiments

N-hydroxysuccinimide (NHS)-activated 8-arm PEG (40 kDa, NOF Corporation) were dissolved at 5% w/v in PBS. The solution was mixed with DNA duplexes with 5' overhangs (one amine-terminated strand, the other FAM-terminated, IDT) to yield a solution of 4% PEG, 12 μM DNA, which was incubated for 30 min at room temperature to allow the reaction of amines with NHS. Then, equal volumes of this solution were mixed with a warm gelatin (bovine, type B alkali-treated, Sigma) solution at 1% w/v in PBS; 50 μL volumes of this gel precursor were transferred on the side of clear-bottom tissue-culture wells and the cross-linking reaction was allowed to occur on ice for 1 h, then at room temperature for 1 h. The gels were finally incubated in Tris reaction buffer (1×NEB 2.1) for 1 h at room temperature to block unreacted NHS moieties and remove most unbound DNA molecules. Digestion by Cas12a was performed overnight at 37° C. in 500 μL 1×NEB 2.1 buffer, with 50 nM Cas12a, 200 nM crRNA, and 400 nM of the trigger or scrambled dsDNA. Fluorescence was measured in a plate reader as described for the DNA-polyacrylamide gels (Ex: 485 nm; Em: 525 nm); data were smoothened with a first-order Savitzky-Golay filter.

Sequence-Specific Release of dsDNA-Anchored Molecules Using Cis-Cleavage Activity Both N-hydroxysuccinimide (NHS)-activated 8-arm PEG (40 kDa, NOF Corporation) and amine-activated 8-arm PEG (20 kDa, JenKem) were dissolved at 8% w/v in water. Each pair of oligonucleotides was pre-hybridized functionalized with 5'-amine groups or 5'-fluorophores, to a final concentration of 50 μM dsDNA for each duplex. To form functionalized hydrogels, the dsDNA probes were first incubated with NHS-PEG: 1 volume of each 50 μM dsDNA solution was added to 4 volumes of 125 mM triethanolamine buffer (pH 7); this solution was then mixed with 3 volumes of PEG-NHS stock. The solution was incubated for 15 min at room temperature to graft DNA molecules on the PEG through NHS-amine reactions. Finally, hydrogel polymerization was started by adding one volume of PEH-Amine stock; 10 μL volumes of gel precursor were immediately pipetted into 0.2 mL microtubes and the reaction was allowed to complete in the dark at room temperature overnight. To remove TAE buffer and unbound DNA, the gels were pre-incubated at 37° C. in excess of 1×NEB 2.1 buffer for 24 h, replacing the buffer after 8 and 20 h. At the end of the incubation, the equilibrated supernatant was stored and the volume of gels (after swelling) were estimated based on their weight and the density of water; the gels were covered with an equivalent volume of equilibrated buffer supplemented with 2 μM Cas12a enzyme and a 4× excess of crRNA specific to one of the two dsDNA anchors. The reaction was incubated overnight at 37° C., after which the amount of each fluorophore released in the supernatant was estimated by measuring the fluorescence in aliquots (wavelengths were chosen to minimize spectral overlaps: for FAM, Ex: 485 nm/Em: 520 nm; and for HEX, Ex: 530 nm/Em: 560 nm) and comparing to dilution standards.

Synthesis of Carbon Black-DNA Gels

Aqueous suspensions of carbon black according to a modified version of the protocol by Parant et al. were prepared (34). A stock of 1.5 wt % Arabic gum (Sigma, CAS: 9000-01-5) was prepared by dissolving for 2 h in water at 80° C. 8 wt % acetylene black particles (>99.9%, Alfa Aesar™, AA3972430) were then added and resuspended by ultrasonication for 15 minutes (Fisher Scientific FB505 Sonic Dismembrator). Carbon black-DNA hydrogels were prepared according to the protocol described by Xu et al. (35), but an 8 wt % carbon black suspension in place of the reduced graphene oxide was used. Briefly, the 8 wt % carbon black (with 1.5 wt % Arabic gum) was mixed in a 1:1 ratio with a solution of 20 mg/ml salmon sperm DNA (Sigma, CAS: 438545-06-3). The mixture was heated to 90° C. with shaking at 1400 rpm for 10 min, before depositing 1-3 μL via pipette onto inkjet-printed, interdigitated silver electrodes (IDEs). After 5 sec (before significant evaporation could occur), the gel-coated electrodes were submerged in liquid nitrogen and lyophilized for 18-24 h in a benchtop freeze-dryer (Labconco, USA).

Conductivity Measurements of Carbon Black-DNA Gels

To estimate the conductivity of the lyophilized carbon black-DNA gels, samples were prepared on inkjet-printed silver electrodes with an adhesive silicone isolator as a mold. The gels were cast with a length of 2.00 mm, width of 2.00 mm, and height above substrate of 1.00 mm. They were cast such that they spanned a 0.43 mm gap between two printed silver electrodes, and lyophilized in the molds for 24 h. An ohmmeter (Fluke, USA) was used to measure the resistance reading between the silver electrodes spanned by the gel. The two-contact probe method described by Sun et al. (36) was used to calculate the conductivity using the cross-sectional area of the gel and the distance between the probes (Eq. 1), where L is the separation distance (0.43 mm), w is the width (2.00 mm) and t is the height (1.00 mm). By measuring the conductivity of 10 samples, a mean value of 4.2±0.8 mS/cm was obtained:

$$\sigma = \frac{1}{V} \times \frac{L}{wt} \tag{1}$$

In Vitro Reaction of Cas12a with Carbon Black-DNA Gels

To measure the detachment of lyophilized carbon black-DNA gels from a surface, gels were deposited on flexible, inkjet-printed silver electrodes. After lyophilization of the gels for 18 h, the electrodes were placed individually in the bottom of 1.5 ml Eppendorf tubes and then submerged in 75

µL of the Cas12a reaction mix to ensure the gels were completely covered. The aqueous Cas12a reaction mix contained 1×NEB 2.1 buffer, 0.75 µM Ca12a, 1.3 µM gRNA and varying concentrations of the dsDNA trigger (0.05, 0.1, 0.5 and 1.0 µM). A control reaction mix was also prepared that contained 1.0 µM of a scrambled trigger dsDNA sequence. The lyophilized gels were incubated in the Cas12a reaction mixtures at 37° C. for 21 h, with six replicates for each dsDNA trigger concentration (including the control). At 30-min intervals, the Eppendorf tubes were shaken for 10 sec at 800 rpm. After shaking, the silver electrodes were visually inspected and the complete detachment of any gels from the substrate recorded. This experiment was then repeated an additional two times. For the first repeat, dsDNA concentrations of 1.0 and 0.5 µM were used as well as a 1.0 µM scrambled dsDNA control (n=6 for each condition); after 10 h, the reaction was stopped, dried the electrodes in air, and took a resistance measurement. using a multimeter (Model 179, Fluke, USA). For the second repeat, dsDNA concentrations of 0.1 and 0.05 UM were used, as well as a 1.0 µM scrambled dsDNA control (n=6 for each condition); after 21 h, the reaction was stopped, the electrodes were dried in air, and a resistance measurement was taken.
Synthesis of Acrylamide-DNA Gel Precursors Acrylamide-DNA hydrogels were produced using a modified version of a previously described method (37). HPLC-purified single-stranded oligos (Oligo-X and Oligo-Y, described below) functionalized with a methacryl group at their 5'-end were resuspended in water to a final concentration of 3 mM. Linker oligos without functionalization (L0, L5, and L15, described below) were also resuspended in water to a final concentration of 3 mM. A 10× concentrated stock of the reaction buffer was prepared from Bio-Rad 50×TAE buffer supplemented with magnesium acetate (125 mM) such that the final concentrations in the reaction were 1×TAE and 12.5 mM Mg$^{2+}$. Fresh aqueous solutions of 20 v/v % N,N,N',N'-tetramethylethane-1,2-diamine (TEMED, Millipore Sigma, USA) and 2 wt % ammonium persulfate (APS, Millipore Sigma, USA) were prepared before each reaction.
Production of Oligo-Functionalized Acrylamide Polymers Ps-X and Ps-Y Separate reactions of between 50-400 µL were prepared for each oligo X and Y in 1.5 mL Eppendorf tubes (final concentration in brackets). Methacryl-functionalized oligos (1 mM), TAE/Mg2+ buffer (1×) and 40% acrylamide (4%) were mixed in water at room temperature, vortexed briefly to mix, and de-gassed under vacuum for 15 min. APS (0.05 wt %) was then added, the tube was inverted to mix, and the contents were collected by spinning down briefly. TEMED (0.5 v/v %) was then added and the mixing repeated. The reactions were allowed to proceed under vacuum at room temperature for 20 min. Incorporation of DNA oligos into the polymer strands was confirmed by agarose gel electrophoresis. To confirm incorporation of ssDNA into the polyacrylamide backbone, the pre- and post-reaction mixtures were run on an agarose gel (FIG. 7A). For this, a 2% agarose gel containing 1×TAE buffer and SYBR Safe dye was prepared. For ssDNA methacryl-oligos X and Y (FIG. 7 Lanes 3 and 5), a sample from the pre-reaction mix containing 0.2 nmol of oligo was loaded into the wells. The polymerized samples of X and Y (FIG. 7 Lanes 4 and 6) contained 2 µl of the gel precursor polymer dissolved in a total volume of 12 µl of 1× Gel Loading Buffer (NEB). The gel was run for 1.5 h at 80 V in TAE buffer and imaged under UV light using a G: Box Mini (Syngene USA). Ps-X and Ps-Y stocks were stored at 4° C. for up to 2 weeks.

Bulk Gelation of Polyacrylamide (PA)-DNA with ssDNA Linker

Polymer crosslinking can be achieved by mixing a 1:1:0.6 volume ratio of polymer X (PA-DNA-X), polymer Y (PA-DNA-Y) and ssDNA linker (3 mM), respectively, under room temperature conditions, which should produce a reasonably fluid mix. X-Y Polymer solution should be thoroughly mixed and deposited on the desired substrate (e.g., paper) at room temperature. Embedder substrate can be lyophilized or air-dried under ambient conditions for 30 min. Gel crosslinking is triggered by addition of ssDNA linker to X-Y Polymer at room temperature in less than 1 min.
Bulk Degradation of Polyacrylamide-DNA Gels 15 µL gel mixtures were prepared by combining (in order): Ps-X & -Y (4.6 µL), 10×NEB 2.1 buffer (0.75 µL), 2.5 mg/ml FITC-Dextran (500 kDa, 0.75 µL), Cas12a reaction master mix (0.75 µL), 100 µM trigger or scrambled dsDNA (0.75 µl) and 3 mM linker DNA (L-15, 2.8 µL). The Cas12a master mix was prepared on ice and consisted of NEB LbaCas12a (10 µM) and an MRSA crRNA (15 µM) in 1×NEB 2.1 buffer. The final concentrations of the reagents in the 15 µL gels were as follows: 0.5 µM Cas12a, 0.75 UM MRSA crRNA, 0.125 mg/ml FITC-Dextran, 5 µM trigger or scrambled DNA. To enable gelation, the mixtures were heated in 1.5 ml Eppendorf tubes to 37° C. for 10 min and then cooled to room temperature, and then at 4° C. for 5 min. After gelation, a supernatant consisting of 750 µL of 1×NEB 2.1 buffer was added. The final concentrations of the reagents in the wells were as follows: 9.8 nM Cas12a, 14.7 nM MRSA crRNA, 2.45 µg/ml FITC-Dextran, 98.0 nM trigger or scrambled DNA. The reaction tubes were incubated at 37° C. for 18 h, inverted once, and imaged under UV light (Ex: 385 nm; Em: 525 nm) using a G: Box gel imager (Syngene USA). Results are shown in FIG. 7.
Gold Nanoparticle Synthesis and PEG Functionalization Gold NPs were synthesized by reducing chloroauric acid (HAuCl4, Sigma) with sodium citrate (Sigma), following the Turkevich method (38). Briefly, 1 ml of a 6.8 mM sodium citrate solution was added to 50 ml of 0.25 mM gold (III) chloride, while the gold chloride solution was boiling. Samples were stirred and heated for 15 min during which the gold crystals formed. Nanoparticles were left to cool down to room temperature while stirring continued. 0.33 ml of 2 mM, 5 kDa thiol-terminated poly(ethylene glycol) methyl ether (mPEG, Nanocs, USA) was added to the synthesized NPs and allowed to conjugate overnight to thoroughly coat the gold surfaces. NP characterization after synthesis was performed by assessing optical absorption. Spectra of the NPs were obtained on a Cary 300 UV-Vis (Agilent Technologies, USA). Morphology of the NPs was characterized with a FEI Tecnai G2 TEM at 120 kV. ImageJ was used to process the images and measure the dimensions of the NPs. A Zetasizer Nano Zen3600 (Malvern Instruments, UK) was used to measure the hydrodynamic diameter (DH) and the zeta potential (ζ) of the NPs.
Gold Nanoparticle Release from Acrylamide Gels 15 µL gel mixtures were prepared by combining (in order): Ps-X & -Y (4.6 µL), 10×NEB 2.1 buffer (0.75 L), 555 nM PEG-stabilized AuNPs (0.75 µL), Cas12a reaction master mix (0.75 µL), 100 µM trigger or scrambled dsDNA (0.75 µl) and 3 mM linker DNA (L-15, 2.8 µL). The Cas12a master mix was prepared on ice and consisted of NEB LbaCas12a (10 µM) and an MRSA crRNA (15 µM) in NEB 2.1 buffer. The final concentrations of the reagents in the 15 µL gels were as follows: 0.5 µM Cas12a, 0.75 µM MRSA crRNA, 27.75 nM PEG-AuNPs, 5 µM trigger or scrambled DNA. 2.5×2.0 mm Press-to-Seal™ silicone isolators (ThermoFisher Scientific, USA) were cut into single units and attached to the bottom of individual wells in a 24-well tissue culture plate, adjacent to the edge of the wells. The gel mixtures were heated to 37° C. for 10 min and mixed with a pipette tip before being deposited into the isolators in the 24-well plate. The plate was then moved to 4° C. for 15 min to set the gels, and 750 μL of 1×NEB 2.1 buffer added to each well as a supernatant. The final concentrations of the reagents in the wells were as follows: 9.8 nM Cas12a, 14.7 nM MRSA crRNA. 0.54 nM PEG-AuNPs, 98.0 nM trigger or scrambled DNA. Absorbance readings (520 nm) from the 24-well plate were measured every 5 min for 16 h in a plate reader at 37° C.; data was smoothened with a first-order Savitzky-Golay filter.

Cell Encapsulation and Release from DNA-Polyacrylamide Gels

All cell encapsulation and release tests were conducted with K562 cells (American Type Culture Collection, Manassas VA), expanded in RPMI 1640+GlutaMAX™ Medium (Thermo Fisher Scientific, Waltham, MA) supplemented with 10% fetal bovine serum. Cell viability was assessed with calcein-AM and ethidium homodimer-1 (Invitrogen) or Trypan Blue exclusion (Beckman Coulter). Cell encapsulation and viability imaging were performed with a Nikon E800 upright microscope for single-shot bright-field and fluorescence acquisition, and with a Zeiss TIRF/LSM 710 confocal microscope for 3D slice rendering.

Fabrication of CRISPR-Gel μPad Stop-Flow System with Electrical Readout

Paper μPADs were fabricated according to a modified version of the protocol published by Wei, X. et al. (39), using a double-sided wax printing pattern. The top and bottom μPAD wax layers were designed using Illustrator CC (Adobe Inc. San Jose, CA), and printed on Whatman® Grade 1 chromatographic filter paper (Thermo Fisher Scientific, Waltham, MA) using a Xerox Phaser 8560 printer. Printed μPAD sheets were wax reflowed through hot pressing for 15 sec at 125° C. using a Cricut EasyPress™ (Cricut Inc., Fork, UT), and then cooled to room temperature. Individual μPADs were then cut and folded as shown in FIG. 4. Layers 1 to 4 of the μPAD exhibit circular hydrophilic paper regions of 1.5 mm in diameter, while layer 5 contains a 1.5×30 mm lateral flow channel with marked lengths. First, layer 3 was filled with 0.5 μL of oligo-functionalized acrylamide polymer solution containing both Ps-X and Ps-Y (1:1). Then layer 4 was filled with PBS buffer containing food color dye (0.5 μL, 1:5 red dye/PBS). Paper μPADs with deposited reagents in layers 3 and 4 were then freeze-dried before continuing assembly. Layer 5 of the μPADs was then covered with 3×30 mm strips of 87580-Nickel/Copper Conductive Fabric Tape (Laird Technologies EMI, Pall Mall, London) placed along the top and bottom sides of the lateral flow channel to act as parallel conductive planes to measure channel electrical resistance as a function of buffer wicking distance. Both the conductive tape and wiring for connection were laminated over layer 5 using plastic tape to prevent detachment. Layer 1 and layer 2 of the μPADs were left uncovered to receive the conductive buffer and DNA linker during testing.

Flow and Conductivity Measurements in μPad

At the time of testing, layer 2 of the μPADs was filled with 0.3 μL of ssDNA linker (100 μM) pre-incubated for 4 hrs at 37° C. in a cutting solution containing Cas12a (300 nM), MRSA crRNA (1 μM), dsDNA MRSA Trigger (0 nM, 0.4 nM, 2 nM, 10 nM, 50 nM) and NEB Buffer 2.1 (1×). Positive controls to validate enzyme activity during Cas12a-mediated cleavage were performed in parallel reactions and contained Cas12a (300 nM), MRSA crRNA (1 μM), dsDNA MRSA Trigger (0 nM, 0.4 nM, 2 nM, 10 nM, 50 nM) and NEB Buffer 2.1 (1×), as well as 750 nM ssDNA quenched fluorescently labeled reporter. The products of these reactions are not used in μPAD measurements. However, the fluorescence readings were used as a proxy to estimate the cleavage yield of the ssDNA bridge upon Cas12a activation (FIG. 16). After the ssDNA bridge was digested, the entire μPAD assembly was collapsed to fluidically connect all hydrophilic regions in the μPAD with layer 1 acting as a protective cover for all other layers and as the inlet for 10 μL of running PBS buffer. μPAD channel resistance was continuously monitored using a 34411A Digital Multimeter (Keysight Technologies Inc., Santa Rosa, CA) for dynamic measurements (FIG. 4) and endpoint values were taken at 5 min for determining the sensitivity curve (FIG. 4). Testing of flow and conductivity measurements in the μPad were conducted in triplicate. Representative samples of paper μPAD regions with visible polyacrylamide-DNA gelation due to the presence of uncut DNA linker is shown using a scanning electron microscope (SEM) and compared to ungelled regions where cut ssDNA linker was present.

RFID Integration in CRISPR-Mediated Stop-Flow μPad

A CRISPR-active RFID sensor was constructed by modifying a 10×70 mm flexible WRL-14147 ultrahigh-frequency (UHF) RFID tag (SparkFun Electronics Inc., Niwot, CO) with a flexible interdigitated electrode capable of short-circuiting the tag antenna in the presence of conductive buffer at the fourth layer of the previously described μPAD. The flexible interdigitated electrode was fabricated using a silver nanoparticle ink pattern (FIG. 13), deposited over a polyethylene terephthalate NanoBenefit 3G Series film (Mitsubishi Imaging MPM Inc., Rye, NY) using a previously reported conductive inkjet printing method (40). Both electrode terminals were electrically connected to the first loop regions at the RFID tag antenna in proximity to the UHF-RFID chip (see figure). A modified four-layer μPAD stack (without layer 5), was assembled on top of the RFID device as a flow-through arrangement, aligning the bottom of the hydrophilic region in layer 4 to be in contact with the interdigitated electrode. Reagent placement and activation were performed as with the PAD flow & conductivity measurements previously described. Relative received signal strength (RSSI) of the RFID tag was measured in the presence or absence of target DNA after incubation in the cutting solution containing Cas12a, crRNA, and linker DNA. Reduction in absolute RSSI values indicates that the power level of the received radio signal has decreased due to conductive buffer flow and RFID tag antenna short-circuiting. As proof-of-concept of this effect, the RSSI was continuously measured for two independent tags placed at a distance of 1 m from a WRL-14131 UHF-RFID TNC antenna (SparkFun Electronics Inc., Niwot, CO) connected to a M6E-NANO simultaneous RFID tag reader (SRTR) (ThingMagic Inc. Bedford, MA) and an Arduino Uno microcontroller (Arduino LLC, Somerville, MA) using the M6E-NANO RFID Arduino library.

DNA and RNA Sequences

For this study, all DNA oligonucleotides were obtained from Integrated DNA Technologies. Cas12a crRNA was produced by in vitro transcription using an HiScribe T7 transcription kit (NEB) and oligonucleotide templates; gRNAs were subsequently purified using an RNA Clean & Concentrator kit (Zymo Research).

The guide had the following sequence:

```
                                    (SEQ ID NO: 1)
5' GGGUAAUUUCUACUAAGUGUAGAUUUAAAGAAGAUGGUAUGUGG 3'.
``` dsDNA triggers were ordered pre-hybridized and had the following sequences:

Matching trigger dsDNA:

```
                                    (SEQ ID NO: 2)
5' TTTAATTTTGTTAAAGAAGATGGTATGTGGAAGTTAGATT 3'.
```

Scrambled dsDNA sequence (obtained by randomly rearranging the sequence of the dsDNA trigger, while preserving length and overall GC content):

```
                                    (SEQ ID NO: 3)
5' TAGTAGTGATTATGTTAGATAGTGAATAGGTTTAATGTAT 3'.
```

Single-mismatch dsDNA trigger:

```
                                    (SEQ ID NO: 4)
5' TTTAATTTTGTTAAAGAAGATGTTATGTGGAAGTTAGATT 3'.
```

Three-mismatch dsDNA trigger:

```
                                    (SEQ ID NO: 5)
5' TTTAATTTTGTTAAATAAGATGTTATGTAGAAGTTAGATT 3'.
```

The quenched fluorescently-labeled reporter for Cas12a cleavage experiments in solution: 5' (6FAM) TTATT (Iowa Black™ FQ) 3'

For Cas12a-mediated release from PEG-based hydrogels, the following oligonucleotides were used:

For ssDNA degradation-mediated release:

```
                                    (SEQ ID NO: 6)
5'(C6Amine)AGCTTGTCTGCCATGGACATGCAGACTATACTGTTATT

GTTGTACAGACCGAATTCCC 3'.
```

```
                                    (SEQ ID NO: 7)
5'(6FAM)AGGGAATTCGGTCTGTACAACAATAAC 3'.
```

For dsDNA degradation-mediated release:

```
                                    (SEQ ID NO: 8)
5'(C6Amine)TTTAATTTTGTTAAAGAAGATGGTATGTGGACGTATGG

AATAAGTG;
```

```
                                    (SEQ ID NO: 9)
5'(6FAM)TCACTTATTCCATACGTCCACATACCATCTTCTTTAACAAA

ATTAA;
And:
```

```
                                    (SEQ ID NO: 10)
5'(C6Amine)TTATTATTTACAACGTCGTGACTGGGAAAACCCTTGGA

ATAAGTG;
```

```
                                    (SEQ ID NO: 11)
5'(HEX)TCACTTATTCCAAGGGTTTTCCCAGTCACGACGTTGTAAATA

ATA.
```

Oligonucleotides used for the fabrication of polyacrylamide-DNA gels:

```
Oligo-X:
                                    (SEQ ID NO: 12)
5' (Acrydite ™)TTATTCTTGTCTCCCGAGAT 3';

Oligo-Y:
                                    (SEQ ID NO: 13)
5' (Acrydite ™)TTATTTCACAGATGAGTATC 3';

L0:
                                    (SEQ ID NO: 14)
GATACTCATCTGTGAATCTCGGGAGACAAG;

L5:
                                    (SEQ ID NO: 15)
GATACTCATCTGTGATTATTATCTCGGGAGACAAG;

L15:
                                    (SEQ ID NO: 16)
GATACTCATCTGTGATTATTTTATTTTATTATCTCGGGAGACAAG.
```

Example 9. Introduction

Microbial clustered regularly interspaced short palindromic repeats (CRISPR) and CRISPR-associated (Cas) adaptive immune systems contain RNA-guided endonucleases capable of multiple-turnover nucleic acid hydrolysis (1, 2). Due to their specificity and programmability CRISPR-Cas enzymes have been exploited as efficient genome editing tools (3) and more recently in nucleic acid diagnostic applications such as SHERLOCK (4, 5) and DETECTR (2).

Biologically responsive materials are important for biotechnology applications, including the fabrication of scaffolds for tissue engineering (6), the actuation of microfluidic valves (7), and the detection of analytes in sensors (8, 9). DNA-responsive hydrogels are well suited to interface with synthetic DNA constructs or naturally occurring extracellular DNA (10). Current DNA-responsive hydrogels typically rely on strand-displacement or structural changes in DNA cross-linkers (11, 12), which require high concentrations of DNA triggers for actuation. Adapting such DNA-hydrogels for activation with new trigger sequences involves the modification of nucleic acid components which can conflict with the structural requirements (e.g., length, secondary structure) imposed by the material. This limits the programmability of these systems, and highlights the need for a strategy that uncouples structural and sensing constraints in DNA-based materials.

As described herein, CRISPR-associated enzymes were used to control the properties of hydrogels with integrated DNA components at multiple scales and in a modular fashion. The need to encode target sequence specificity into the gel structure is, thus, eliminated. The material platform is able to induce changes in hydrogels in response to user-defined target nucleic acid sequences by replacing a single component—a CRISPR guide RNA (gRNA) that governs sequence-specific Cas activation. Different DNA-based materials were engineered to demonstrate a variety of nuclease-mediated responses including the release of small molecules, enzymes, nanoparticles (NPs) and live cells, as well as the modulation of bulk electrical and permeability properties of DNA-hydrogels for sensing and diagnostics (FIG. 21).

Example 10. Cas12a has Both Targeted and Collateral DNase Activities

The Cas12a from Lachnospiraceae bacterium ND2006 (LbaCas12a) (1, 2) was used that displays two activities: a specific cleavage activity towards double-stranded DNA (dsDNA) fragments matching the gRNA spacer sequence (targeted cleavage) and a subsequent indiscriminate single-stranded DNA (ssDNA) hydrolysis activity (collateral cleavage) (FIG. 17A). Once the Cas12a-gRNA complex binds and cleaves its dsDNA target, the collateral cleavage of nearby ssDNA by Cas12a is highly efficient (~1250 turnovers per second). To demonstrate the target programmability of CRISPR-gels, gRNAs were designed and screened to detect fragments of the mecA antibiotic-resistance gene of methicillin-resistant *Staphylococcus aureus* (MRSA). MRSA was selected as a clinically relevant model to demonstrate the target programmability of CRISPR-gels, given the high concentration of extracellular DNA in MRSA biofilms (41).

Validation of the collateral cleavage activity of Cas12a-gRNA in solution was first performed. Cleavage of a ssDNA reporter containing a quenched fluorophore by Cas12a in response to mecA dsDNA triggers confirmed the performance of the MRSA1 gRNA (FIG. 22). Cas12a programmed with this gRNA detected its cognate trigger down to a concentration of ~16 pM in solution (FIGS. 23A-23F) and was selected among other targets for subsequent experiments. Sequence mismatches between the gRNA and trigger reduced the collateral cleavage rate, consistent with previously reported patterns (2, 13). Non-specific activation of Cas12a by a scrambled dsDNA sequence was over 100-fold lower than that by the mecA trigger (FIGS. 23A-23F). Cas12a's high dsDNA target specificity and rapid nonspecific ssDNA collateral cleavage activity make it an ideal candidate for modulating a wide range of physical and mechanical hydrogel properties (FIG. 21).

Programmable materials capable of the controlled release of soluble compounds, as well as encapsulated cells, have broad utility in various therapeutic and research applications (14-17). Due to the diversity of DNA-based hydrogels in the literature (TABLE 1), material formulations were selected that span a wide range of physical properties to demonstrate that they could be actuated by Cas proteins (TABLE 2): (1) poly(ethylene glycol) (PEG) hydrogels with covalently bound nonstructural DNA pendants that are released by Cas12a nuclease activity without degrading the overall hydrogel structure; (2) acrylamide hydrogels with structural ssDNA cross-links that could be cleaved by Cas12a resulting in bulk gel degradation, as well as particle or cell release; and (3) conductive hydrogels loaded with carbon black that were cleaved from the surface of electrodes by Cas12a, thus behaving like an electronic fuse.

TABLE 1

Examples of DNA hydrogels in the literature.

| Publication | Material | Actuation mechanism | Readout | Sensitivity | Timescale | Application |
|---|---|---|---|---|---|---|
| 53 | DNA-acrylamide hydrogel | Hg2+ dependent DNAzyme | Electrochemistry | 0.042 pM | 120 minutes for hybridization chain reaction | electrochemical impedance biosensor for detection of Hg2+ |
| 54 | DNA-only hydrogel from scaffold and linker | Thermal control Enzymatic degradation | Sol-gel transition | 1.5 U/µl BamHI/EcoRI | 48 hour digestion | Thermal and enzymatic responsive materials |
| 55 | DNA-metal nanoparticle hydrogel from scaffold and linker | Magnetic field Enzymatic degradation | Remote-controlled gel movement Sol-gel transition | 45 U EcoRI 52N magnet | 48 hour digestion 48 hour exposure to magnet | Degradable, magnetically controllable material |
| 56 | DNA-acrylamide hydrogel | Enzymatic cleavage & triggered release | Oligonucleotide release using electrophoresis | 10 U/µl BamHI/EcoRI | 10 hour digestion | Release of tethered anti-HIV deoxyribozyme |
| 57 | DNA-only hydrogel | Triggered gel formation | Gel is a signal blocker for electrochemical readout | 3.5 fM PDGF (10 fM-10 nM linear range) | 120 minute incubation time | Electrochemical detection of PDGF |
| 58 | DNA and disulfide cross-linked acrylamide hydrogels | DNA strand-displacement and chemical reduction (TCEP) | Release in FITC-dextran from hydrogels Rheological measurements | DNA: 56 µM TCEP: ~60 mM | TCEP: 82% release in 10 hours, 95% in 149 hours DNA: 43% release in 10 hours, 70% in 149 hours | Sequence-specific DNA triggered release from hydrogels |
| 59 | DNA-acrylamide/bis-acrylamide hydrogel | Toehold strand displacement | Interferometry measurement of gel swelling | Trigger ssDNA: 20 µM | ~1.5 hour incubation | Bioresponsive materials |

TABLE 1-continued

Examples of DNA hydrogels in the literature.

| Publication | Material | Actuation mechanism | Readout | Sensitivity | Timescale | Application |
|---|---|---|---|---|---|---|
| 60 | Polyacrylamide functionalized with DNA, hybridized to a DNA aptamer | Enzymatic degradation | Microscopy detection of capture and release of live cells | 5 U/μL BamHI | 30 minute incubation | Sequence-specific release of CCRF-CEM and Ramos cells from a gel surface |
| 49 | DNA-PEG hydrogel | Enzymatic degradation | Fluorescence microscopy and quartz crystal microbalance analysis | 0.03 U/uL DNase I | 9 hour digestion | Enzymatic responsive materials |
| 39 | DNA-acrylamide hydrogel | Small-molecule and metal-ion aptamers cross linking aDNA-acrylamide hydrogel | Stopped-flow microfluidic device with colorimetric readout | Cocaine: 50 μM Adenosine: 100 μM Pb2+: 200 nM (simultaneously) | 6 minutes | Low-cost, paper-based sensor for small molecules and metal ions |
| 7 | DNA-only hydrogel from RCA | Gel formation on hybridization of pathogen ssDNA and initiation of RCA results in blockage of a fluidic channel | Colorimetric readout of flow using dye | ssDNA: 0.019 pM (Dengue, MERS, Ebola, Zika sequence) | 15-30 minute incubation | Low-cost fluidic sensor for detection of pathogen ssDNA |

TABLE 2

Summary of materials.

| | PEG Gel Anchored-molecule Release | PA Gel AuNP Release | PA Gel Bulk Degradation | PAEncapsulated Cell Release | DNA-Carbon Black Gel Degradation On Electrodes | PA Gel uPAD Flow-Based Detection |
|---|---|---|---|---|---|---|
| LOD | 80 pM | In-gel: 3.3 μM Total: 40 nM (includes supernatant) | 200 nM | 200 nM | 500 nM | 400 pM Unamplified, 11 aM Pre-Amplified |
| Payload/ Signal Type | Small Molecule, Protein | Nanoparticles | Small Molecule (Bound to Gel) | Live Cells (Human, Primary) | Conductivity Change | Conductivity Change, Visual Change in Dye Flow |
| Trigger location | Supernatant | Gel (pre-loaded) | Supernatant | Supernatant | Supernatant | Diagnostic sample |
| Cas12a-gRNA location | Supernatant | Gel (pre-loaded) | Supernatant | Supernatant | Supernatant | Pre-incubation mix |
| Time to 50% Change/ Signal | 1.5 Hours (fluorophore release) | 5 Hours | 1 Hour | <1 Hour | 5 Hours | N/A |
| Sample-to-decision time | 10 min reaction + 5 min colorimetric detection (HRP release) | N/A | N/A | N/A | N/A | 4 h incubation + 1 min read |
| Conductive? | Non-conductive | Non-conductive | Non-conductive | Non-conductive | Conductive (dry) | Conductive buffer flow |
| Gel Cross-linker Degradation vs Anchor Degradation | Anchor Degradation | Cross-linker Degradation | Cross-linker Degradation | Cross-linker Degradation | Gel detachment | Cross-linker Degradation |

TABLE 2-continued

Summary of materials.

| | PEG Gel Anchored- molecule Release | PA Gel AuNP Release | PA Gel Bulk Degradation | PAEncapsulated Cell Release | DNA-Carbon Black Gel Degradation On Electrodes | PA Gel uPAD Flow-Based Detection |
|---|---|---|---|---|---|---|
| Material Synthesis Complexity | Simple | Moderate | Moderate | Moderate (Additional Wash Steps) | Simple | Moderate |

PA: polyacrylamide.

Example 11. Collateral Cas12a Activity Releases ssDNA-Anchored Cargos from Hydrogel Matrices The targeted dsDNA cleavage activity of Cas12a can be used to preferentially release anchored cargos with near-single turnover (FIG. 24), however focus was maintained on the collateral ssDNase activity of the enzyme as it allows for the efficient transduction of external stimuli into changes in material properties through catalytic signal amplification. To illustrate the programmable actuation of materials using Cas12a, a small-molecule reporter (Cy3 fluorophore) was covalently tethered into PEG hydrogels through a ssDNA linker (FIG. 17B), and its release into solution was monitored (FIGS. 25A-25B) upon Cas12a-induced cleavage. The Cas12a-gRNA complex was insufficient to catalyze cargo release, however introduction of the mecA dsDNA trigger initiated the hydrolysis of the ssDNA anchors (FIG. 17C and FIGS. 26A-26E). In contrast, a randomly permutated version of the mecA dsDNA (scrambled control) failed to do so. Horseradish peroxidase (HRP) enzyme was then used as a model for larger biomolecule payloads, demonstrating that biological function was preserved after immobilization in hydrogels using ssDNA anchors and subsequent release by Cas12a (FIG. 17D). Within 10 minutes of exposure to a low-concentration (10 nM) dsDNA stimulus, sufficient HRP activity was detected in the supernatant for a visual readout (FIG. 17D, inset). Further incubation allowed the discrimination of trigger and scrambled dsDNA down to 100 pM (FIG. 27). These experiments are consistent with the efficient ssDNAase activity of activated Cas12a (2).

To demonstrate that changes to the gRNA were sufficient to entirely reprogram the target responsiveness of the material, gRNAs were designed to target a panel of genes involved in *S. aureus* antibiotic-resistance mechanisms (FIGS. 28A-28D). These include the antibiotic resistance genes ermA, and ermC (42, 43), the virulence factor gene spa (44) and the vancomycin-resistance gene vanA (45). Out of 25 combinations of gRNAs and dsDNA, those where the sequence of the trigger matched the gRNA resulted in substantially higher fluorophore payload release from the hydrogel matrix (FIG. 17E). These results correlated to similar observations of the reactions performed in solution (FIGS. 29A-29F), and suggest that different gRNA-trigger pairs activate Cas12a to different extents (2).

For many applications, the rate at which a molecule is delivered from a carrier conveys important biological information (14). It was found that the speed of CRISPR-mediated hydrogel actuation corresponds to the amount of input dsDNA (FIG. 17F). Conversely, for a given level of input, the response dynamics can be hard-coded into the system by altering the properties of the starting material. For example, pore size is expected to alter the mobility of macromolecules in polymer networks (46). Based on the macroscopic observations of programmed anchor hydrolysis (FIG. 30), it was hypothesized that this could be used to further tune the relationship between dsDNA input and Cas12a-mediated response. By modulating the cross-linking density of a PEG-DNA hydrogel and measuring the rate of fluorophore release by Cas12a-gRNA, a further strategy was established by which the behavior of the CRISPR-responsive material could be controlled (FIG. 17G, FIGS. 31A-31C, and FIG. 32).

In addition to controlling global dynamics of ssDNA cleavage through bulk material properties, the sequence-defined, addressable nature of the ssDNA linkers and the collateral cleavage activity of Cas12a for ssDNA over dsDNA was capitalized upon. (1, 2).

Two orthogonal reporter molecules (Cy3 and 6-carboxyfluorescein fluorophores) were attached into PEG hydrogels with distinct ssDNA linkers. The differential sensitivity of one linker was then pre-programmed over the other to Cas12a collateral degradation by hybridizing it with a complementary blocking strand in situ. While the release of the unprotected fluorophore was unaffected, the speed of release of the hybridized reporter was significantly reduced (FIG. 17H and FIG. 33).

Example 12. Collateral Cas12a Activity Alters the Large-Scale Mechanical Properties of DNA Hydrogels The high catalytic efficiency of dsDNA-activated Cas12a-gRNA ($k_{cat}/K_m \sim 1.7 \times 10^9$ s$^{-1}$M$^{-1}$) (2) makes it well-suited for converting dsDNA signals into bulk material changes. To demonstrate this, DNA cross-linked polyacrylamide (PA) hydrogels (9, 47) were designed by separately incorporating two non-complementary oligonucleotides into polyacrylamide chains (FIGS. 34A-34C). The polyacrylamide-DNA (PA-DNA) were then cross linked with precursors using an oligonucleotide strand that forms bridges between the PA-DNA chains. These cross-links contained single-stranded AT-rich Cas12a collateral cleavage sites (FIG. 18A). In these hydrogels, degradation of the DNA cross-links physically disrupts the polymer networks (FIG. 21) (46, 48).

The Cas12a-induced degradation of PA-based CRISPR-gels was initially evaluated with a DNA-intercalating dye to label bridge sequences in PA-DNA gels and track gel integrity. The bridges were degraded upon exposure to gRNA-Cas12a and trigger dsDNA, as revealed by the dissipation of gel fluorescence at rates dependent on trigger concentration (FIG. 18B). Compared to experiments performed in solution, gel degradation appeared to be more robust to the introduction of sequence mismatches between the gRNA and dsDNA trigger (FIGS. 23A-23F and FIG. 35). Using FITC-dextran particles physically entrapped in the hydrogel, visualize of the degradation of millimeter-scale PA-DNA hydrogels was achieved (FIG. 36).

Programmable degradation of PA-DNA hydrogels was assessed by testing 25 combinations of different gRNAs and dsDNA triggers. Consistent with the non-destructive cargo release experiments (FIG. 17E), PA-DNA hydrogel degradation occurred only when the gRNA and dsDNA sequences were complementary (FIG. 18C and FIGS. 37A-37E), demonstrating Cas12a-gRNA's ability to discriminate between inputs.

Though biomolecules can be tethered to materials through well-defined, single linkers, physical entrapment in a polymer matrix represents a more general strategy to control the release of larger payloads. The dsDNA-triggered, Cas12-mediated release of nanoparticles was tested by encapsulating 18-nm PEG-coated gold NPs (AuNPs) (FIGS. 25A-25B and FIGS. 38A-38C) in PA-DNA hydrogels. Loading gels with both Cas12a-gRNA and a dsDNA trigger led to total nanoparticle release via Cas12a activation and gel degradation, whereas gels loaded with a scrambled dsDNA trigger showed no significant release of AuNPs relative to a buffer-only background (FIG. 18D and FIGS. 39A-39D). This was consistent with the disruption of the percolated network upon cross-link cleavage (49, 50).

The complex interactions between cells and surrounding materials have implications for tissue engineering and other therapeutic applications. It was reasoned that if Cas12a-gRNA would have the capacity to modify the extracellular matrix of cells encapsulated in DNA materials in response to pre-defined cues. The reversible encapsulation of human primary peripheral blood mononuclear (PBMC) cells in PA-DNA hydrogels was tested by exposing the gels to activated gRNA-Cas12a. Complete gel degradation and cell release were observed within 2 hours in the presence of 1 µM dsDNA trigger (FIG. 18E and FIG. 40), without compromising cell viability (FIGS. 41A-41C and FIGS. 42A-42B). Conversely, gels exposed to a scrambled dsDNA control remained intact within the same timeframe. These results demonstrate that nanoparticles and live cell payloads can be immobilized in biocompatible hydrogels and released upon addition of trigger dsDNA sequences without the need for hydrogel redesign to accommodate different input signals.

Example 13. Conductive DNA-Based Materials Act as Cas12a-Actuated Electronic Fuses Cas12a was used to modulate the attachment of a conductive DNA-based hydrogel to an electrode surface to act as an electrical fuse triggered by specific DNA sequences (FIG. 19A and FIG. 21). A conductive, biologically responsive hydrogel may be desirable for a variety of sensing and diagnostic applications where the direct interface to electrical devices (e.g., analog circuits and microcontrollers) is required. These conductive, self-assembled materials consisted of ssDNA networks cross-linked with carbon-black (CB) conductive nanoparticles (CB-DNA gels). CB is composed of 10-100 nm spherical particles (18) containing graphitic-like domains (19). CB is widely used in industrial applications to impart electrical conductivity to insulating polymers (20) and was used here as a conductive cross-linker in the hydrogels. CB-DNA gels were synthesized through thermal melting of dsDNA followed by cooling in the presence of CB nanoparticles. This leads to the strong, non-covalent association of the aromatic DNA nucleotides with nearby CB graphitic surfaces (21) through hydrogen bonding and π-π stacking interactions (22-24). In these hydrogels, DNA behaves as the main structural component capable of linking carbon black particles together to form a robust, three-dimensional network (22, 25).

It was hypothesized that cleavage of the ssDNA at the electrode-material interface by Cas12a would disrupt the conductive path. To test this system, CB-DNA droplets were spotted onto printed interdigitated silver electrodes and lyophilized (FIG. 19A). Before Cas12a-mediated degradation, lyophilized CB-DNA hydrogels showed high conductivity (~4 mS/cm), comparable to that reported for graphene-DNA gels of similar compositions (33). After initial electrical testing. CB-DNA gels were incubated in a solution containing Cas12a, gRNA and dsDNA trigger. The integrity of CB-DNA hydrogels were visually monitored during Cas12a-mediated detachment (FIG. 19B), tested for conductivity (FIG. 19C), and imaged the electrodes (FIG. 19D and FIG. 43A) with increasing concentrations of dsDNA inputs. Cas12a-gRNA with 500 nM dsDNA trigger was able to completely detach 60% of the hydrogels from electrodes in 10 hours, and 100% of hydrogels after 20 hours. Incubation with a higher dsDNA trigger concentration (1 µM) led to CB-DNA detachment from 100% of electrodes within 10 hours. Complete detachment resulted in an opening of the circuit across the electrode, while partial detachment of the CD-DNA hydrogels at lower dsDNA trigger concentrations led to intermediate conductivities (FIGS. 19C and D, and FIG. 43A). Exposure of electrodes with CB-DNA gels to a ssDNA-specific nuclease resulted in a similar response, confirming that detachment was a consequence of Cas12a activation and ssDNA hydrolysis (FIGS. 43A-43E). This inexpensive CB-DNA gel formulation provides a direct link between dsDNA triggers and electrical outputs.

Example 14. Cas12a-Controlled Hydrogel Formation in a Paper Fluidic Device Enables Diagnostic Readouts A tunable PA-DNA hydrogel was used to control the permeability and electrical readout of a paper-based microfluidic device (FIG. 24). Paper-based technologies have shown promise for point-of-care diagnostics as they are low cost, equipment-free, and easy to use (26, 27). The CRISPR-gel device (FIG. 24 and FIGS. 44A-44B) expands on the concept of paper fluidic chips (µPADs) that rely on the capacity of hydrogels obstruct flow through porous channels (28).

The layers of the device were folded to create a multi-layered structure in which the hydrophilic regions are topologically aligned. Capillary-driven flow through the device terminated in a fifth layer where the output was measured (FIG. 20A and FIGS. 44A-44B). In this system, an intermediary layer contains PA-DNA gel precursors (Ps-X and Ps-Y) that, when mixed with ssDNA cross-linker, form a hydrogel in the paper channels (29, 30). The extent of gel formation, and therefore the rate of buffer flow, is dependent on the extent of degradation of the ssDNA gel cross-linker during a pre-incubation step. The activation of Cas12a can be confirmed by adding a fluorescent ssDNA reporter (FIG. 45). By degrading the cross-linker using Cas12a, it was possible to couple the level of buffer flow to the concentration of dsDNA trigger added to a 4-hour incubated Cas12a reaction.

When nonspecific dsDNA trigger is present during pre-incubation, ssDNA cross-linkers are not cleaved, allowing for hydrogel assembly in the microchannel (FIG. 20A and FIG. 46). Conversely, in the presence of a specific dsDNA trigger, unimpeded flow can be visually detected by adding dyes to the µPAD device. The rate of buffer flow through a μPAD was found to be inversely related to the concentration of a MRSA dsDNA trigger. Using this visual output, it was possible to detect dsDNA concentrations down to 400 pM (FIG. 46).

To optimize the CRISPR-μPAD for field diagnostic applications, reverse transcription (RT) was used to expand the range of detectable biomarkers to RNA, and coupled the RT to an isothermal amplification (RPA) step to improve the limit of detection. RT-RPA followed by a μPAD readout was used to detect synthetic Ebola genomic RNA (52) down to 11 aM (FIG. 20B), a sensitivity matching other state-of-the-art CRISPR-based diagnostics (FIG. 47) (2, 4, 5). This approach is promising for point-of-care diagnostics and has overall better performances in terms of sensitivity, portability and cost than other molecular diagnostics (TABLE 3).

Visual readouts of buffer flow are commonly used, yet they are difficult to couple to downstream hardware for data tification (RFID) module was incorporated into the μPAD. The original design was modified such that buffer flow would short-circuit an interdigitated silver electrode, thereby modulating the efficiency of signal transmission by a flexible RFID tag (FIG. 20D and FIGS. 48A-48D).

An experimenter-blinded trial was then conducted consisting of twelve samples (containing either 11 aM or 0 aM Ebola ssRNA amplified by RT-RPA) divided across three geographic locations (FIG. 20E and FIG. 49). The experimenter pre-incubated the samples with Cas12a and Ebola-specific gRNA for 4 hours, and then recorded the RFID-μPAD signals over the course of 2 minutes. Buffer flow through the μPAD in Ebola-positive samples caused RFID tag antenna short-circuiting, which was detected in real-time as a change in the signal strength compared to an unmodified reference RFID tag (FIG. 20E). All positive and negative samples were correctly assigned using the RFID-μPAD (FIG. 49).

TABLE 3

| | | | | | | | | |
|---|---|---|---|---|---|---|---|---|
| | | | | Comparison of diagnostic technologies. | | | | |
| | qPCR | NGS | MA/FB | FISH | CRISPR-chip | Toehold switches | SD | uPAD-CRISPR materials |
| Cost | High | High | High | High | Mid | Low | Low | Low |
| Ease of Use | Spec | Spec | Spec | Spec | Spec | Simple | Simple | Simple |
| Readout | Fluor | Fluor | Fluor | Fluor | Spec | Visual/ Fluor | Visual/ Fluor | Digital and/or Visual |
| Sensitivity | atto | atto | atto | atto | Femto | femto | atto | atto |
| Time | ~3 Hour | days | 1 day | 4-16 h | 15 min (read) | 1-4 Hour | ~1-3 Hour | ~1-4 Hour |
| Multiplex | Yes | Yes | Yes | Yes | No | Yes | Yes | Yes |
| Quant. | Yes | Yes | Yes | yes | Limited | Limited | Limited (for visual output) | Yes |

NGS: Next Generation Sequencing;
MA: microarray;
FB: fluorescent barcodes;
FISH; fluorescence in situ hybridization;
SD: Sherlock detector;
spec: specialist;
fluor: fluorescent;
atto: attomolar;
femto; femtomolar processing. To overcome this limitation, the CRISPR-actuated fluidic system was modified to read buffer flow as an electric signal (FIG. 20B and FIGS. 44A-44B). The microfluidic channel in the final layer was sandwiched between two electrodes and connected to an ohmmeter (FIG. 20A and FIG. 44B). Electrical conductivity between the electrodes relied on electrolytes provided by the flowing buffer and was directly correlated to the buffer penetration length in the μPAD channel (FIGS. 48A-48D) (31). Using this approach, sub-nanomolar concentrations of dsDNA trigger were successfully detected at a 5-minute end-point, without DNA amplification, demonstrating the potential of the CRISPR μPAD for embedded sensor applications (FIG. 46 and FIGS. 48A-48D). Non-specific dsDNA trigger did not activate Cas12a, thus leaving the electrical circuit open (FIG. 20B and FIGS. 48A-48D). The pre-incubation time required to observe a signal was reduced to 1 hour by tuning the properties of the acrylamide precursors (FIGS. 48A-48D).

The wireless, decentralized logging of individual clinical tests during infectious disease outbreaks could address challenges with record keeping and logistics. To integrate CRISPR-Cas reactions with electronic monitoring systems through hydrogel actuation, a wireless radio-frequency iden- Example 15. Discussion Taken together, these studies demonstrated several strategies to interface biological signals with materials that combine the inherent programmability of CRISPR-associated enzymes with hydrogel systems. These strategies offer control over a variety of complex behaviors and properties, including the release of molecules, nanoparticles, and live cells, as well as bulk hydrogel degradation, electronic signal transduction, and microfluidic valve actuation. By exploiting the enzymatic properties of Cas12a, a platform has been designed that improves upon hydrogel programmability and versatility as only the gRNA molecule needs to be changed to allow hydrogel response to a user-defined DNA sequence. The catalytic activity of Cas12a improves sensitivity compared to DNA-responsive hydrogels requiring stoichiometric amounts of DNA triggers for material activation. Finally, these studies demonstrate various forms of output that expand the capabilities of CRISPR-responsive materials and enhance existing biomaterial-based approaches for tissue engineering, molecular diagnostics, and bioelectronic interfaces with programmable readouts.

Example 16. Materials and Methods for Examples
9-15

In Vitro Cas12a Reagent Validation with ssDNA

Collateral degradation of non-target ssDNA upon Cas12a
was measured in solution by mixing trigger dsDNA with
Cas12a-gRNA complex and using a quenched, fluorescently
labeled reporter. The Cas12a-gRNA complex was assembled
by incubating 200 nM Cas12a with 250 nM gRNA in
1×NEB 2.1 buffer at 37° C. for 10 min. To initiate the
reaction, the Cas12a complexes were mixed with dsDNA
triggers and a quenched, ssDNA fluorescently labeled
reporter (FQ reporter: 5' (6FAM)-TTATT-(Iowa Black™
FQ) 3') to final concentrations of 50 nM Cas12a, 62.5 nM
gRNA, 750 nM FQ reporter and dsDNA triggers in NEB 2.1
buffer. Reactions (3 µl, 384-well microplate) were incubated
in a fluorescence plate reader (Biotek NEO HTS) for 120
min at 37° C. Fluorescence readings were recorded every 2
min (Ex: 485 nm; Em: 535 nm).

Synthesis and Digestion of PEG Hydrogels with Reporter
DNA (General Method for FIGS. 17A-17H)

With the exception of explicitly mentioned protocol varia-
tions, DNA-decorated PEG hydrogels were produced as
follows:

a. DNA-thiol reduction. 0.5 µl of tris(2-carboxyethyl)
phosphine (TCEP, 0.5M solution, pH7, Millipore
Sigma) was mixed with 10 µl of double-functionalized
reporter oligonucleotides (5'-C6-Thiol,3'-Cy3 oligos,
custom-synthesized, HPLC purified, Integrated DNA
Technologies) resuspended at 500 µM in water. The
solution was then incubated for 3.5 h in the dark at
room temperature to reduce the disulfide groups on the
DNA.

b. DNA grafting on PEG precursors. A fresh stock of
8-arm vinyl sulfone-activated PEG (PEG-VS, MW10
kDa, JenKem Technology) was prepared by resuspend-
ing aliquots of PEG-VS powder at 4% w/v (assuming
a PEG density of 1.1) in 1 M triethanolamine (pH 8).
125 µl of PEG-VS stock was added to the reduced DNA
solution and incubated in the dark at room temperature
for about 18 h, to allow the base-catalyzed Michael
addition of thiols on the vinyl sulfones. A large amount
of PEG reactive ends (800-fold relative to DNA thiols)
were included to capture the majority of DNA mol-
ecules and guarantee the availability of extra vinyl
sulfone moieties in the subsequent polymerization step.

c. Hydrogel polymerization. A fresh stock of 4-arm thiol-
activated PEG (PEG-SH, MW10 kDa, JenKem Tech-
nology) was prepared by resuspending aliquots of
PEG-SH powder at 4% w/v (assuming a PEG density
of 1.1) in water. On ice, 125 µl of PEG-SH stock was
added to the DNA/PEG-VS solution and 239.5 µl of
water to reach a volume of 500 µl. The final gel
contained 2% w/v PEG (1% w/v of each precursor),
had a cross-linking density of 4 mM and harbored 10
µM immobilized ssDNA. The gel precursor remained
liquid for several minutes, during which individual 5 µl
hydrogels were cast either in microtubes or non-treated,
clear flat bottom 96-well plates. The containers were
sealed, and the gels were allowed to polymerize for 1
h at room temperature.

d. Hydrogel washing and swelling. After polymerization,
the gels were washed three times to eliminate unbound
precursors and polymerization buffer; these steps also
allowed the swelling of hydrogels to their equilibrium
volume. Washing steps lasted at least 4 h each, and
were performed in an excess (>30-fold relative to gel precursor volume) of washing buffer (10 mM Tris-HCl,
50 mM NaCl, 10 mM MgCl$_2$, pH 8) at 37° C.

e. In-gel cleavage of ssDNA anchors. Unless mentioned
otherwise, PEG cargo release assays were performed as
follows: 50 nM of Cas12a was mixed with a two-fold
excess of the appropriate guide RNA and 50 nM of
dsDNA trigger or scrambled sequence. The reactions
were assembled in NEBuffer 2.1 (10 mM Tris-HCl, 50
mM NaCl, 10 mM MgCl$_2$, 100 µg/ml BSA. pH 7.9).
For quantitative experiments, a 20-fold volume excess
of reaction mix was used relative to hydrogel pre-
swelling volume; e.g., 100 µl of reaction mix was added
on top of 5 µl gels. All digestions were performed at 37°
C. with periodic shaking (1 s/min). The progression of
ssDNA cutting in the gels was observed on a plate
reader (M5 SpectraMax, Molecular Devices) by con-
tinuously measuring fluorescence accumulation in the
supernatant, caused by the release of the DNA-bound
Cy3 dye. Wavelengths (Ex.554/Em.625) maximizing
the signal-to-noise ratio of the fluorophore were used.
The data was normalized versus complete (100%)
cleavage, defined by measuring fluorescence in a solu-
tion of fluorophore-bound oligonucleotides, diluted so
as to match the expected molarity of anchors in the
buffer+gel system, assuming perfect functionalization
and release. First-order Savitzky-Golay filters were
applied to correct for measurement noise.

Spike-In Experiments in PEG Gels (FIG. 17C)

To test the dynamic response of Cy3-DNA-decorated gels
upon activation of Cas12a, followed the basic gel synthesis
and Cas12a-mediated degradation protocols, with small
variations. Larger gels (20 µl on the sides of 48-well TCPS
plates) overlaid with 250 µl of supernatant were used.
During the experiment, reaction buffer was initially intro-
duced without enzymes or nucleic acids. At time point t=1
h, a concentrated (200×) solution of primed enzyme (10 µM
Cas12a, 15 µM gRNA in 1×NEB 2.1 NEB 2.1 buffer) was
spiked in, and the response of the system was monitored.

Grafting and Release of Horseradish Peroxidase (HRP) on
PEG Gels (FIG. 17D)

3 µl PEG hydrogels were synthesized in microtubes
following the method described above, with smaller final
concentrations of PEG (1.5% w/v, as described below for
FIG. 17G) and DNA (5 µM). In addition to the 5'-thiol
modification, the oligonucleotides harbored a 3'-biotin
modification instead of a fluorophore, which was used to
capture streptavidin-modified HRP. After casting the gels
and washing overnight, any remaining unreacted vinyl
sulfones were blocked by incubating the gels for 4 h at 37°
C. with 20 mM of dithiothreitol freshly dissolved in wash
buffer. The gels (3×1 h) were then in wash buffer, after which
55 µg/ml of streptavidin-conjugated HRP (Pierce) was
added to wash buffer for an overnight (16 h) incubation at
room temperature. The gels were then washed (incubations
of 2 h in wash buffer) until there was no residual HRP
activity in the supernatant. Residual HRP activity was
assessed by diluting wash buffer aliquots 5-fold in a 3,3',5,
5'-tetramethylbenzidine (TMB) substrate solution (Millipore
Sigma) and incubating at 37° C. for 20 min before checking
for the presence of a blue TMB oxidation product.

Digestion of the gels was then done using Cas12a; the
hydrogels were overlaid with 20 µl of pre-warmed reaction
mix (10 nM Cas12a, 20 nM gRNA, 10 nM trigger or
scrambled dsDNA in 1×NEBuffer 2.1) and incubated the
gels at 37° C. with gentle rocking. At each time point, the
supernatant was pipetted out, which was stored at 4° C. until
the end of the experiment. After the last sampling, 10 µl of each supernatant was pipetted into 40 μl of TMB substrate solution dispensed in a 96-well plate, incubated the reaction at 37° C. with shaking for 10 min and blocked the reaction with 50 μl of 1 M H$_2$SO$_4$. Relative enzymatic activity was quantified in the supernatant by measuring absorbance ($\lambda$=450 nm).

When testing for the ability to discriminate between trigger and scrambled sequences, a 100 nM stock of Cas12a, gRNA and dsDNA (1:2:1 molar ratio) was diluted to the appropriate desired concentrations and used 50 μl of supernatant on the DNA-HRP decorated gels, which was incubated for 3 h at 37° C. before testing for enzymatic activity in the supernatant by incubation with TMB substrate and absorbance monitoring at 650 nm.

Input dsDNA Sequence Specificity of Cas12a-Mediated Cleavage in PEG Hydrogels (FIG. 17E)

All the cross-reactivity tests were performed on 5 μl PEG gels (2% w/v) synthesized as described above in a 96-well plate, using the same digestion protocol: all enzymes and dsDNA fragments were introduced at 50 nM with a two-fold molar excess of gRNA, and reactions were monitored by fluorimetry for 12 h.

Measuring PEG-DNA Cutting Kinetics for Various Amounts of dsDNA Input (FIG. 17F)

The experiment was performed as described above, with successive 5-fold dilutions of dsDNA trigger while maintaining constant the molarity of enzyme and guide (50 nM and 100 nM, respectively).

Modulation of Cas12a Activity Through Alterations of PEG Gel Physical Properties (FIG. 17G)

The following changes were made to the general PEG hydrogel synthesis strategy: only half of the usual volume of PEG-VS stock at 4% (w/v) was added for reaction with the reduced DNA; at the end of the grafting reaction, another half-volume of PEG-VS diluted in 1 M triethanolamine (stock concentration: 2, 2.4, 2.8, 3.2, 3.6 and 4%) was added, thereby decreasing the final PEG-VS concentration by up to 25% while maintaining the DNA concentration constant. A full volume of PEG-SH stock diluted accordingly (stock concentrations: 3, 3.2, 3.4, 3.6, 3.8 and 4%, respectively) was then added, and the volume was adjusted with water before casting the gels in a 96-well plate; the resulting hydrogels had concentrations ranging from 1.5 to 2%. The gels were then washed and digested following the usual procedure described above.

Hybridization-Mediated Protection Against Cas12a Cutting in PEG Gels (FIG. 17H)

Protection assays were performed in 1.5% (w/v) PEG gels harboring 2.5 μM of reporter oligonucleotides functionalized on the gel-distal end with 6-carboxyfluorescein (6-FAM). After casting, swelling and washing the DNA-decorated hydrogels, they were incubated in wash buffer supplemented with oligonucleotides complementary to the 6-FAM anchors, or containing an identical amount of non-matching DNA as a control. Three orders of magnitude of anchor to free oligos ratios were tested; for instance, 5 μl hydrogels with 2.5 μM of immobilized reporter DNA were covered with 50 μL of complementary or non-complementary oligonucleotides at 250 nM in buffer solution. Hydrogels were incubated at 37° C. overnight (16 h) with the DNA solutions for hybridization, then washed (3×2 h) with wash buffer without DNA to remove unbound oligonucleotides. Cas12a sensitivity was assayed following the general method outlined above.

Synthesis of NHS-Amine PEG Gels and dsDNA Cis-Cleavage Experiments (S4)

N-hydroxysuccinimide (NHS)-activated 8-arm PEG (40 kDa, NOF Corporation) and amine-activated 8-arm PEG (20 kDa, JenKem) were dissolved at 8% w/v in water. Each pair of oligonucleotides functionalized with 5'-amine groups or 5'-fluorophores (6-FAM and 6-HEX) was pre-hybridized, to a final concentration of 50 μM dsDNA for each duplex. To form double-functionalized hydrogels, the dsDNA probes were first incubated with NHS-PEG: 1 volume of each 50 μM dsDNA solution was added to 4 volumes of 125 mM triethanolamine buffer (pH 7); this solution was mixed with 3 volumes of PEG-NHS stock. The solution was incubated for 15 min at room temperature to graft DNA molecules on the PEG through NHS-amine reactions. Finally, hydrogel polymerization was started by adding one volume of PEG-Amine stock; 10 μL volumes of gel precursor were immediately pipetted into 0.2 ml microtubes and let the reaction complete in the dark at room temperature overnight. To remove buffer and unbound DNA, the gels were pre-incubated at 37° C. in excess of 1×NEBuffer 2.1, washing 3 times over the course of 24 h. At the end of the incubation, the equilibrated supernatant was stored, and the volume of gels was estimated (after swelling) based on their weight and the density of water; the gels were covered with an equivalent volume of equilibrated buffer supplemented with 2 μM Cas12a enzyme and a 4-fold excess of gRNA specific to none or one of the two dsDNA anchors. The reaction was incubated overnight at 37° C., after which the amount of each fluorophore released in the supernatant was estimated by measuring the fluorescence in aliquots (FAM, Ex: 485 nm/Em: 520 nm; HEX, Ex: 530 nm/Em: 560 nm) and comparing to dilution standards.

Synthesis of Carbon Black-DNA Gels (FIGS. 19A-19D)

Aqueous suspensions of carbon black were prepared according to a modified version of the protocol by Parant et al. (18). A stock of 1.5% (w/v) Arabic gum (Sigma, CAS: 9000-01-5) was prepared by dissolving for 2 h in water at 80° C. 8% (w/v) acetylene black particles (>99.9%, Alfa Aesar™, AA3972430) were then added and resuspended by ultrasonication for 15 min (Fisher Scientific FB505 Sonic Dismembrator). Carbon black-DNA hydrogels were prepared according to the protocol described by Xu et al. (22), but 8% (w/v) carbon black suspension was used in place of the reduced graphene oxide. Briefly, the 8% (w/v) carbon black (with 1.5% (w/v) Arabic gum) in a 1:1 ratio was mixed with a solution of 20 mg/ml salmon sperm DNA (Sigma, CAS: 438545-06-3). The mixture was heated to 90° C. with shaking at 1400 rpm for 5 min, before depositing 1-3 μL via pipette onto inkjet-printed, interdigitated silver electrodes (IDEs). After 5 sec (before significant evaporation could occur), the gel-coated electrodes were submerged in liquid nitrogen and lyophilized them for 18-24 h in a benchtop freeze-dryer (Labconco, USA). The flexible interdigitated electrode were fabricated using a silver nanoparticle ink pattern deposited over a polyethylene terephthalate Nano-Benefit 3G Series film (Mitsubishi Imaging MPM Inc., Rye, NY) using a previously reported conductive inkjet printing method (40).

Conductivity Measurements of Carbon Black-DNA Gels (FIGS. 19A-19D)

To estimate the conductivity of the lyophilized carbon black-DNA gels, samples were prepared on inkjet-printed silver electrodes with an adhesive silicone isolator as a mold. The gels were cast with a length of 2.00 mm, width of 2.00 mm, and height above substrate of 1.00 mm such that they spanned a 0.43 mm gap between two printed silver electrodes, and lyophilized the gels in the molds for 24 h. A multimeter (Fluke, USA) was used to measure the resistance reading between the silver electrodes spanned by the gel. Specifically, the two-contact probe method described by Sun et al. (36) was used to calculate the conductivity using the cross-sectional area of the gel and the distance between the probes (Eq. 1), where L is the separation distance (0.43 mm), w is the width (2.00 mm) and t is the height (1.00 mm). By measuring the conductivity of 10 samples, a mean value of 4.2±0.8 mS/cm was obtained:

$$\sigma = \frac{1}{V} \times \frac{L}{wt} \tag{1}$$

In Vitro Reaction of Cas12a with Carbon Black-DNA Gels (FIGS. 19A-19D)

To measure the detachment of lyophilized carbon black-DNA gels from a surface, gels were deposited on flexible, inkjet-printed silver electrodes. After lyophilization of the gels for 18 h, resistance was measured using a multimeter (Model 179, Fluke, USA) and any electrodes with a reading >1 kΩ were excluded as defective before assigning the electrodes to the test groups. Electrodes were then placed individually in the bottom of 1.5 ml Eppendorf tubes and then submerged in 75 μl of the Cas12a reaction mix to ensure the gels were completely covered. The aqueous Cas12a reaction mix contained 1×NEB 2.1 buffer. 0.75 μM Ca12a, 1.3 μM gRNA and varying concentrations of the dsDNA trigger (0.05, 0.1, 0.5 and 1.0 μM). The control reaction mixes contained 1 μM of a scrambled trigger dsDNA sequence and 0 μM dsDNA (Cas12a-gRNA only control). The lyophilized gels were incubated in the Cas12a reaction mixtures at 37° C. for 24 h, with five replicates for each dsDNA trigger concentration (including the control). At 1 h intervals, the Eppendorf tubes were shaken for 10 sec at 800 rpm. After shaking, the silver electrodes were visually inspected, and the complete detachment of any gels from the substrate was recorded. Upon detachment of a gel, the corresponding electrode was removed from the reaction and allowed it to dry. Images of the electrode were recorded with a Leica MZ10 F microscope (brightfield mode, 100 ms exposure, gain=2.0, saturation=1.0) and resistance was measured with a multimeter. At the 24 h time point, all remaining electrodes were removed from the reactions, and recorded images and resistance measurements as above. Finally, the area of the gels remaining on the electrodes was manually quantified (in pixels) relative to the area of the electrode itself using ImageJ version 1.52a.

This experiment was then repeated an additional two times, with the modification that all electrodes were removed from the reaction at a single, set time point (10 h and 21 h, respectively). For the first repeat, dsDNA trigger concentrations of 1.0 and 0.5 μM as well as a 1.0 μM scrambled dsDNA control (n=6 for each condition) were used; after 10 h, the reaction was stopped, the electrodes were dried in air, and resistance was measured using a multimeter (Model 179, Fluke, USA). For the second repeat, dsDNA trigger concentrations of 0.1 and 0.05 μM were used, as well as a 1.0 μM scrambled dsDNA control (n=6 for each condition); after 21 h, the reaction was stopped, the electrodes were dried in air, and resistance was measured.

In Vitro Reaction of Carbon Black-DNA Gels with Mung Bean Nuclease (MBN) (SI)

PET/Ag Electrodes with carbon black-DNA gels were prepared as above and initial resistance measurements taken using a multimeter (Model 179, Fluke, USA). The electrodes were placed in 1.5 ml Eppendorf tubes and submerged in 75

μl of reaction mix. Reactions (n=10 for each condition) were prepared containing 0.2 U/μl MBN (NEB), 0.2 U/μl heat-inactivated MBN (HI MBN), and no MBN all in 1× Mung Bean Nuclease buffer (NEB). The HI MBN was produced by incubating a 1 ml solution of 0.2 U/μl MBN in 1×MBN buffer at 95° C. for 2 h before allowing it to cool to room temperature before the experiment. The lyophilized carbon black-DNA gels were incubated in the reaction mixtures at 30° C. for 2 h, at which point all the electrodes were removed and allowed to dry. Images were recorded of each electrode with a Leica MZ10 F microscope (100 ms exposure, gain=2.0, saturation=1.0) and took resistance measurements with a multimeter.

Synthesis of Acrylamide-DNA Gel Precursors (FIGS. 18A-18E and FIGS. 20A-20E)

Acrylamide-DNA hydrogels were produced using a modified version of a previously described method (37). HPLC-purified single-stranded oligos (Oligo-X and Oligo-Y, described below) functionalized with a methacryl group at their 5'-end (IDT) were resuspended in water to a final concentration of 3 mM. Linker oligos (IDT) without functionalization (L15, described below) were also resuspended in water to a final concentration of 3 mM. A 10× concentrated stock of the reaction buffer from Bio-Rad 50× TAE buffer supplemented with magnesium acetate (125 mM) was prepared such that the final concentrations in the reaction were 1×TAE and 12.5 mM Mg²⁺. Fresh aqueous solutions of 20 v/v % N,N,N',N'-tetramethylethane-1,2-diamine (TE-MED, Millipore Sigma, USA) and 2% (w/v) ammonium persulfate (APS, Millipore Sigma, USA) were prepared before each reaction.

Production of Oligo-Functionalized Acrylamide Polymers Ps-X and Ps-Y (FIGS. 18A-18E and FIGS. 20A-20E)

Separate reactions of between 50-400 μL were prepared for each oligo X and Y in 1.5 mL Eppendorf tubes (final concentration in brackets). Methacryl-functionalized oligos (1 mM), TAE/Mg²⁺ buffer (1×) and 40% acrylamide (4%) were mixed in water at room temperature and vortexed briefly to mix, and the reactions were de-gassed under vacuum for 15 min. APS (0.05% (w/v)) was then added, the tube was inverted to mix, and the contents were collected by spinning down briefly. TEMED (0.5 v/v %) was then added and the mixing repeated. The reactions were allowed to proceed under vacuum at room temperature for 20 min. Incorporation of DNA oligos into the polymer strands was confirmed by agarose gel electrophoresis. To confirm incorporation of ssDNA into the polyacrylamide backbone, the pre- and post-reaction mixtures were run on an agarose gel (FIG. 23A). For this, a 2% agarose gel was prepared containing 1× NorthernMax™-Gly gel running buffer (Invitrogen). For ssDNA methacryl-oligos X and Y (FIG. S34A lanes 3 and 5), samples from the relevant pre-reaction mixes containing 10 pmol of each oligo were brought to 4 μl, mixed with 4 μl of NorthernMax™-Gly gel loading dye, and incubated at 50° C. for 30 min before loading into the gel alongside a low molecular weight DNA ladder (NEB). We took 2 μl samples of the polymerized gel precursors X and Y (4%: FIG. 34B lanes 3 and 4, 7%: FIG. 34B lanes 6 and 7), mixed them with 2 μl of water and 4 μl of Northern-Max™-Gly gel loading dye, and incubated at 50° C. for 30 min before loading into the gel alongside a low molecular weight DNA ladder (NEB). The gel was run for 1.5 h at 80 V 1× NorthernMax™-Gly gel running buffer and imaged under UV light using a G: Box Mini (Syngene USA). Ps-X and Ps-GRNA stocks were stored at 4° C. for up to 2 weeks.

Bulk Degradation of Polyacrylamide-DNA Gels Using FITC-Dextran Microparticles (FIGS. 18A-18E)

10 μL gel mixtures were prepared in 1.5 ml Eppendorf tubes by combining (in order): 4% or 7% Ps-X & -Y (3.00 μl), 10×NEB 2.1 buffer (0.67 μl), 2.5 mg/ml FITC-Dextran (500 kDa, 1.00 μl), Cas12a reaction master mix (1.00 μl), 100 μM trigger or scrambled dsDNA (0.33 μl) and 3 mM linker DNA (L-15, 1.0 μl). The Cas12a master mix was prepared on ice and consisted of NEB LbaCas12a (10 μM) and an MRSA gRNA (15 μM) in 1×NEB 2.1 buffer. The final concentrations of the reagents in the 10 μL gels were as follows: 1.0 μM Cas12a, 1.5 μM MRSA gRNA, 0.25 mg/ml FITC-Dextran, 3.3 UM trigger or scrambled DNA. To enable gelation, the mixtures were incubated at room temperature for 20 min. After gelation, a supernatant consisting of 850 μL of 1×NEB 2.1 buffer was added. The final concentrations of the reagents in the wells were as follows: 11.6 nM Cas12a, 17.4 nM MRSA gRNA, 2.90 μg/ml FITC-Dextran, 38.4 nM trigger or scrambled DNA. The reaction tubes were incubated at 37° C. for 20 h. Every 4 h, the tubes were inverted once, and imaged under UV light (Ex: 385 nm; Em: 525 nm) using a G: Box gel imager (Syngene USA). Results are shown in FIG. 36.

Gold Nanoparticle Synthesis and PEG Functionalization (FIGS. 18A-18E)

Gold NPs (AuNPs) were produced by reducing chloro-auric acid (HAuCl4, Sigma) with sodium citrate (Sigma), following the Turkevich method (39). Briefly, 1 ml of a 6.8 mM sodium citrate solution was added to 50 ml of 0.25 mM gold (III) chloride, while the gold chloride solution was boiling. The samples were stirred and heated for 15 min during which the gold crystals formed. Nanoparticles were left to cool down to room temperature while stirring continued. To functionalize the AuNPs with PEG, 0.33 ml of 2 mM, 5 kDa thiol-terminated poly(ethylene glycol) methyl ether (mPEG, Nanocs, USA) was added to the synthesized AuNPs. AuNP characterization was performed after synthesis by assessing optical absorption. Spectra of the AuNPs was obtained on a Cary 300 UV-Vis (Agilent Technologies, USA). The morphology of the AuNPs was characterized with a FEI Tecnai G2 TEM at 120 kV. ImageJ was used to process the images and measure the dimensions of the AuNPs. Finally, a Zetasizer Nano Zen3600 (Malvern Instruments, UK) was used to measure the hydrodynamic diameter ($D_H$) and the zeta potential ($\zeta$) of the NPs.

Gold Nanoparticle Release from Acrylamide Gels (FIGS. 18A-18E)

9 μl gel mixtures were prepared in PCR tubes by combining (in order): 4% or 7% Ps-X & -Y (3.00 μl), 10×NEB 2.1 buffer (0.67 μl), 5 μM PEG-AuNPs (1.00 μl), Cas12a reaction master mix (1.00 μl), and 100 μM trigger or scrambled dsDNA (0.33 μl). The Cas12a master mix was prepared on ice and consisted of NEB LbaCas12a (10 μM) and an MRSA gRNA (15 μM) in 1×NEB 2.1 buffer. The final concentrations of the reagents in the 10 μl gels were as follows: 1.0 μM Cas12a, 1.5 μM MRSA gRNA, 0.5 μM PEG-AuNPs, and 3.3 μM trigger or scrambled DNA. Press-to-Seal™ silicone isolators (round, 2.0 mm diameter, 1.7 mm depth, ThermoFisher Scientific, USA) were cut into single units and attached to the center of the bottom of individual wells in a 24-well tissue culture plate. The 9 μl gel mixtures were pipetted into the silicone isolators, and 3 mM linker DNA (L-15, 1.0 μl) was then added. The mixtures were stirred briefly with a pipette tip and then incubated at room temperature for 20 min. After gelation, a supernatant was added consisting of 850 μL of 1×NEB 2.1 buffer to each well. The final concentrations of the reagents in the wells were as follows: 11.6 nM Cas12a, 17.4 nM MRSA gRNA, 5.81 nM PEG-AuNPs, 38.4 nM trigger or scrambled DNA.

We then transferred the 24-well plate to a plate reader and recorded absorbance readings (520 nm) from the center of the 24-well plate (i.e. through the gel itself, FIGS. 25A-25B) every 2 min for 15 h at 37° C.; data were smoothened with a first-order Savitzky-Golay filter. At the 15 h timepoint, we removed the 24-well plate and took a 200 μl sample of the supernatant from each reaction and transferred them to a 96-well plate. To calculate the final % release of AuNPs, we measured the A520 nm of the supernatant and compared it to a 100% release standard containing 5.81 nM PEG-AuNPs.

Preparation of Polyacrylamide-DNA Gels for Bulk Degradation Using EVAGREEN® and Cell Release (FIGS. 18A-18E)

A pre-gel stock was prepared with a 1:1:0.6 ratio of Ps-X, Ps-Y and 10 μM bridge and incubated to cross-link for 10 min. An Amicon 10 kDa spin filter was used to centrifuge and resuspend the pre-gel stock to remove free acrylamide monomers. Washing and spin filtering were performed two additional times prior to EVAGREEN® bulk degradation or cell release. A nanodrop was used to normalize the concentration of the final pre-gel stock mix to 1.8 mg/ml of ssDNA.

Gelation of Polyacrylamide (PA)-DNA with EVAGREEN® for Bulk Hydrogel Degradation (FIGS. 18A-18E)

150 μl gel mixtures were prepared by combining 100 μl of the pre-gel stock mix at 1.8 mg/ml ssDNA with 5 μl of 3 mM bridge, 15 μl of 10×NEB 2.1 solution, 7.5 μl of 20× EVAGREEN® and 22.5 μl of PBS. The mixture was kept at 37° C. to minimize cross-linking while the gels were spotted on a 384-well plate. The 1 μl gels were dropped at the bottom of the 384-well plate and allowed to cross-link for 20 min. For gel-degradation experiments, 20 μl of a solution containing 1 μM Cas12a, 1.5 μM gRNA and dsDNA trigger (5 μM, 2 μM, 1 UM, 0.2 μl) was added on top of the PA-DNA hydrogels, and EVAGREEN® fluorescence was recorded on a Synergy Neo at 37° C. (Ex: 490 nm, Em: 535 nm).

Primary Cells for DNA-Polyacrylamide Gel Release (FIGS. 18A-18E)

Cell release experiments were performed using primary peripheral blood mononuclear cells (PBMCs). Mobilized peripheral blood and leukapheresis product were anonymously collected from donors undergoing stem cell mobilization at the Massachusetts General Hospital (MGH) under Institutional Review Board approved protocol #2015P001859. The mononuclear cells were purified via Histopaque 1077 gradient (Sigma, 10771). PBMCs were expanded in RPMI 1640+GlutaMAX™ Medium (Thermo Fisher Scientific, Waltham, MA) supplemented with 10% fetal bovine serum and 2 ng/ml recombinant IL-2. The cell suspension was prepared by spinning down the cell culture at 300 g for 5 min and resuspending cells at $10^7$ cells/ml.

Gelation of Polyacrylamide (PA)-DNA with Encapsulated Cells (FIGS. 18A-18E, FIG. 40 and FIGS. 41A-41C)

30 μl of washed pre-gel stock was combined with 30 μl of cell-bridge mixture containing 270 μM bridge, 30 μM fluorescently labeled bridge, $2 \times 10^6$ cells and 30 mM $MgCl_2$ in 1×PBS. The solution was mixed until gelling appeared homogeneous and the pipette flow became highly viscous. Hydrogel droplets (2 μl) were deposited at the center of each well in a sterile 96-well plate with flat clear bottom, and incubated at 37° C. for 2 min. After droplet incubation, 100 μl of RPMI was added with 10% FBS (R10) or OMEM media with 10% FBS and 10 mM $MgCl_2$ (O10+MgCl2) with Cas degradation reagents gently from the side of the well to avoid pressure driven hydrogel dislodgement. In the representative cell-encapsulation image of FIG. 18E, PBMCs were pre-stained before encapsulation to allow for in-gel visualization using calcein blue-AM (live, blue color) and ethidium homodimer-1 (dead, red color). In other experiments, such as the ones presented in FIG. 40, PBMCs were not pre-stained to allow for cell viability assessment after gel degradation and release.

Cell Release from DNA-Polyacrylamide Gel and Viability Analysis (FIGS. 18A-18E, FIG. 40 and FIGS. 41A-41C)

The hydrogels were incubated with encapsulated PMBCs at 37° C. with 100 µl Cas12a solutions containing 0.5 µM Cas12a, 1 µM gRNA, 0.1×NEB buffer 2.1, scrambled dsDNA at 5 µM, or trigger dsDNA at 5 µM. 1 µM, and 0.2 µM. Negative controls contained RPMI media with 10% FBS, as well as OMEM media with 10% FBS and 10 mM MgCl$_2$. Gel degradation started upon addition of the Cas solution, and hydrogels were monitored to assess degradation kinetics (FIG. 18E and FIG. 40).

After Cas-mediated hydrogel degradation and PBMC release, cell viability was assessed using ethidium homodimer-1 (Invitrogen) and calcein blue-AM (FIG. 41A-41C). This was performed on replicates of the experiments where the cells had not been pre-stained for imaging purposes.

The cell-encapsulation and cell-release imaging was performed using an EVOS® FL digital inverted imaging system with four-color fluorescence and transmitted-light capabilities. Images of PA-DNA hydrogel macroscopic morphology were acquired before and after Cas degradation using an EVOS® FL digital inverted microscope set for GFP fluorescence (excitation=470 nm, emission=525 nm) using a 4× magnification objective, 30% LED illumination intensity and 50% contrast. After gel degradation we acquired images of released PBMCs from PA-DNA hydrogels using an EVOS® FL digital inverted microscope with a 20× objective. Imaging of live cells was performed using DAPI mode (excitation=360 nm, emission=447 nm) with 40% LED illumination intensity and 90% contrast. Dead cells were imaged using the RFP mode (excitation=530 nm, emission=593 nm) with 50% LED illumination intensity and 90% contrast. GFP channel was also acquired at this magnification to assess degraded gel bulk. Live, dead and degraded gel bulk images were merged using the EVOS® FL color overlay mode. Representative images of this process are shown in FIG. 20E, FIG. 41, and FIGS. 42A-42B.

Cell Viability in Cas12a Reaction Conditions (FIG. 42)

Viability was assessed after 24 h incubation at 37° C. by staining cells with calcein-AM and ethidium homodimer-1 (Invitrogen, Eugene, Oregon). Cells were incubated in the following conditions: R10 media (RPMI with 10% FBS), O10 test media containing OMEM media, 10% FBS and 10 mM MgCl$_2$, and O10 test media with 0.5 µM Cas12a. 1 µM gRNA, 0.1×NEBuffer 2.1 and 1 µM scrambled or trigger dsDNA.

Fabrication of CRISPR-Gel µPad Stop-Flow System with Electrical Readout (FIGS. 20A-20E)

Paper µPADs were fabricated according to a modified version of the protocol published by Wei, X. et al. (29), using a double-sided wax printing pattern. Top and bottom µPAD wax layers were designed using Illustrator CC v23.0.4 (Adobe Inc. San Jose, CA) and printed on Whatman® Grade 1 chromatographic filter paper (Thermo Fisher Scientific, Waltham, MA) using a Xerox Phaser 8560 printer. Printed µPAD sheets were wax reflowed through hot pressing for 15 sec at 125° C. using a Cricut EasyPress™ (Cricut Inc., Fork, UT), and then cooled to room temperature. Individual µPADs were cut and folded as shown in FIGS. 20A-20E, and alignment of hydrophilic sections was confirmed using a light source and visual inspection. Any µPADs with visible printing, reflowing or alignment defects were discarded. After baking and folding, layers 1 to 4 of the µPADs were ensured to exhibit circular hydrophilic paper regions for vertical flow of approximately 1.5 mm in diameter, surrounded by an evenly distributed hydrophobic wax coating to prevent undesired lateral flow. Layer 5 of the µPADs contains a 1.5×30 mm lateral flow channel with marked lengths. To prepare functional µPADs, first, layer 3 was filled with 0.5 µl of oligo-functionalized acrylamide polymer solution containing both Ps-X and Ps-Y (1:1). Layer 4 was then filled with PBS buffer containing food color dye (0.5 µl, 1:5 red dye/PBS). Paper µPADs were then freeze dried with deposited reagents in layers 3 and 4 before continuing assembly. To perform conductivity measurements, Layer 5 of the µPADs was covered with 3×30 mm strips of 87580-Nickel/Copper Conductive Fabric Tape (Laird Technologies EMI, Pall Mall, London) placed along the top and bottom sides of the lateral flow channel to act as parallel conductive planes to measure channel electrical resistance as a function of buffer wicking distance. Both the conductive tape and wiring for connection over layer 5 were laminated using plastic tape to prevent detachment. Layer 1 and layer 2 of the µPADs were left uncovered to receive the conductive buffer and DNA linker during testing.

Flow and Conductivity Measurements in u Pad (FIGS. 20A-20E, FIGS. 44A-44B, and FIG. 46)

At the time of testing, layer 2 of the µPADs was filled with 0.3 µl of ssDNA linker (100 µM) that had been pre-incubated for 4 h at 37° C. in a cutting solution containing 300 nM Cas12a, 1 µM MRSA gRNA, and dsDNA MRSA Trigger (at concentrations 0 nM, 0.4 nM, 2 nM, 10 nM, 50 nM) in 1×NEB Buffer 2.1. Negative control reactions were performed with scrambled MRSA dsDNA. After the pre-digested ssDNA bridge solution had been deposited and air dried for 1 min, the µPAD was collapsed to fluidically connect all hydrophilic regions with layer 1 acting as a protective cover for all other layers and as the inlet for running PBS buffer. MRSA µPAD experiments were conducted using 10 µl of running PBS buffer, while EBOV µPAD experiments were done using 2 µL running PBS buffer. µPAD channel resistance was continuously monitored using a 34411A Digital Multimeter (Keysight Technologies Inc., Santa Rosa, CA) for dynamic measurements (FIGS. 20A-20E), and endpoint values were taken at 5 min for determining the sensitivity curve (FIGS. 20A-20E). Testing of flow and conductivity measurements were performed in the µPad in triplicate. Representative samples of paper µPAD regions with visible polyacrylamide-DNA gelation due to the presence of uncut DNA linker were imaged using a scanning electron microscope (SEM) and compared to un-gelled regions where cut ssDNA linker was present.

Positive controls were performed to validate enzyme activity during Cas12a-mediated cleavage of the polyacrylamide gel linker in reactions that contained 300 nM Cas12a, 1 µM MRSA gRNA, and increasing concentrations of dsDNA MRSA Trigger (0 nM, 0.4 nM, 2 nM, 10 nM, 50 nM) and NEB Buffer 2.1 (1×), as well as 750 nM ssDNA quenched fluorescently labeled reporter. Fluorescence readings were used as a proxy to confirm the activity of Cas12a in the pre-incubation reaction (FIG. 45).

RFID integration in CRISPR-mediated stop-flow µPad (FIGS. 20A-20E)

To construct the CRISPR-active RFID sensor, a 10×70 mm flexible WRL-14147 ultrahigh-frequency (UHF) RFID tag (SparkFun Electronics Inc., Niwot, CO) was modified with a flexible interdigitated electrode capable of short-circuiting an inner loop of the tag antenna in the presence of conductive buffer at a specific vertical layer or lateral flow distance of the previously described μPAD. The flexible interdigitated electrode was fabricated using a silver nanoparticle ink pattern (FIG. 20D) and deposited over a polyethylene terephthalate NanoBenefit 3G Series film (Mitsubishi Imaging MPM Inc., Rye, NY) using a previously reported conductive inkjet printing method (40). Both electrode terminals were connected to the first loop regions at this specific RFID tag antenna, which is located in close proximity to the UHF-RFID chip (see FIG. 20D). For the MRSA μPAD RFID measurements (FIGS. 48A-48D) a modified four-layer μPAD stack (without layer 5) was assembled on top of the RFID device as a flow-through arrangement, aligning the bottom of the hydrophilic region in layer 4 to be in contact with the interdigitated electrode. For the EBOV μPAD RFID measurements (FIGS. 20D-20E), a modified five-layer μPAD was prepared by aligning entry of the lateral flow hydrophilic channel of layer 5 to be in direct contact with the interdigitated electrode. Reagent placement and activation were performed as with the μPAD flow and conductivity measurements previously described. The relative received signal strength (RSSI) of each μPAD RFID tag was measured in the presence or absence of target DNA after incubation in the cutting solution containing Cas12a, gRNA, and linker DNA. Reduction in absolute RSSI values indicates that the power level of the received radio signal has decreased due to conductive buffer flow and RFID tag antenna short-circuiting. As initial proof-of-concept of this effect in the MRSA μPAD RFID arrangement, the RSSI was measured for two independent tags (one modified and one unmodified) both placed at a distance of 0.5 m from a WRL-14131 UHF-RFID TNC antenna (SparkFun Electronics Inc., Niwot, CO) connected to a M6E-NANO simultaneous RFID tag reader (SRTR) (ThingMagic Inc. Bedford, MA) and an Arduino Uno microcontroller (Arduino LLC, Somerville, MA) using the M6E-NANO RFID Arduino library. Result of this single replicate experiment is shown in FIG. 48D.

Ebola Diagnostic and EBOV RT-RPA CRISPR μPAD (FIGS. 20A-20E)

To demonstrate applicability of the CRISPR μPAD RFID mode of sensing, a sensitive Ebola virus RT-RPA CRISPR μPAD was developed. To achieve this, a dsDNA fragment encoding for Zaire strain Ebola virus VP30 protein was obtained from IDT, which was then amplified by PCR and transcribed in vitro using HighScribe Quick (NEB). Serial dilutions of the RNA by RT-RPA were tested followed by Cas12a detection. Superscript (Invitrogen) was used for the RT step using EBOV-R primer, following manufacturer's instructions. Then, 5 μl of the reverse-transcribed RNA was added to 50 μl of RPA basic (TwistDx) lyophilized reactions that contained 480 μM of each RPA primer and 14 mM magnesium acetate, as per manufacturer's instructions. The RPA reaction was incubated for 40 min at 37° C. After amplification, the ssDNA linker, gRNA and Cas12a were added to final concentrations of 300 μM, 0.9 μM and 0.5 μM, respectively. The samples were incubated for 4 h, and then diluted 1:1 with nuclease-free water (all called RT-RPA/linker mix) and tested in the μPADs.

To assemble the μPAD, 0.3 μl of RT-RPA/linker mix was deposited in layer 2, 0.3 μl of 4% Ps-XY was deposited in layer 3 and 0.3 μl 1×PBS with red dye was deposited in layer 4. Lateral flow region in layer 5 was placed in contact with the interdigitated electrode of the modified RFID tag starting at 2 mm from channel entry. Reagents were air dried for 2 minutes and μPAD was collapsed to allow for contact of hydrophilic sections. Running 1×PBS buffer (2 μL) was added to the Layer 1 (top) of the μPAD to start readings. Colorimetric readings of the EBOV RT-RPA CRISPR μPAD detection system were obtained at increasing concentrations of input EBOV RNA trigger (0 aM, 2 aM, 11 aM, 53 aM, 255 aM, 1.4 fM, 6.8 fM, 34.1 fM, 170 fM, 853 fM, 4.2 nM and 21 nM) and are shown in FIG. 20C as verification of the system performance. A representative assembly schematic of the RFID fuse version of the EBOV RT-RPA CRISPR μPAD is shown in FIG. 20D. In solution readouts from analogous RPA reactions for comparison with the μPAD system, final concentrations of 50 nM Cas12a: 62.5 nM gRNA: 750 nM FQ reporter in NEB 2.1 buffer to 50 μl of RPA reactions (FIGS. 34A-34C) were prepared. These verification reactions (3 μl, 384-well microplate) were then incubated at 37° C. for 2 h and fluorescence was recorded in a fluorescence plate reader (Biotek NEO HTS) (Ex: 485 nm; Em: 535 nm).

RFID readings of EBOV RT-RPA CRISPR μPAD (FIGS. 20A-20E)

The detection of an RFID signal change from the EBOV RT-RPA CRISPR-active μPADs is caused by conductive buffer flow through layer 5, which is located in contact with the inkjet-printed interdigitated electrodes that are in turn connected to the first antenna loop of the RFID tags. The received signal strength indicator (RSSI) was measured in the testing RFID μPAD in combination with an attached unmodified reference tag using an ultra-high frequency (UHF) RFID antenna positioned around 0.5 m from RFID μPAD arrangement (FIG. 20D). A rapid increase in absolute RSSI difference between testing and reference RFID tags indicates conductive buffer flow through the μPAD and presence of EBOV RNA in the sample.

An experimenter blinded multi-center evaluation (n=12, 6 positive and 6 blank) of the fuse-like behavior of the EBOV RT-RPA CRISPR RFID μPAD is shown in FIG. 20E and FIG. 49. Samples contained either 0 aM (−) or 11 aM (+) of EBOV RNA trigger previously amplified via RT-RPA and incubated in Cas solution for 4 hr were run in this specific CRISPR μPAD RFID assembly. Activation results are shown in FIG. 20E and FIG. 49.

DNA and RNA Sequences

For this study, all DNA oligonucleotides were obtained from Integrated DNA Technologies. Cas12a gRNAs were produced by in vitro transcription using an HiScribe T7 transcription kit (NEB) and oligonucleotide templates; gRNAs were subsequently purified using an RNA Clean & Concentrator kit (Zymo Research). The sequences used are provided in TABLE 4.

TABLE 4

DNA and RNA sequences used in this study.

| Name | Sequence (5' to 3') | SEQ ID NO: | Modifications | Notes |
|---|---|---|---|---|
| mecA gRNA | GGGUAAUUUCUACU AAGUGUAGAUUUAA AGAAGAUGGUAUGU GG | 1 | N/A | Cas12a guide RNA targeting a fragment of mecA gene. Synthesized by in vitro T7 transcription. Also referred to as "MRSA1 gRNA" in the SI |
| mecA dsDNA trigger | TTTAATTTTGTTAAAG AAGATGGTATGTGGA AGTTAGATT | 2 | N/A | Trigger sequence for Cas12a primed with mecA gRNA. Double stranded |
| Scrambled dsDNA trigger | TAGTAGTGATTATGT TAGATAGTGAATAGG TTTAATGTAT | 3 | N/A | Obtained by random permutation of the mecA trigger sequence. Double stranded |
| mecA-1 mismatch | TTTAATTTTGTTAAAG AAGATGTTATGTGGA AGTTAGATT | 4 | N/A | Single substitution variant of mecA |
| mecA-3 mismatches | TTTAATTTTGTTAAAT AAGATGTTATGTAGA AGTTAGATT | 5 | N/A | Triple substitution variant of mecA |
| Fluorophore-quencher reporter | TTATT | — | 5'-6FAM, 3'-IowaBlackFQ | Generates a fluorescent signal when cleaved; used for Cas12a activation assays in solution |
| Acrydite oligo X | TTATTCTTGTCTCCCG AGAT | 12 | 5' Acrydite | Acrylamide-DNA gels |
| Acrydite oligo Y | TTATTTCACAGATGA GTATC | 13 | 5' Acrydite | Acrylamide-DNA gels |
| Linker-15 | GATACTCATCTGTGA TTATTTTATTTTATTA TCTCGGGAGACAAG | 16 | N/A | Acrylamide-DNA gels, cross-linker |
| Linker-15-F | TGATACTCATCTGTG ATTATTTTATTTTATT ATCTCGGGAGACAAG | 16 | 5'-6FAM | Fluorescent acrylamide-DNA gels, cross-linker |
| PEG gel reporter | TTATTATTACTATCTA TTATCATTATCATT | 20 | 5'-C6-thiol 3'-Cy3 | PEG-DNA gels main model molecule, used in most PEG-based experiments |
| PEG gel reporter A | TTTACACAAGCACTA CGTACACTACCACAT | 21 | 5'-DTPA, 3'-6FAM | PEG-DNA gels, anneals with Protector sequence A' |
| Protector sequence A | ATGTGGTAGTGTACG TAGTGCTTGTGTAAA | 22 | N/A | PEG-DNA gels, anneals with PEG gel reporter A |
| PEG gel reporter B | TTTTTATTTATCTATC TGACGA | 23 | 5'-C6-thiol 3'-Cy3 | PEG-DNA gels, anneals with Protector sequence B' |
| Protector sequence B | TCGTCAGATAGATAA ATAAAAA | 24 | N/A | PEG-DNA gels, anneals with PEG gel reporter B |
| Biotin anchor | TTATTATTACTATCTA TTATCATTATCATT | 25 | 5'-C6-thiol, 3'-biotin | PEG-DNA gels |
| ermA gRNA | GGGUAAUUUCUACU AAGUGUAGAUCUAU UAAUGGUGGAGAUG GA | 26 | N/A | Cas12a guide RNA targeting a fragment of ermA gene. Synthesized by in vitro T7 transcription |
| ermC gRNA | GGGUAAUUUCUACU AAGUGUAGAUAAUC GUCAAUUCCUGCAUG U | 27 | N/A | Cas12a guide RNA targeting a fragment of vermC gene. Synthesized by in vitro T7 transcription |

TABLE 4-continued

DNA and RNA sequences used in this study.

| Name | Sequence (5' to 3') | SEQ ID NO: | Modifications | Notes |
|---|---|---|---|---|
| spa gRNA | GGGUAAUUUCUACU AAGUGUAGAUUGGU AAUGCUUGAGCUUU GU | 28 | N/A | Cas12a guide RNA targeting a fragment of spa gene. Synthesized by in vitro T7 transcription |
| vanA gRNA | GGGUAAUUUCUACU AAGUGUAGAUGUAU UCAUCAGGAAGUCG AG | 29 | N/A | Cas12a guide RNA targeting a fragment of vanA gene. Synthesized by in vitro T7 transcription |
| ermA-dsDNA trigger | GCTTTGGGTTTACTAT TAATGGTGGAGATGG ATATAAAAA | 30 | N/A | Trigger sequence for Cas12a primed with ermA gRNA. Double stranded |
| ermC dsDNA trigger | TAATATTGTTTAAATC GTCAATTCCTGCATG TTTTAAGGA | 31 | N/A | Trigger sequence for Cas12a primed with ermC gRNA. Double stranded |
| spa dsDNA trigger | TTCACCAGTTTCTGGT AATGCTTGAGCTTTG TTAGCATCT | 32 | N/A | Trigger sequence for Cas12a primed with spa gRNA. Double stranded |
| vanA dsDNA trigger | ACGGAATCTTTCGTA TTCATCAGGAAGTCG AGCCGGAAAA | 33 | N/A | Trigger sequence for Cas12a primed with vanA gRNA. Double stranded |
| ZEBOV gblock | GTGCGCGTTCCTACT GTATTTCATAAGAAG AGAGTTGAACCATTA ACAGTTCCTCCAGCA CCTAAAGACATATGT CCGACCTTGAAAAAA GGATTTTTGTGTGAC AGTAGTTTTTGCAAA AAAGACCACCAGTTA GAAAGTTTAACTGAT AGGGAATTACTCCTA CTAATCGCCCGTAAG ACTTGTGGATCAGTA GAACAACAATTAAAT ATAACTGCACCCAAG GACTCG | 34 | N/A | Fragment of the VP30 gene of Zaire ebolavirus; ordered as a dsDNA gene fragment |
| ZEBOV RPA-1 | CTACTGTATTTCATAA GAAGAGAGTTGAACC | 35 | N/A | RPA forward primer-Ebola |
| ZEBOV RPA-2 | AATTGTTGTTCTACTG ATCCACAAGTCTTAC | 36 | N/A | RPA reverse primer-Ebola |
| ZEBOV-T7 | GCGCTAATACGACTC ACTATAGGGTGCGCG TTCCTACTGTATT | 37 | N/A | PCR primer for the ZEBOV gblock, with T7 for in vitro transcription |
| qPCR-ZEBOV-F | GTGCGCGTTCCTACT GTATT | 38 | N/A | qPCR primer Ebola |
| qPCRT-ZEBOV-R | GAGTCCTTGGGTGCA GTTATATT | 39 | N/A | qPCR reverse primer Ebola. Also used as RT reverse primer |
| ZEBOV gRNA | GGGTAATTTCTACTA AGTGTAGATGGTGCT GGAGGAACTGTTAA | 40 | N/A | Cas12a guide RNA targeting a fragment of Zaire ebolavirus VP30 gene. Synthesized by in vitro T7 transcription |
| MRSA2 gRNA | GGGUAAUUUCUACU AAGUGUAGAUAUUU UGUUAAAGAAGAUG GU | 41 | N/A | Alternative Cas12a guide RNA targeting a fragment of mecA gene. |
| MRSA3 gRNA | GGGUAAUUUCUACU AAGUGUAGAUACAA AAUUAAAUUGAACG UU | 42 | N/A | Alternative Cas12a guide RNA targeting a fragment of mecA gene. |

TABLE 4-continued

DNA and RNA sequences used in this study.

| Name | Sequence (5' to 3') | SEQ ID NO: | Modifications | Notes |
|---|---|---|---|---|
| MRSA2 trigger | ATTTTGTTAAAGAAG ATGGT | 43 | N/A | Trigger sequence for Cas12a primed with MRSA2 gRNA. Double stranded |
| MRSA3 trigger | ACAAAATTAAATTGA ACGTT | 44 | N/A | Trigger sequence for Cas12a primed with MRSA3 gRNA. Double stranded |
| Control gRNA for dsDNA targeted cutting | GGGUAAUUUCUACU AAGUGUAGAUGUAU GGCUUCAUUCAGCUC C | 45 | N/A | Cas12a guide RNA targeting a fragment of the ampR gene. Synthesized by in vitro T7 transcription |
| dsDNA release probe X | TTTAATTTTGTTAAAG AAGATGGTATGTGGA CGTATGGAATAAGTG | 8 | 5'-C6-amine | Hybridizes with dsDNA probe X'; contains a mecA sequence for dsDNA recognition and cutting |
| dsDNA release probe X' | TCACTTATTCCATACG TCCACATACCATCTTC TTTAACAAAATTAA | 9 | 5'-6FAM | Hybridizes with dsDNA probe X; contains a mecA sequence for dsDNA recognition and cutting |
| dsDNA release probe Y | TTATTATTTACAACGT CGTGACTGGGAAAAC CCTTGGAATAAGTG | 10 | 5'-C6-amine | Hybridizes with dsDNA probe Y' |
| dsDNA release probe Y' | TCACTTATTCCAAGG GTTTTCCCAGTCACG ACGTTGTAAATAATA | 11 | 5'-HEX | Hybridizes with dsDNA probe Y |
| Control gRNA for cutting | GGGUAAUUUCUACU AAGUGUAGAUGUAU GGCUUCAUUCAGCUC C | 46 | N/A | Cas12a guide RNA targeting a fragment of the ampR gene. Synthesized by in vitro T7 transcription |

REFERENCES

1. S. Y. Li et al., CRISPR-Cas12a has both cis- and trans-cleavage activities on single stranded DNA. Cell Research 28, 491-493 (2018).
2. J. S. Chen et al., CRISPR-Cas12a target binding unleashes indiscriminate single-stranded DNase activity. Science 360, 436-439 (2018).
3. G. J. Knott, J. A. Doudna, CRISPR-Cas guides the future of genetic engineering. Science 361, 866-869 (2018).
4. J. S. Gootenberg et al., Nucleic acid detection with CRISPR-Cas13a/C2c2. Science 356, 438-442 (2017).
5. J. S. Gootenberg et al., Multiplexed and portable nucleic acid detection platform with Cas13, Cas12a, and Csm6. Science 360, 439-444 (2018).
6. N. Glorevski et al., Designer matrices for intestinal stem cell and organoid culture. Nature 539, 560-564 (2016).
7. W. Na, D. Nam, H. Lee, S. Shin, Rapid molecular diagnosis of infectious viruses in microfluidics using DNA hydrogel formation. Biosensors & Bioelectronics 108, 9-13 (2018).
8. M. Qin et al., Bioinspired Hydrogel Interferometer for Adaptive Coloration and Chemical Sensing. Advanced Materials 30, (2018).
9. J. S. Kahn et al., Integration of Switchable DNA-Based Hydrogels with Surfaces by the Hybridization Chain Reaction. Nano Letters 15, 7773-7778 (2015).
10. E. Heitzer, P. Ulz, J. B. Geigl, Circulating Tumor DNA as a Liquid Biopsy for Cancer. Clinical Chemistry 61, 112-123 (2015).
11. H. H. Yang, H. P. Liu, H. Z. Kang, W. H. Tan, Engineering target-responsive hydrogels based on aptamer-target interactions. Journal of the American Chemical Society 130, 6320-6321 (2008).
12. A. Cangialosi et al., DNA sequence-directed shape change of photopatterned hydrogels via high-degree swelling. Science 357, 1126-1129 (2017).
13. B. P. Kleinstiver et al., Genome-wide specificities of CRISPR-Cas Cpf1 nucleases in human cells. Nature Biotechnology 34, 869-+ (2016).
14. J. Y. Li, D. J. Mooney, Designing hydrogels for controlled drug delivery. Nature Reviews Materials 1, 16071 (2016).
15. A. M. Rosales, K. S. Anseth, The design of reversible hydrogels to capture extracellular matrix dynamics. Nature Reviews Materials 1, 15012 (2016).
16. B. P. Purcell et al., Injectable and bioresponsive hydrogels for on-demand matrix metalloproteinase inhibition. Nature Materials 13, 653-661 (2014).
17. M. M. Martino et al., Growth Factors Engineered for Super-Affinity to the Extracellular Matrix Enhance Tissue Healing. Science 343, 885-888 (2014).
18. H. Parant et al., Flowing suspensions of carbon black with high electronic conductivity for flow applications:

Comparison between carbons black and exhibition of specific aggregation of carbon particles. Carbon 119, 10-20 (2017).

19. M. Pawlyta, J. N. Rouzaud, S. Duber, Raman microspectroscopy characterization of carbon blacks: Spectral analysis and structural information. Carbon 84, 479-490 (2015).

20. M. Spahr, R. Gilardi, D. Bonacchi., "Carbon black for electrically conductive polymer applications" in Fillers for Polymer Applications, R. Rothon, Ed. (Springer, Berlin, Heidelberg, Polymers and Polymeric Composites: A Reference Series, 2016).

21. C. H. Lu, H. H. Yang, C. L. Zhu, X. Chen, G. N. Chen, A Graphene Platform for Sensing Biomolecules. Angewandte Chemie-International Edition 48, 4785-4787 (2009).

22. Y. X. Xu, K. X. Sheng, C. Li, G. Q. Shi, Self-Assembled Graphene Hydrogel via a One-Step Hydrothermal Process. Acs Nano 4, 4324-4330 (2010).

23. B. W. Liu, S. Salgado, V. Maheshwari, J. W. Liu, DNA adsorbed on graphene and graphene oxide: Fundamental interactions, desorption and applications. Current Opinion in Colloid & Interface Science 26, 41-49 (2016).

24. S. Manohar et al., Peeling Single-Stranded DNA from Graphite Surface to Determine Oligonucleotide Binding Energy by Force Spectroscopy. Nano Letters 8, 4365-4372 (2008).

25. Y. X. Xu, Q. O. Wu, Y. Q. Sun, H. Bai, G. Q. Shi, Three-Dimensional Self-Assembly of Graphene Oxide and DNA into Multifunctional Hydrogels. Acs Nano 4, 7358-7362 (2010).

26. K. Pardee et al., Rapid, Low-Cost Detection of Zika Virus Using Programmable Biomolecular Components. Cell 165, 1255-1266 (2016).

27. K. Pardee et al., Paper-Based Synthetic Gene Networks. Cell 159, 940-954 (2014).

28. Y. He, Y. Wu, J. Z. Fu, W. B. Wu, Fabrication of paper-based microfluidic analysis devices: a review. Rsc Advances 5, 78109-78127 (2015).

29 X. F. Wei et al., Target-Responsive DNA Hydrogel Mediated "Stop-Flow" Microfluidic Paper-Based Analytic Device for Rapid, Portable and Visual Detection of Multiple Targets. Analytical Chemistry 87, 4275-4282 (2015).

30. A. K. Badu-Tawiah et al., Polymerization-based signal amplification for paper-based immunoassays. Lab on a Chip 15, 655-659 (2015).

31. E. Fu, B. Lutz, P. Kauffman, P. Yager, Controlled reagent transport in disposable 2D paper networks. Lab on a Chip 10, 918-920 (2010).

32. S. B. Stephan et al., Biopolymer implants enhance the efficacy of adoptive T-cell therapy. Nature Biotechnology 33, 97-U277 (2015).

33. A. S. Mao et al., Deterministic encapsulation of single cells in thin tunable microgels for niche modelling and therapeutic delivery. Nature Materials 16, 236-243 (2017).

34. H. Parant et al., Flowing suspensions of carbon black with high electronic conductivity for flow applications: Comparison between carbons black and exhibition of specific aggregation of carbon particles. Carbon 119, 10-20 (2017).

35. Y. X. Xu, K. X. Sheng, C. Li, G. Q. Shi, Self-Assembled Graphene Hydrogel via a One-Step Hydrothermal Process. Acs Nano 4, 4324-4330 (2010).

36. L. Sun, S. S. Park, D. Sheberla, M. Dinca, Measuring and Reporting Electrical Conductivity in Metal Organic Frameworks: Cd-2 (TTFTB) as a Case Study. Journal of the American Chemical Society 138, 14772-14782 (2016).

37. M. L. Previtera, N. A. Langrana, Preparation of DNA-crosslinked Polyacrylamide Hydrogels. Jove-Journal of Visualized Experiments, (2014).

38. J. Turkevich, P. C. Stevenson, J. Hillier, A study of the nucleation and growth processes in the synthesis of colloidal gold. Discussions of the Faraday Society, 55-& (1951).

39. X. F. Wei et al., Target-Responsive DNA Hydrogel Mediated "Stop-Flow" Microfluidic Paper-Based Analytic Device for Rapid, Portable and Visual Detection of Multiple Targets. Analytical Chemistry 87, 4275-4282 (2015).

40. H. H. Lee, K. S. Chou, K. C. Huang, Inkjet printing of nanosized silver colloids. Nanotechnology 16, 2436-2441 (2005).

41. S. Sugimoto et al., Broad impact of extracellular DNA on biofilm formation by clinically isolated Methicillin-resistant and -sensitive strains of Staphylococcus aureus. Scientific Reports 8, 2254 (2018).

42 M. Arthur, C. Molinas, C. Mabilat, P. Courvalin, Detection of erythromycin resistance by the polymerase-chain reaction using primers in conserved regions of erm ribosomal-RNA methylase genes. Antimicrobial Agents and Chemotherapy 34, 2024-2026 (1990).

43. B. Strommenger, C. Kettlitz, G. Werner, W. Witte, Multiplex PCR assay for simultaneous detection of nine clinically relevant antibiotic resistance genes in Staphylococcus aureus. Journal of Clinical Microbiology 41, 4089-4094 (2003).

44. C. E. Okolie, K. G. Wooldridge, D. P. J. Turner, A. Cockayne, R. James, Development of a heptaplex PCR assay for identification of Staphylococcus aureus and CoNS with simultaneous detection of virulence and antibiotic resistance genes. BMC Microbiology 15, 157 (2015).

45. N. K. Qureshi, S. H. Yin, S. Boyle-Vavra, The Role of the Staphylococcal VraTSR Regulatory System on Vancomycin Resistance and vanA Operon Expression in Vancomycin-Resistant Staphylococcus aureus. PLOS One 9, e85873 (2014).

46. K. W. Wang, T. Betancourt, C. K. Hall, Computational Study of DNA-Cross-Linked Hydrogel Formation for Drug Delivery Applications. Macromolecules 51, 9758-9768 (2018).

47. D. C. Lin, B. Yurke, N. A. Langrana, Mechanical properties of a reversible, DNA-crosslinked polyacrylamide hydrogel. Journal of Biomechanical Engineering-Transactions of the ASME 126, 104-110 (2004).

48. B. Wei, I. Cheng, K. Q. Luo, Y. L. Mi, Capture and release of protein by a reversible DNA-induced sol-gel transition system. Angewandte Chemie-International Edition 47, 331-333 (2008).

49. K. Barker et al., Biodegradable DNA-enabled poly (ethylene glycol) hydrogels prepared by copper-free click chemistry. Journal of Biomaterials Science-Polymer Edition 27, 22-39 (2016).

50. Z. Zhu et al., An Aptamer Cross-Linked Hydrogel as a Colorimetric Platform for Visual Detection. Angewandte Chemie-International Edition 49, 1052-1056 (2010).

51. R. Hajian et al., Detection of unamplified target genes via CRISPR-Cas9 immobilized on a graphene field-effect transistor. Nature Biomedical Engineering. Advance online publication. doi: 10.1038/s41551-019-0371-x (2019).

52. L. Magro et al., Paper-based RNA detection and multi-plexed analysis for Ebola virus diagnostics. Scientific Reports 7, 1347 (2017).

53. W. Cai, S. B. Xie, J. Zhang, D. Y. Tang, Y. Tang, An electrochemical impedance biosensor for Hg2+ detection based on DNA hydrogel by coupling with DNAzyme-assisted target recycling and hybridization chain reaction. Biosens. Bioelectron. 98, 466-472 (2017).

54. Y. Z. Xing et al., Self-assembled DNA hydrogels with designable thermal and enzymatic responsiveness. Adv. Mater. 23, 1117-1121 (2011).

55. X. Z. Ma et al., Remote controlling DNA hydrogel by magnetic field. ACS Appl. Mater. Inter. 9, 1995-2000 (2017).

56. S. Venkatesh, J. Wower, M. E. Byrne, Nucleic acid therapeutic carriers with on-demand triggered release. Bioconjugate Chem. 20, 1773-1782 (2009).

57. Y. Y. Chang et al., Homogeneous entropy catalytic-driven DNA hydrogel as strong signal blocker for highly sensitive electrochemical detection of platelet-derived growth factor. Anal. Chem. 90, 8241-8247 (2018).

58. G. Sicilia et al., Programmable polymer-DNA hydrogels with dual input and multiscale responses. Biomater. Sci. 2, 203-211 (2014).

59. M. Gao, K. Gawel, B. T. Stokke, Toehold of dsDNA exchange affects the hydrogel swelling kinetics of a polymer-dsDNA hybrid hydrogel. Soft Matter 7, 1741-1746 (2011).

60. S. H. Li, N. C. Chen, Z. Y. Zhang, Y. Wang, Endonu-clease-responsive aptamer-functionalized hydrogel coating for sequential catch and release of cancer cells. Biomaterials 34, 460-469 (2013).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B." or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

---

What is claimed is:

1. A composition comprising:
  (i) a hydrogel comprising a plurality of structural components, wherein the plurality of structural components comprise polyethylene glycol (PEG) covalently bound to one or more DNA molecules, wherein the one or more DNA molecules comprise a single-stranded region; and
  (ii) a Cas12a protein, a guide RNA corresponding to the Cas12a protein, and a double-stranded DNA trigger molecule, wherein the guide RNA comprises a spacer region that is at least 85% complementary to a target sequence of the double-stranded DNA trigger molecule,
  wherein the Cas12a protein is capable of cleaving the single-stranded region of the one or more DNA molecules in the hydrogel following cleavage of the double-stranded DNA trigger molecule.

2. The composition of claim 1, further comprising an additional guide RNA, wherein the additional guide RNA complements a sequence of the one or more DNA molecules in the hydrogel.

3. The composition of claim 1, wherein the spacer region of the guide RNA is at least 90% complementary to the target sequence of the double-stranded DNA trigger molecule.

4. The composition of claim 1, wherein the spacer region of the guide RNA is at least 95% complementary to the target sequence of the double-stranded DNA trigger molecule.

5. The composition of claim 1, wherein the spacer region of the guide RNA is 100% complementary to the target sequence of the double-stranded DNA trigger molecule.

* * * * *

SEQUENCE LISTING

```
<160> NUMBER OF SEQ ID NOS: 47

<210> SEQ ID NO 1
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 1
ggguaauuuc uacuaagugu agauuuaaag aagaugguau gugg                    44

<210> SEQ ID NO 2
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 2
tttaattttg ttaaagaaga tggtatgtgg aagttagatt                        40

<210> SEQ ID NO 3
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 3
tagtagtgat tatgttagat agtgaatagg tttaatgtat                        40

<210> SEQ ID NO 4
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 4
tttaattttg ttaaagaaga tgttatgtgg aagttagatt                        40

<210> SEQ ID NO 5
<211> LENGTH: 40
<212> TYPE: DNA
<213> ORGANISM: Artificial Sequence
```

-continued

```
<220> FEATURE:
<223> OTHER INFORMATION: Synthetic Polynucleotide

<400> SEQUENCE: 5
tttaattttg ttaaataaga tgttatgtag aagttagatt                          40

<210> SEQ ID NO 6
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 6
agcttgtctg ccatggacat gcagactata ctgttattgt tgtacagacc gaattccc      58

<210> SEQ ID NO 7
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 7
agggaattcg gtctgtacaa caataac                                        27

<210> SEQ ID NO 8
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 8
tttaattttg ttaaagaaga tggtatgtgg acgtatggaa taagtg                   46

<210> SEQ ID NO 9
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 9
tcacttattc catacgtcca cataccatct tctttaacaa aattaa                   46

<210> SEQ ID NO 10
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 10
ttattattta caacgtcgtg actgggaaaa cccttggaat aagtg                    45

<210> SEQ ID NO 11
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 11
tcacttattc caagggtttt cccagtcacg acgttgtaaa taata                    45
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
ttattcttgt ctcccgagat                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
ttatttcaca gatgagtatc                                              20

<210> SEQ ID NO 14
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 14
gatactcatc tgtgaatctc gggagacaag                                   30

<210> SEQ ID NO 15
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 15
gatactcatc tgtgattatt atctcgggag acaag                             35

<210> SEQ ID NO 16
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 16
gatactcatc tgtgattatt ttattttatt atctcgggag acaag                  45

<210> SEQ ID NO 17
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 17
gggtaatttc tactaagtgt agatttaaag aagatggtat gtggg                  45

<210> SEQ ID NO 18
<211> LENGTH: 44
<212> TYPE: DNA
<213> ORGANISM: Artificial Sequence
<220> FEATURE:
<223> OTHER INFORMATION: Synthetic Polynucleotide
```

-continued

<400> SEQUENCE: 18
gggtaatttc tactaagtgt agatattttg ttaaagaaga tggt                        44

<210> SEQ ID NO 19
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 19
gggtaatttc tactaagtgt agatacaaaa ttaaattgaa cgtt                        44

<210> SEQ ID NO 20
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 20
ttattattac tatctattat cattatcatt                                       30

<210> SEQ ID NO 21
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 21
tttacacaag cactacgtac actaccacat                                       30

<210> SEQ ID NO 22
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 22
atgtggtagt gtacgtagtg cttgtgtaaa                                       30

<210> SEQ ID NO 23
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 23
tttttattta tctatctgac ga                                               22

<210> SEQ ID NO 24
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 24
tcgtcagata gataaataaa aa                                               22

<210> SEQ ID NO 25

-continued

```
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 25
ttattattac tatctattat cattatcatt                                    30

<210> SEQ ID NO 26
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 26
ggguaauuuc uacuaagugu agaucuauua augguggaga ugga                    44

<210> SEQ ID NO 27
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 27
ggguaauuuc uacuaagugu agauaaucgu caauuccugc augu                    44

<210> SEQ ID NO 28
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 28
ggguaauuuc uacuaagugu agauugguaa ugcuugagcu uugu                    44

<210> SEQ ID NO 29
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 29
ggguaauuuc uacuaagugu agauguauuc aucaggaagu cgag                    44

<210> SEQ ID NO 30
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 30
gctttgggtt tactattaat ggtggagatg gatataaaaa                         40

<210> SEQ ID NO 31
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 31
```
taatattgtt taaatcgtca attcctgcat gttttaagga                    40

<210> SEQ ID NO 32
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 32
ttcaccagtt tctggtaatg cttgagcttt gttagcatct                    40

<210> SEQ ID NO 33
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 33
acggaatctt tcgtattcat caggaagtcg agccggaaaa                    40

<210> SEQ ID NO 34
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 34
gtgcgcgttc ctactgtatt tcataagaag agagttgaac cattaacagt tcctccagca    60
cctaaagaca tatgtccgac cttgaaaaaa ggattttttgt gtgacagtag tttttgcaaa    120
aaagaccacc agttagaaag tttaactgat agggaattac tcctactaat cgcccgtaag    180
acttgtggat cagtagaaca acaattaaat ataactgcac ccaaggactc g            231

<210> SEQ ID NO 35
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 35
ctactgtatt tcataagaag agagttgaac c                             31

<210> SEQ ID NO 36
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 36
aattgttgtt ctactgatcc acaagtctta c                             31

<210> SEQ ID NO 37
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 37

-continued gcgctaatac gactcactat agggtgcgcg ttcctactgt att                    43

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
gtgcgcgttc ctactgtatt                                             20

<210> SEQ ID NO 39
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 39
gagtccttgg gtgcagttat att                                         23

<210> SEQ ID NO 40
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 40
gggtaatttc tactaagtgt agatggtgct ggaggaactg ttaa                  44

<210> SEQ ID NO 41
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 41
ggguaauuuc uacuaagugu agauauuuug uuaaagaaga uggu                  44

<210> SEQ ID NO 42
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 42
ggguaauuuc uacuaagugu agauacaaaa uuaaauugaa cguu                  44

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
attttgttaa agaagatggt                                             20

<210> SEQ ID NO 44
<211> LENGTH: 20
<212> TYPE: DNA
<213> ORGANISM: Artificial Sequence -continued

```
<220> FEATURE:
<223> OTHER INFORMATION: Synthetic Polynucleotide

<400> SEQUENCE: 44
acaaaattaa attgaacgtt                                                    20

<210> SEQ ID NO 45
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 45
ggguaauuuc uacuaagugu agauguaugg cuucauucag cucc                         44

<210> SEQ ID NO 46
<211> LENGTH: 44
<212> TYPE: RNA
<213> ORGANISM: Artificial Sequence
<220> FEATURE:
<223> OTHER INFORMATION: Synthetic Polynucleotide

<400> SEQUENCE: 46
ggguaauuuc uacuaagugu agauguaugg cuucauucag cucc                         44

<210> SEQ ID NO 47
<211> LENGTH: 46
<212> TYPE: DNA
<213> ORGANISM: Artificial Sequence
<220> FEATURE:
<223> OTHER INFORMATION: Synthetic

<400> SEQUENCE: 47
tgatactcat ctgtgattat tttattttat tatctcggga gacaag                       46
```